US009701684B2

(12) United States Patent
Gouverneur et al.

(10) Patent No.: US 9,701,684 B2
(45) Date of Patent: Jul. 11, 2017

(54) CHIRAL FLUORINATING REAGENTS

(71) Applicant: Oxford University Innovation Limited, Oxford (GB)

(72) Inventors: Veronique Gouverneur, Oxford (GB); Graham Sandford, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/440,530

(22) PCT Filed: Nov. 5, 2013

(86) PCT No.: PCT/GB2013/052892
§ 371 (c)(1),
(2) Date: May 4, 2015

(87) PCT Pub. No.: WO2014/068341
PCT Pub. Date: May 8, 2014

(65) Prior Publication Data

US 2015/0284401 A1 Oct. 8, 2015

(30) Foreign Application Priority Data

Nov. 5, 2012 (GB) .................................. 1219820.6

(51) Int. Cl.
*C07D 487/08* (2006.01)
*C07D 215/58* (2006.01)
*C07C 17/14* (2006.01)
*C07C 17/361* (2006.01)

(52) U.S. Cl.
CPC ............ *C07D 487/08* (2013.01); *C07C 17/14* (2013.01); *C07C 17/361* (2013.01); *C07D 215/58* (2013.01); *C07B 2200/07* (2013.01); *C07C 2102/08* (2013.01); *C07C 2103/40* (2013.01)

(58) Field of Classification Search
CPC .................................................. C07D 487/08
See application file for complete search history.

(56) References Cited

U.S. PATENT DOCUMENTS

| 5,086,178 | A | * | 2/1992 | Banks ................... C07D 487/08 540/472 |
| 5,631,372 | A | | 5/1997 | Poss et al. |
| 5,886,178 | A | | 3/1999 | Allen et al. |
| 2006/0189830 | A1 | | 8/2006 | MacMillan et al. |
| 2013/0023661 | A1 | | 1/2013 | Ignatyev et al. |

FOREIGN PATENT DOCUMENTS

| EP | 0657457 A1 | 6/1995 |
| EP | 0748807 A1 | 12/1996 |
| WO | 95/17404 A1 | 6/1995 |
| WO | 01/74741 A2 | 10/2001 |
| WO | 01/90107 A1 | 11/2001 |
| WO | 2011/124307 A1 | 10/2011 |
| WO | 2014/068341 A2 | 5/2014 |
| WO | 2014/068341 A3 | 6/2014 |
| WO | 2014/068341 A4 | 8/2014 |

OTHER PUBLICATIONS

Search Report issued in a United Kingdom Patent Application No. GB1219820.6 dated Feb. 21, 2013.
Farkas et al., "Some Derivatives of 1,4-diazabicyclo[2.2.2]octane (triethylenediamine)", Journal of Chemical & Engineering Data, vol. 13, No. 2, 1968, pp. 278-284.
Fukuzumi et al., "Enantioselective Fluorination Mediated by Cinchona Alkaloids/Selectfluor Combinations: A Catalytic Approach", Journal of Fluorine Chemistry, Elsevier, vol. 127, No. 4-5, May 1, 2006, pp. 548-551.
Kessar et al., "Facile α-Deprotonation-Electrophilic Substitution of Quinuclidine and DABCO", Chemical Communications, No. 19, Jan. 1, 1999, pp. 1927-1928.
PCT International Patent Application No. PCT/GB2013/052892, International Search Report and Written Opinion mailed May 8, 2014, 21 pages.
Shibata et al., "A Fundamentally New Approach to Enantioselective Fluorination Based on Cinchona Alkaloid Derivatives/Selectfluor Combination", Journal of the American Chemical Society, vol. 122, 2000, pp. 10728-10729.
Shibata et al., "Enantioselective Fluorination Mediated by Cinchona Alkaloid Derivatives/Selectfluor Combinations: Reaction Scope and Structural Information for N-Fluorocinchona Alkaloids", Journal of the American Chemical Society, vol. 123, 2001, pp. 7001-7009.
Shishkin et al., "Diazabicycloalkanes with Nitrogen Atoms in the Nodal Positions. 5.* Synthesis and Some Reactions of 2-Hydroxymethyl-1,4-Diazabicyclo[2.2.2]Octane", Jan. 1, 1980, pp. 1069-1072.
Shishkin et al., "Diazabicycloalkanes with Nitrogen Atoms in the Nodal Positions. 7. Synthesis and Configuration of 2,3-diphenyl-1,4-Diazabicyclo[2.2.2]-Octane", Chemistry of Heterocyclic Compounds, vol. 18, 1982, pp. 80-84.
Soai et al., "Synthesis of (2s,5s)-2,5-bis(phenylmethyl)-1,4-diazabicyclo[2.2.2] Octane", Tetrahedron: Asymmetry, vol. 3, No. 3, 1992, pp. 359-360.
Sun et al., "Synthesis of Novel Chiral Fluorinating Agents, (+)- and (−)-N-Fluoro-3-Methyl-3-(4-Methylphenyl)-2H-Benzo[e][1,2]Thiazine-1,1,4-triones", Chinese Chemical Letters, Elsevier, vol. 19, 2008, pp. 907-910.

(Continued)

*Primary Examiner* — Noble Jarrell
*Assistant Examiner* — John S Kenyon
(74) *Attorney, Agent, or Firm* — Morgan, Lewis & Bockius LLP

(57) ABSTRACT

This invention relates to fluorinating agents and, more particularly, to chiral non-racemic fluorinating agents useful for enantioselective fluorination, as well as to their synthesis and use and other subject matter. The fluorinating agents are based on a substituted 1,4-diazabicyclo[2.2.2]octane (DABCO) skeleton and provide electrophillic fluorine enantioselectively.

17 Claims, 2 Drawing Sheets

(56) References Cited

OTHER PUBLICATIONS

Vysochin et al., "Diazabicycloalkanes with Nitrogen Atoms at the Nodal Positions. 12. Stephens Rearrangement in Substituted 1,4-Diazabicyclo[2.2.2]Octanes", Chemistry of Heterocyclic Compounds, vol. 21, No. 5, May 1985, pp. 559-563.
Vysochin et al., "Diazabicycloalkanes with Nitrogen Atoms in the Nodal Positions. 8. Effect of C-Substituents on the N-Methylation of 1,4-Diazabi Cyclo[2.2.2]Octanes and the Demethylation of their Bisquaternary Salts", Chemistry of Heterocyclic Compounds vol. 18, No. 2, Feb. 1982, pp. 196-201.
PCT International Patent Application No. PCT/GB2013/052892, International Preliminary Report on Patentability issued May 5, 2015, 13 pages.
Communication pursuant to Article 94(3) EPC issued in a corresponding European Patent Application No. 13786748.7 dated Mar. 14, 2016.
Wolstenhulme et al., "Asymmetric Electrophilic Fluorocyclization with Carbon Nucleophiles," Angewandte Chemie International Edition, 52(37): 9796-9800 (2013).

* cited by examiner

CHIRAL FLUORINATING REAGENTS

This application is the U.S. national stage application of International (PCT) patent application Ser. No. PCT/GB2013/052892, filed Nov. 5, 2013, which claims the benefit of GB Application No. 1219820.6, filed Nov. 5, 2012. The entire disclosure of each of these applications is hereby incorporated by reference.

COMPOUNDS

This invention relates to fluorinating agents and, more particularly, to chiral non-racemic fluorinating agents useful for enantioselective fluorination, as well as to their synthesis and use and other subject matter.

BACKGROUND

A standard achiral electrophilic fluorinating reagent is sold under the registered trade mark Selectfluor. This reagent described in U.S. Pat. No. 5,086,178 is as follows:

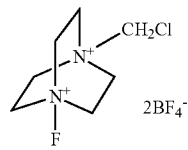

The most efficient chiral reagent for electrophilic fluorination is a mixture of Selectfluor and a cinchona alkaloid as a chiral transfer reagent; see Shibata N et al., *J. Am. Chem. Soc.* 2000, 122, 10728-10729 and Shibata N et al., *J. Am. Chem. Soc.* 2001, 123, 7001-7009. This reaction involves generation of an intermediate fluorinated cinchona alkaloid. The intermediate fluorinated cinchona alkaloid described by Shibata (see above) has been found to be less reactive than desirable and to achieve varying levels of enantiomeric excess and/or yield, depending on the substrate.

The following compound, 1,4-diazabicyclo[2.2.2]octane, is known in the art by the acronym DABCO:

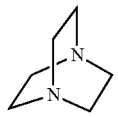

BRIEF SUMMARY OF THE DISCLOSURE

It has therefore now been appreciated that it would be desirable to provide novel fluorinating agents which are more reactive than fluorinated cinchona alkaloid intermediates. It has also been appreciated that it would be desirable to provide a library of two or more fluorinating agents; each member of the library will have a different structure and therefore a different substrate class (of one or more molecules) with which it optimally performs.

The present invention provides in one aspect a reagent for electrophilic fluorination, comprising a chiral compound having an N-fluorinated and N'-substituted DABCO scaffold. The invention therefore includes, in one embodiment, such N-fluorinated, N'-substituted DABCO compounds in which one or more carbon atoms of the DABCO scaffold form a chiral centre. Thus, in an embodiment, the reagent is chiral by virtue of at least one carbon atom of the DABCO scaffold being substituted so that none of its four bonds is equivalent, such as to provide a chiral centre. The invention also includes, in another embodiment, such N-fluorinated, N'-substituted DABCO compounds in which none of the carbon atoms of the DABCO scaffold form a chiral centre. Thus, in an embodiment, the reagent is chiral by virtue of each of the nitrogen atoms of the DABCO being substituted so that none of its four bonds is equivalent. In either embodiment, the N'-substituted nitrogen is substituted by a moiety other than F, or is substituted by F and the two F-substituted nitrogen atoms of the scaffold are indistinguishable. In structural terms, but not necessarily in terms of synthetic route, these compounds may be regarded as derivatives of DABCO in which one bridgehead nitrogen is substituted (quaternised) by fluorine and the other bridgehead nitrogen is substituted (quaternised) by fluorine or another substituent. The N-fluorinated DABCO compound may be N,N'-difluorinated solely in those compounds where the two nitrogen atoms are indistinguishable from one another and therefore react identically with a substrate. A chiral species is one which has a non-superimposable mirror image; this can be readily determined by drawing the species in question, drawing its mirror image and comparing the structures.

In accordance with one aspect of the invention, there is also provided a product comprising a non-racemic chiral species having a structure of Formula (Ia):

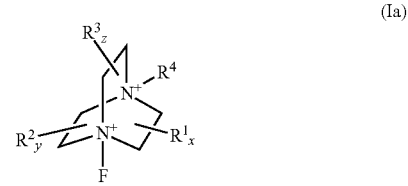

wherein:
each $R^1$, $R^2$ and $R^3$ is an independently selected substituent;
$R^4$ is an independently selected substituent other than fluorine; and
x, y and z are each independently 0, 1, 2, 3 or 4, provided that at least one of x, y and z is not 0.

In accordance with another aspect of the invention, there is also provided a product comprising a non-racemic chiral species having a structure of Formula (Ib):

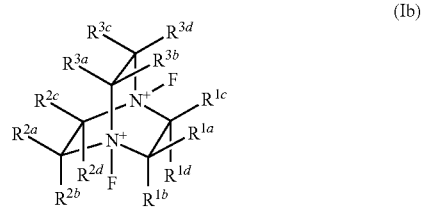

wherein: $R^{1a}$, $R^{1b}$, $R^{1c}$, $R^{1d}$, $R^{2a}$, $R^{2b}$, $R^{2c}$, $R^{2c}$, $R^{2d}$, $R^{3a}$, $R^{3b}$, $R^{3c}$ and $R^{3d}$ are each H or a substituent, provided that at least two of $R^{1a}$, $R^{1b}$, $R^{1c}$, $R^{1d}$, $R^{2a}$, $R^{2b}$, $R^{2c}$ and $R^{2d}$ are not H and:
$R^{1a}$ and $R^{2c}$ are both the same moiety;
$R^{1b}$ and $R^{2d}$ are both the same moiety;
$R^{1c}$ and $R^{2a}$ are both the same moiety;

$R^{1d}$ and $R^{2b}$ are both the same moiety;
$R^{3a}$ and $R^{3d}$ are both the same moiety; and
$R^{3b}$ and $R^{3c}$ are both the same moiety.

The invention includes the use as an electrophilic fluorinating reagent of products comprising a chiral species of Formula (Ia) or (Ib).

In other aspects, the invention provides intermediates for making the aforesaid products, namely (a) products comprising a non-racemic chiral species having a structure of Formula (II) and (b) non-racemic chiral compounds of Formula (III):

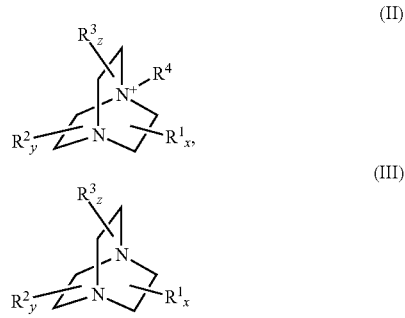

wherein $R^1$, $R^2$, $R^3$, $R^4$, x, y and z are as defined in relation to Formula (Ia). An intermediate of Formula (III), namely (R,S)-2,3-diphenyl-1,4-diazabicyclo[2.2.2]octane, is disclosed in Oi R and Sharpless K B, *Tetrahedron Lett.* 1991, 32, 4853-4854, and is not as such included in the invention, although its use as an intermediate in the manufacture of the fluorinating agents described herein is included in the invention. One embodiment of the invention resides in compounds of Formula (III) provided that the compound is not a 2,3-diphenyl-1,4-diazabicyclo[2.2.2]octane. Thus, the invention provides a process for preparing a compound of Formula Ia in situ comprising: reacting a compound of Formula II with a fluorinating agent, e.g. Selectfluor. The invention also provides a process for preparing a compound of Formula Ib in situ comprising: reacting a compound of Formula III with a fluorinating agent, e.g. Selectfluor.

BRIEF DESCRIPTION OF THE DRAWINGS

Embodiments of the invention are further described hereinafter with reference to the accompanying drawings, in which.

DETAILED DESCRIPTION

Figure 1:
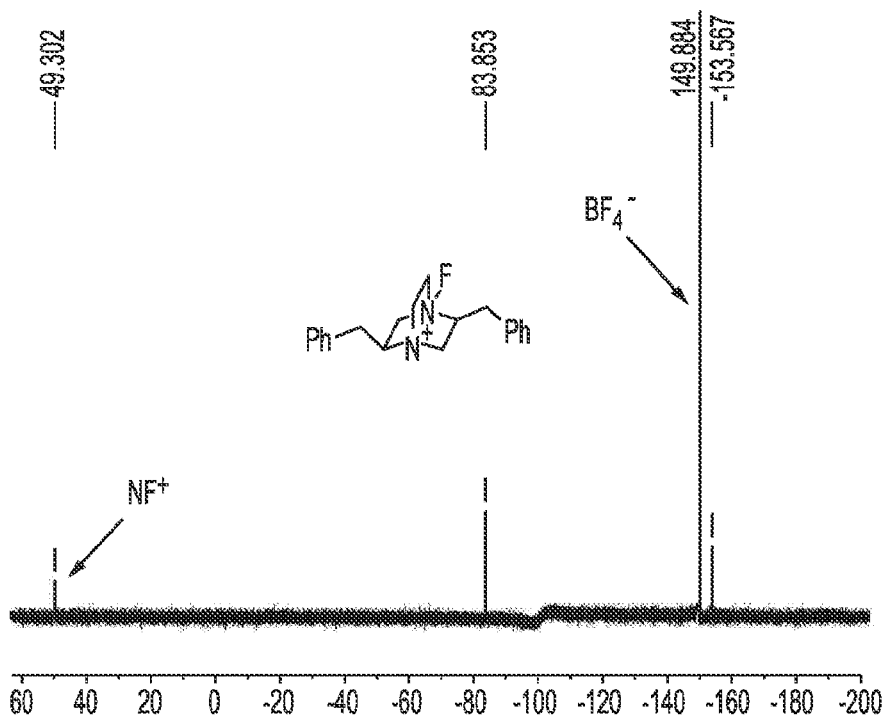
FIG. 1 is a $^{19}F$ NMR of fluorinated isomer 112.
Figure 2:
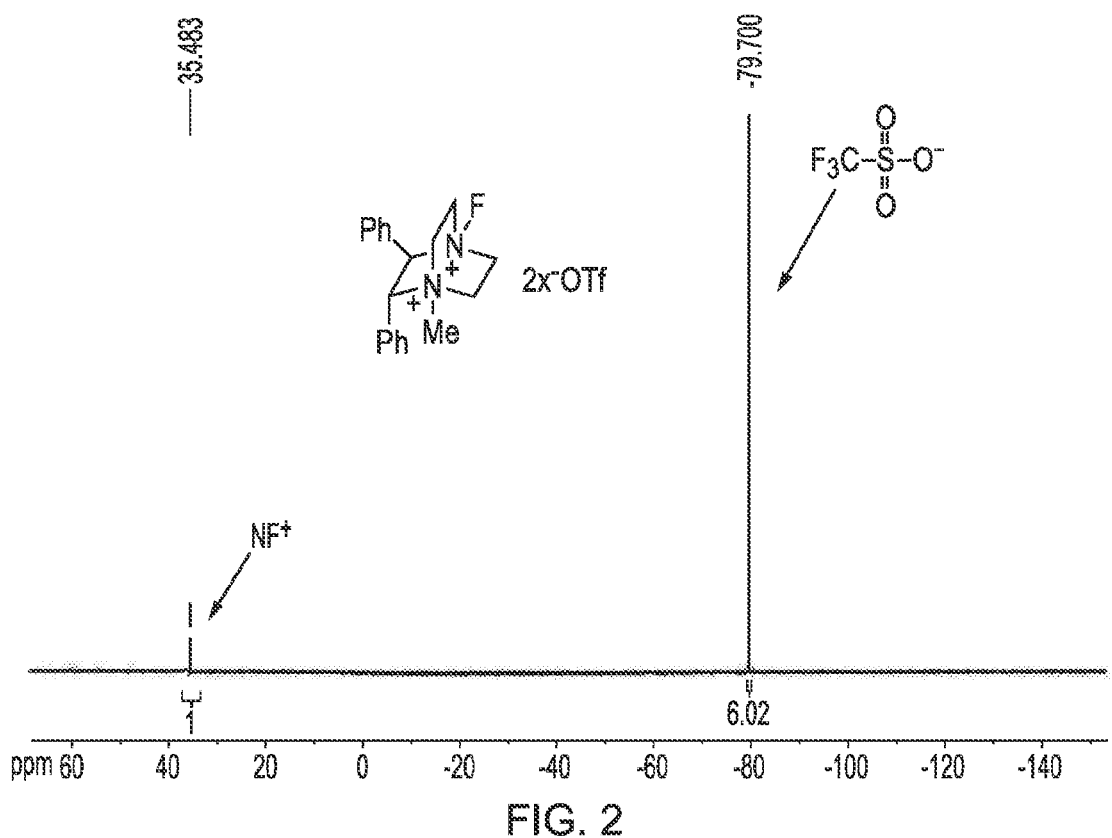
FIG. 2 is a $^{19}F$ NMR of fluorinated isomer 29.
Figure 3:
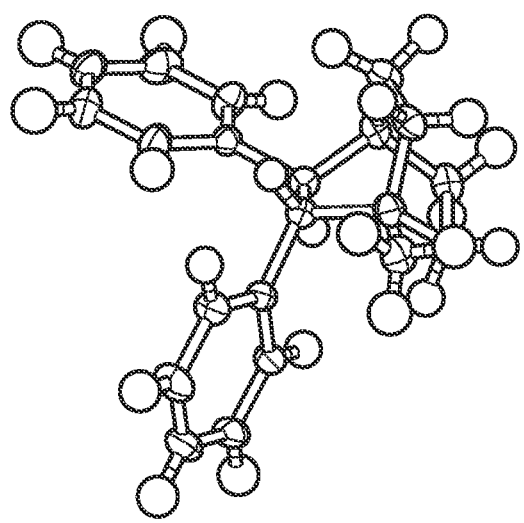
FIG. 3 shows the X-ray crystal structure of 27.
Figure 3:
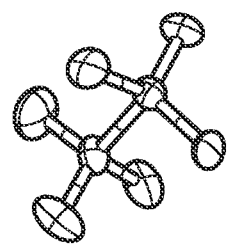
Figure 4:
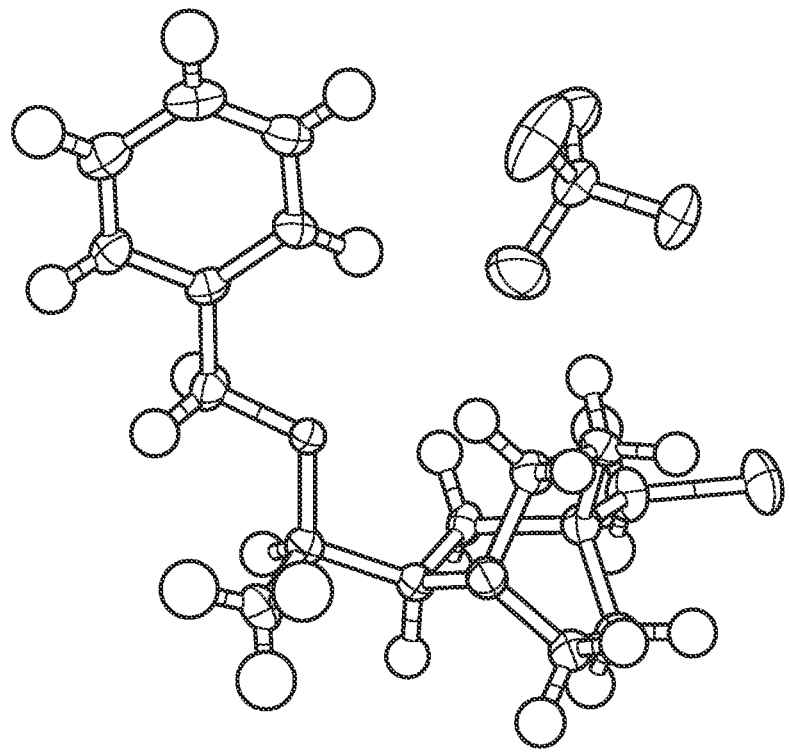
FIG. 4 shows the X-ray crystal structure of 59.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are mentioned in this specification, and the contents of all such papers and documents are incorporated herein by reference.

The term "alkyl" as used herein includes reference to alkyl groups having from 1 to 10 carbon atoms and particularly 1, 2, 3, 4, 5 or 6 carbon atoms, e.g. methyl, ethyl, n-propyl, i-propyl, n-butyl, i-butyl and t-butyl. Alkyl groups may be linear or branched and in particular are linear. This paragraph applies equally to the alkyl part of alkoxy; particular alkoxy groups are methoxy and ethoxy. The term "aryl" includes reference to phenyl and naphthyl. The term "heteroaryl" includes reference to mono- and bicyclic heteroaromatic rings, for example pyridine, furan, thiophene, pyrimidine, quinoline and isoquinoline.

The term "optionally substituted" means "substituted or unsubstituted" and, in each instance that the term "optionally substituted" is used, the two alternatives of substitution and non-substitution are therefore disclosed.

The term "independently selected" means selected independently of other selections of the same group if it occurs more than once in a molecule. Thus, if there are two occurances of a group in a molecule those groups may be the same or different.

The term "substituent" refers to an organic or inorganic moiety other than hydrogen. However, the skilled person will not of course select unreasonable, e.g. undesirably reactive substituents.

In one aspect, the invention provides a reagent for electrophilic fluorination, comprising a chiral, non-racemic compound having an N-fluorinated and N'-substituted DABCO scaffold. The invention therefore includes, in one embodiment, such compounds in which the DABCO scaffold has a chiral substituted carbon atom. The invention also includes, in another embodiment, such compounds in which the DABCO scaffold has no chiral carbon atoms; in this case, the compound may be chiral by virtue of each of the nitrogen atoms of the DABCO being substituted so that none of its four bonds is equivalent. As the N'-substituent may be mentioned alkyl, haloalkyl and similar substantially inert moieties, this substituent being however described in more detail below. The invention therefore includes products useful as electrophilic fluorinating reagents and comprising a chiral species having a structure of Formula (Ia):

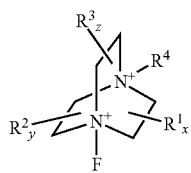
(Ia)

wherein each $R^1$, $R^2$, $R^3$ and $R^4$ is an independently selected substituent, except that $R^4$ cannot be fluorine; and x, y and z are each independently 0, 1, 2, 3 or 4, provided that at least one of x, y and z is not 0. For all embodiments of Formula (Ia), where there are two or more substituents, the identity of any substituent is not dependent on the identity of any other substituent, provided that the species of Formula (Ia) is chiral; but particular species have two identical substituents on different carbon atoms. The chiral centre is suitably located at a carbon atom a to the F-bearing nitrogen shown in Formula (Ia).

The invention further includes products useful as electrophilic fluorinating reagents and comprising a chiral species having a structure of Formula (Ib):

(Ib)

wherein:
$R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3c}$ and $R^{3d}$ are each H or a substituent, provided that at least two of $R^{1a}$, $R^{1b}$, $R^{1c}$, $R^{1d}$, $R^{2a}$, $R^{2b}$, $R^{2c}$ and $R^{2d}$ are not H and:
$R^{1a}$ and $R^{2c}$ are both the same moiety;
$R^{1b}$ and $R^{2d}$ are both the same moiety;
$R^{1c}$ and $R^{2a}$ are both the same moiety;
$R^{1d}$ and $R^{2b}$ are both the same moiety;
$R^{3a}$ and $R^{3d}$ are both the same moiety; and
$R^{3b}$ and $R^{3c}$ are both the same moiety.

The two bridgehead nitrogens of Formula (Ib) are stereochemically identical with respect to the DABCO scaffold and they may therefore both be substituted by fluorine.

The chiral species of the invention are dicationic and are therefore provided as compositions comprising also a counterion, for example salts comprising a counterion $X^{m-}$:

$[X^{m-}]_{2/m}$ $[X^{m-}]_{2/m}$ wherein index m is the ionic charge, e.g. 1 or 2, by way of example. Likewise, the chiral species of formula II are monocationic and are therefore provided as compositions comprising also a counterion for example salts comprising a counterion $X^{m-}$:

$[X^{m-}]_{1/m}$ wherein index m is the ionic charge, e.g. 1 or 2, by way of example. Each X may be the same or different. Thus, for example, if m is 1, $[X^{m-}]_{2/m}$ may be $[X_a^-]_2$ or it may be $[X_a^-][X_b^-]$, wherein $X_a$ and $X_b$ are different.

The products of the invention therefore include salts and salt solutions.

Suitable counterions (i.e. X, $X_a$ or $X_b$ from paragraph [0021]) include $BF_4^-$ and triflate ($F_3C—S(O)_2O^-$). Other suitable counterions (i.e. X, $X_a$ or $X_b$ from paragraph [0021]) are, for example, halides, especially fluoride; fluorosulfate ($SO_3F^-$); alkanesulfonates, especially methanesulfonate ($CH_3SO_3^-$); alkylsulfates, especially methylsulfate ($CH_3OSO_3^-$); perfluoroalkanesulfonates, especially nonaflate ($C_4F_{12}SO_3^-$) as well as triflate; arenesulfonates, especially tosylate (p-$CH_3—C_6H_4SO_3^-$); alkanecarboxylates; perfluoroalkanecarboxylates; tetraphenylborate; hexafluorophosphate; hexafluoroantiminate; chlorate and sulphate.

$R^1$, $R^2$ and $R^3$

This section of the specification (paragraphs [0024] to [0041]) describes the possibilities for the substituents designated $R^1$, $R^2$ and $R^3$. It will be recalled in this regard that x, y and z are each independently 0, 1, 2, 3 or 4, provided that at least one of x, y and z is not 0; i.e. substituents $R^1$, $R^2$ and $R^3$ are optional provided that the carbon atoms of the DABCO scaffold have at least one substituent between them.

Advantageously, the or each substituent is a moiety which is chemically inert under the conditions in which the products of the invention are typically used. Advantageously, the or each substituent does not include a site susceptible to electrophilic fluorination by the N-F fluoro of the compound. For example, the or each substituent may be an independently selected hydrocarbyl group, wherein hydrocarbyl is optionally substituted by at least one fluorine and/or optionally interrupted by or linked to the remainder of the molecule through an ether linkage, or both so interrupted and linked. However, the invention is not limited as to the identity of the substituents $R^1$, $R^2$ and $R^3$, and includes moieties $R^1$, $R^2$ and $R^3$ containing at least one chiral centre. In one embodiment, the substituents $R^1$, $R^2$ and/or $R^3$, where present, are each independently selected from the following listed groups and from moieties which are combinations of two or more moieties selected from the listed groups and the following listed linkages, as in the case of such combinations wherein the number of linkages does not exceed the number of groups:

| Listed Groups | Listed linkages |
|---|---|
| alkyl | carbonyl |
| cyclic ether | carboxy |
| aryl | —O— |

| Listed Groups | Listed linkages |
|---|---|
| heteroaryl | —S— |
| alkenyl | sulphonyl |
| cycloalkyl | sulphonamide |
| cycloalkenyl | amide |
|  | amine |
|  | alkyl. |

The listed linkages may therefore be present in the substituents $R^1$, $R^2$ and/or $R^3$ between the DABCO scaffold and the remainder of the substituent (i.e. between the DABCO scaffold and one of the listed groups) and/or within the substituent (i.e. between two of the listed groups, which two groups may be the same or different). Similarly, a listed group may be bonded to the DABCO scaffold directly or through a listed linkage. Where a substituent contains a plurality of listed groups, each listed group is selected independently from each other group; for example, the substituent may comprise two groups falling within the same genus (e.g. two alkyl groups or two aryl groups) or, in another example, it may contain at most one group from any genus. The listed groups may independently be unsubstituted or substituted one or more times by suitable substituents (advantageously not including nucleophilic groups such as primary, secondary and tertiary amino groups), for example selected from halo (particularly fluoro), cyano, carboxy, sulphoxy and nitro.

Alkyl groups may be straight chain or branched, and may have for example, 1, 2, 3, 4, 5 or 6 carbon atoms. Cyclic ethers typically have 5 or 6-membered rings and examples are THF and dioxane. Aryl may for example be phenyl or naphthyl, particularly phenyl. Heteroaryl may for example be an aromatic mono- or bicyclic ring containing at least one heteroatom, exemplary heteroaryl groups being pyridine, pyrimidine, quinoline and isoquinoline.

As examples of moieties which are combinations of species selected from the listed groups and linkages may be mentioned arylalkyl (e.g. benzyl or naphthylmethyl), aryl substituted by one or more alkyl groups, arylalkyl substituted on its aryl part by one or more alkyl groups, aryl or arylalkyl substituted by both alkyl and alkoxy, alkoxyarylalkyl, arylalkoxy, heteroarylalkyl, arylcarbonyloxyalkyl, aryloxycarbonylalkyl, aryloxyalkyl, and alkyl groups (e.g. methyl) disubstituted, whether directly or through a listed linkage, by listed groups. As an example of such a disubstituted alkyl group may be mentioned alkyl, particularly methyl, substituted by (1) heteroaryl or aryl and (2) oxycarbonylaryl (—O—CO-aryl).

In many cases, $R^1$, $R^2$ and $R^3$ areeach independently a moiety containing of from 1 to 30 plural valent atoms, e.g. from 1 to 25 plural valent atoms and optionally from 1 to 12 plural valent atoms. In some embodiments there are at least 4 plural valent atoms, e.g. at least 6 plural valent atoms; for example in one embodiment each $R^1$, $R^2$ and $R^3$ moiety present in the molecule has from 6 to 30 plural valent atoms. The term "plural valent atoms" may, for example, refer to atoms selected from C, N, O, S and P, particularly C, O, N and S, e.g. C, O and N, and in one embodiment refers to carbon atoms.

More particularly, the or each substituent ($R^1$, $R^2$ and/or $R^3$) may independently be -L-$R^5$. The or each L is independently a bond or an inert linker containing 1, 2, 3, 4, 5 or 6 in-chain atoms, e.g. from 1-4 in-chain atoms for example linkers having one or two in-chain atoms. The or each $R^5$ is a moiety having from 1 to 20 plural valent atoms, e.g. 1 to 15 plural valent atoms, selected from heteroaryl, heteroaryl substituted with one or more $R^{20}$ groups, hydrocarbyl and hydrocarbyl substituted with one or more $R^{20}$ groups. For example, hydrocarbyl may be substituted with one or more fluorines. In one embodiment hydrocarbyl is selected from alkyl and aryl. As an example, each $R^{20}$ group is independently selected from alkoxy, halogen (particularly fluoro or chloro), cyano, carboxy, sulphoxy and nitro; if an $R^{20}$ group is a substituent on an aryl or heteroaryl ring, the $R^{20}$ group may also be an alkyl group. The term "in-chain atom" refers to an atom which is part of a continuous chain of atoms (e.g. of 1-6 atoms) between $R^5$ and the remainder of the molecule.

L may more particularly be a bond, —$(CH_2)_n$—, —O—, —$O(CH_2)_n$—, —$(CH_2)_nO$—, or —$(CH_2)_p$—O—$(CH_2)_q$—, wherein n is 1, 2, 3 or 4 and p and q are integers such that (p+q) is 2, 3 or 4. Index n is in particular 1 or 2, e.g. is 1. In one embodiment L is a bond. In another embodiment L is not a bond, e.g. is —$(CH_2)_n$—. The invention includes an embodiment in which L is a bond or —$CH_2$—.

The or each $R^5$ is in particular a moiety having from 1 to 20 plural valent atoms, e.g. 1 to 15 carbon atoms, and independently selected from the group consisting of: (i) alkyl and alkenyl, in either case optionally substituted by at least one $R^{20}$ group as just described, e.g. at least one F; and (ii) a cyclic moiety which is selected from cycloalkyl, cycloalkenyl, heteroaryl and aryl and is optionally substituted by at least one substituent selected from the group consisting of: fluorine, alkyl and alkyl substituted by at least one fluorine (e.g. trifluoromethyl). In one embodiment, the possible substituents for cyclic moiety (ii) further include alkoxy, halogen, cyano, sulphoxy and nitro, as well as alkyl substituted by at least one substituent selected from alkoxy, halo, cyano, carboxy, sulphoxy and nitro. $R^5$ may have from 6 to 15 plural valent atoms, e.g. 6, 7, 8, 9, 10, 11 or 12 carbon atoms. In one embodiment, $R^5$ is a said optionally substituted cyclic moiety, for example having from 6 to 15 plural valent atoms. In one embodiment, the plural valent atoms are all carbon atoms.

Where there are two or more $R^5$ moieties, the moieties are independently chosen. In one class of species, however, there are two or more $R^5$ moieties which are all the same.

The invention includes an embodiment in which $R^5$ is phenyl or naphthyl, in either case optionally substituted by at least one substituent selected from the group consisting of: fluorine, alkyl and alkyl substituted by at least one fluorine. In one embodiment, the possible substituents for cyclic moiety (ii) further include alkoxy, halogen, cyano, sulphoxy and nitro, as well as alkyl substituted by at least one substituent selected from alkoxy, halo, cyano, carboxy, sulphoxy and nitro. For example, $R^5$ is phenyl or phenyl substituted by 1, 2, 3, 4 or 5 substituents selected from fluorine and trifluoromethyl.

In one embodiment, therefore, the or each L is independently a bond or —$(CH_2)_n$— and the or each $R^5$ is a moiety having from 1 to 15 carbon atoms and is independently selected from the group consisting of: alkyl or alkenyl, in either case optionally substituted by at least one F; or is cycloalkyl, cycloalkenyl or aryl optionally substituted by at least one substituent selected from the group consisting of: fluorine, alkyl and alkyl substituted by at least one fluorine.

In one embodiment, the or each substituent is independently selected from the group consisting of aryl, heteroaryl, —$(CH_2)_n$-aryl and —$(CH_2)_n$-heteroaryl (and in particular is selected from aryl and —$(CH_2)_n$-aryl), wherein n is 1, 2, 3 or 4, and wherein aryl and heteroaryl are optionally substituted by at least a single $R^{20}$ group, e.g. selected from halogen (e.g. F or Cl), alkyl and alkyl substituted by at least one halogen. By way of example, the or each aryl is independently phenyl or naphthyl whilst the or each heteroaryl is independently pyridine, pyrimidine, quinoline and isoquinoline, wherein phenyl, naphthyl, pyridine, pyrimidine, quinoline and isoquinoline are independently optionally substituted by at least one substituent selected from alkoxy, halo (particularly fluoro or chloro), cyano, carboxy, sulphoxy, nitro, alkyl and alkyl substituted by at least one halogen.

In one embodiment, at least one of $R^1$, $R^2$ and $R^3$ comprises a chiral centre. Thus, at least one of $R^1$, $R^2$ and $R^3$ may comprise an asymmetric carbon atom. For example, two or three of $R^1$, $R^2$ and $R^3$ may comprise an asymmetric carbon atom and be chiral.

In an embodiment, at least one of $R^1$, $R^2$ and $R^3$ comprises a chiral centre which is proximal to the DABCO scaffold, i.e. the carbon which is directly bonded to the DABCO scaffold is asymmetric. For example, two or three of $R^1$, $R^2$ and $R^3$ may comprise a chiral centre proximal to the DABCO scaffold.

$R^{1a}$, $R^{1b}$, $R^{1c}$, $R^{1d}$, $R^{2a}$, $R^{2b}$, $R^{2c}$ and $R^{2d}$ Moieties $R^{1a}$, $R^{1b}$, $R^{1c}$, $R^{1d}$, $R^{2a}$, $R^{2b}$, $R^{2c}$ and $R^{2d}$ are selected from H and substituents, notably the possibilities described in more detail above for $R^1$, $R^2$ and $R^3$. It will be recalled that Formula (Ib) requires $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3c}$ and $R^{3d}$ to be H or a substituent, provided that at least two of $R^{1a}$, $R^{1b}$, $R^{1c}$, $R^{1d}$, $R^{2a}$, $R^{2b}$, $R^{2c}$ and $R^{2d}$ are not H. The substituents $R^{1a}$ and $R^{2c}$ are both the same moiety; $R^{1b}$ and $R^{2d}$ are both the same moiety; $R^{1c}$ and $R^{2a}$ are both the same moiety; $R^{1d}$ and $R^{2b}$ are both the same moiety; $R^{3a}$ and $R^{3d}$ are both the same moiety; and $R^{3b}$ and $R^{3c}$ are both the same moiety.

In an embodiment relating to the species having structure according to Formula (Ib):

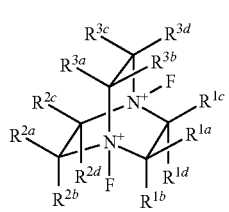

(Ib)

$R^{1a}$ and $R^{2c}$ are both the same moiety; $R^{1b}$ and $R^{2d}$ are both the same moiety and are different from $R^{1a}$ and $R^{2c}$; $R^{1c}$ and $R^{2a}$ are both the same moiety; $R^{1d}$ and $R^{2b}$ are both the same moiety and are different from $R^{1c}$ and $R^{2a}$; $R^{3a}$ and $R^{3d}$ are both the same moiety; and $R^{3b}$ and $R^{3c}$ are both the same moiety. In a related embodiment, the species has the structure (Ic) or (Id):

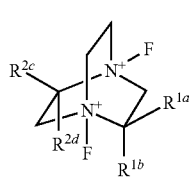

(Ic)

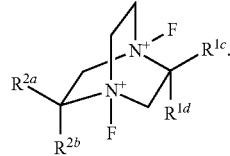

(Id)

In one embodiment, in which the species has a structure according to formula (1b), both members of at least one pair of substituents comprise a chiral centre, wherein the pairs of substituents are selected from: $R^{1a}$ and $R^{2c}$; $R^{1b}$ and $R^{2d}$; $R^{1c}$ and $R^{2a}$; $R^{1d}$ and $R^{2b}$; $R^{3a}$ and $R^{3d}$ and $R^{3b}$ and $R^{3c}$. In some embodiments in which the species has a structure according to formula (Ic), both members of at least one pair of substituents comprise a chiral centre, wherein the pairs of substituents are selected from: $R^{1a}$ and $R^{2c}$; and $R^{1b}$ and $R^{2d}$. In some embodiments in which the species has a structure according to formula (Id), both members of at least one pair of substituents comprise a chiral centre, wherein the pairs of substituents are selected from: $R^{1c}$ and $R^{2a}$; and $R_{1d}$ and $R^{2b}$. In any of these embodiments, both members of at least one pair of substituents comprise an asymmetric carbon atom. In any of these embodiments, both members of at least one pair of substituents may comprise a chiral centre which is proximal to the DABCO scaffold, i.e. the carbon which is directly bonded to the DABCO scaffold is asymmetric.

$R^4$ $R^4$ is a substituent other than fluorine. Advantageously, $R^4$ is a moiety which is chemically inert under the conditions in which the products of the invention are typically used. Advantageously, $R^4$ does not include a site susceptible to electrophilic fluorination. For all embodiments of the invention, $R^4$ may be aryl, aryl substituted one or more times by alkyl, heteroaryl, heteroaryl substituted one or more times by alkyl, alkyl, arylalkyl, arylalkyl substituted one or more times on its aryl part by alkyl, heteroarylalkyl, and heteroarylalkyl substituted one or more times on its heteroaryl part by alkyl, any of which may be unsubstituted or substituted one or more times by suitable substituents (advantageously not including nucleophilic groups such as primary, secondary and tertiary amino groups), for example selected from halo (particularly fluoro or chloro), cyano, carboxy, sulphoxy and nitro. In embodiments, $R^4$ is $C_1$-$C_{10}$ alkyl optionally substituted by at least one electron withdrawing group, e.g. a halogen, for example selected from F and Cl. In one embodiment, $R^4$ is alkyl having 1, 2, 3 or 4 carbon atoms, e.g. methyl, ethyl, n-propyl, isopropyl, n-butyl, sec-butyl or tert-butyl, optionally substituted by at least one electron withdrawing group, e.g. a halogen.

$R^4$ may be a group of the formula -L-$R^5$ as previously described, for example in which L is a bond and $R^5$ is optionally substituted alkyl. In one embodiment, $R^4$ is of the formula —$(CH_2)_n$—$R^5$ in which $R^5$ in particular is optionally substituted aryl. Preferably $R^4$ is methyl or chloromethyl. In another embodiment, $R^4$ is benzyl optionally substituted by one or more $R^{20}$ groups. The identity of $R^4$ is chosen independently of the identity of other substituents on the molecule.

Further Embodiments

In one embodiment, the chiral species has the structure of Formula (IV):

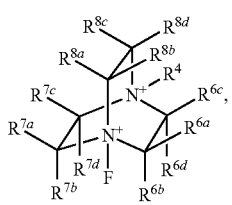

(IV)

wherein each of $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ is hydrogen or is an independently selected substituent; and for at least one pair selected from: $R^{6a}$ and $R^{6b}$; $R^{6c}$ and $R^{6d}$; $R^{7a}$ and $R^{7b}$; $R^{7c}$ and $R^{7d}$; $R^{8a}$ and $R^{8b}$; and $R^{8c}$ and $R^{8d}$, one member of that pair is different from the other member of that pair. $R^4$ is an independently selected substituent other than fluorine, for example as previously described in [0042] or [0043]. Where any of $R^{6a}$ to $R^{8d}$ is a substituent, it may be a substituent moiety as described above with reference to $R^1$, $R^2$ and $R^3$, i.e. as described in any individual one of paragraphs [0021] to [0033], e.g. in paragraph [0032]. The identities of the substituent moieties are independently selected. In one embodiment, at least one of $R^{6a}$ to $R^{8d}$ comprises a chiral centre. Thus, at least one of $R^{6a}$ to $R^{8d}$ may comprise an asymmetric carbon atom. For example, two or three of $R^{6a}$ to $R^{8d}$ may comprise an asymmetric carbon atom and be chiral.

In an embodiment, at least one of $R^{6a}$ to $R^{8d}$ comprises a chiral centre which is proximal to the DABCO scaffold, i.e. the carbon which is directly bonded to the DABCO scaffold is asymmetric. For example, two or three of $R^{6a}$ to $R^{8d}$ may comprise a chiral centre proximal to the DABCO scaffold.

In an embodiment of species of Formula (IV), therefore, each of $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ is independently selected from the group consisting of: H, aryl, heteroaryl, —(CH$_2$)$_n$-aryl and —(CH$_2$)$_n$-heteroaryl (and in particular is selected from aryl and —(CH$_2$)$_n$-aryl), wherein n is from 1 to 4, and wherein aryl and heteroaryl are optionally substituted by at least one substituent, (for example 1, 2 or 3 substituents), e.g. selected from alkoxy, halo (particularly fluoro or chloro), cyano, carboxy, sulphoxy, nitro, alkyl and alkyl substituted by at least a single $R^{20}$ group. In particular, but without limitation, the or each aryl is independently phenyl or naphthyl whilst the or each heteroaryl is independently pyridine, pyrimidine, quinoline and isoquinoline, wherein phenyl, naphthyl, pyridine, pyrimidine, quinoline and isoquinoline are independently optionally substituted by at least one substituent selected from halo (particularly fluoro or chloro), cyano, carboxy, sulphoxy, nitro halogen, alkyl and alkyl substituted by at least one substituent selected from halo (particularly fluoro or chloro), cyano, carboxy, sulphoxy and nitro. Phenyl, naphthyl, pyridine, pyrimidine, quinoline and isoquinoline are in one embodiment unsubstituted or substituted by one or more substituents (e.g. 1, 2 or 3 substituents) selected from halo (e.g. F or Cl), alkyl and alkyl substituted one or more times by halo.

The invention includes species of Formula (IV) in which each of $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ is independently selected from the group consisting of: H, and the moieties of Formulae (i)-(iv) below in which t is 0, 1, 2, 3, 4 or 5 (e.g. 0, 1 or 2), u is 0, 1, 2 or 3 (e.g. 0, 1 or 2) and v is 0, 1, 2, 3 or 4 (e.g. 0, 1 or 2), and $R^9$ and $R^{10}$ are independently selected from alkoxy (e.g. methoxy or ethoxy), halo (particularly fluoro or chloro), cyano, carboxy, sulphoxy, nitro, alkyl and alkyl substituted one or more times by halo, and optionally are selected from halo (e.g. F or Cl), alkyl and alkyl substituted one or more times by halo:

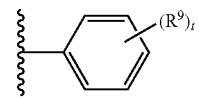

(i)

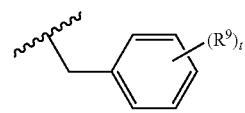

(ii)

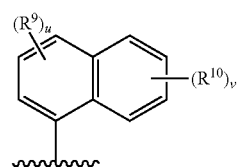

(iii)

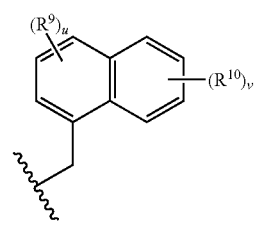

(iv)

It will be recalled, though, that for at least one pair selected from: $R^{6a}$ and $R^{6b}$; $R^{6c}$ and $R^{6d}$; $R^{7a}$ and $R^{7b}$; $R^{7c}$ and $R^{7d}$; $R^{8a}$ and $R^{8b}$; and $R^{8c}$ and $R^{8d}$, one member of that pair is different from the other member of that pair. In one embodiment, t is 0, 1 or 2, u is 0, 1 or 2 and v is 0, 1 or 2, and $R^6$ and $R^7$ are independently selected from halo (e.g. F or Cl), alkyl and alkyl substituted one or more times by halo. In one embodiment, the moieties (i) and (ii) are substituted at the 4-position, in which case t may for example be 1. Where a species of Formula (IV) has more than one substituent having the formula of a single one of moieties (i)-(iv), then the two or more said substituents are independently selected from each other but, in one embodiment, the two or more substituents are the same.

One embodiment consists of species of Formula (IV) in which each of $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ is independently selected from the group consisting of: H, and the moieties of Formulae (vii)-(xii) below, recalling though that for at least one pair selected from: $R^{6a}$ and $R^{6b}$; $R^{6c}$ and $R^{6d}$; $R^{7a}$ and $R^{7b}$; $R^{7c}$ and $R^{7d}$; $R^{8a}$ and $R^{8b}$; and $R^{8c}$ and $R^{8d}$, one member of that pair is different from the other member of that pair:

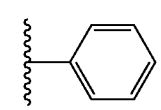

(vii)

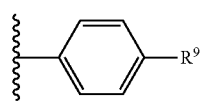

(viii)

-continued

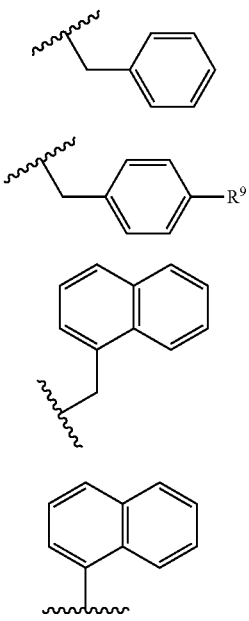

(ix)

(x)

(xi)

(xii)

Turning now to the embodiments of Formula (Ib), the above discussion of possibilities for $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ in relation to Formula (IV) is applicable equally to $R^{1a}$, $R^{1b}$, $R^{1c}$, $R^{1d}$, $R^{2a}$, $R^{2b}$, $R^{2c}$ and $R^{2d}$ of Formula (Ib).

Continuing to discuss the species of Formula (IV), the species may have the features of one or more of the following embodiments 1) to 6) and, in particular, the features of one or more of the following embodiments 1) to 4):

1) one member of the pair $R^{6a}$ and $R^{6b}$ is different from the other member of the pair;
2) one member of the pair $R^{6c}$ and $R^{6d}$ is different from the other member of the pair;
3) one member of the pair $R^{7a}$ and $R^{7b}$ is different from the other member of the pair;
4) one member of the pair $R^{7c}$ and $R^{7d}$ is different from the other member of the pair;
5) one member of the pair $R^{8a}$ and $R^{8b}$ is different from the other member of the pair;
6) one member of the pair $R^{8c}$ and $R^{8d}$ is different from the other member of the pair.

As mentioned, the species discussed in this paragraph may fall within a single one of embodiments 1) to 6) and particularly 1) to 4), or within a combination of two or more of them, for example species having a combination comprising or, in particular, consisting of the following pair of embodiments: 1) and 2); 1) and 4); 3) and 4); and 2) and 4).

Particular species of embodiments 1) to 6), for example of embodiments 1) to 4), have the features that (i) each member of $R^{6a}$ to $R^{8d}$ other than the members of the pair of that embodiment is H; and (ii) a single member of the pair of the embodiment is H. For example, species of embodiment 1) may have the feature that each member of $R^{6a}$ to $R^{8d}$ is H other than $R^{6a}$ and $R^{6b}$ and a single member of $R^{6a}$ and $R^{6b}$ is H. Similarly, species of embodiment 2) may have the feature that each member of $R^{6a}$ to $R^{8d}$ is H other than $R^{6c}$ and $R^{6d}$ and a single member of $R^{6c}$ and $R^{6d}$ is H. A species combining embodiments 1) and 2) will in this case have the features that that each member of $R^{6a}$ to $R^{8d}$ is H other than $R^{6a}$, $R^{6b}$, $R^{6c}$ and $R^{6d}$ and a single member of $R^{6a}$ and $R^{6b}$ is H and a single member of $R^{6c}$ and $R^{6d}$ is H. A species combining embodiments 3) and 4) will in this case have the features that that each member of $R^{6a}$ to $R^{8d}$ is H other than $R^{7a}$, $R^{7b}$, $R^{7c}$ and $R^{7d}$ and a single member of $R^{7a}$ and $R^{7b}$ is H and a single member of $R^{7c}$ and $R^{7d}$ is H, and so on for species having different combinations of embodiments 1)-6), e.g. 1)-4).

The invention includes an embodiment of Formula (Ib) or Formula (IV), which like all embodiments of Formula (Ib) or Formula (IV) may be combined with any compatible features previously discussed in relation to Formula (Ib) or Formula (IV), in which $R^{3a}$, $R^{3b}$, $R^{3c}$ and $R^{3d}$ are the same or, as the case may be, $R^{8a}$, $R^{8b}$, $R^{8c}$ and $R^{8d}$ are the same. In particular, all of $R^{3a}$, $R^{3b}$, $R^{3c}$, $R^{3d}$, $R^{8a}$, $R^{8b}$, $R^{8c}$ and $R^{8d}$ may be H, thus forming a chiral species of Formula (Va) and Formula (Vb):

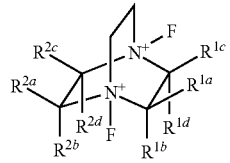
(Va)

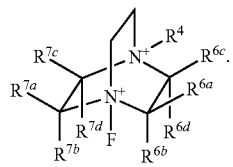
(Vb)

In a further embodiment of Formula (IV), the chiral species has the structure of Formula (VI):

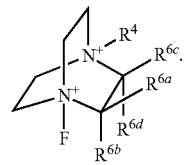
(VI)

In a sub-embodiment of Formula (VI), both members of the pair $R^{6a}$ and $R^{6d}$ are the same and both members of the pair $R^{6b}$ and $R^{6c}$ are the same. In order to make the molecule chiral, the identity of $R^{6a}$ and $R^{6d}$ is different from the identity of $R^{6b}$ and $R^{6c}$. The invention includes species in which both members of a single one of the two pairs ($R^{6a}$ & $R^{6d}$; $R^{6b}$ & $R^{6c}$) are hydrogen.

In a further embodiment of Formula (IV), the chiral species has the structure of Formula (VII):

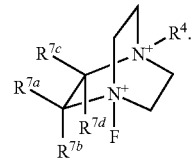
(VII)

In a sub-embodiment of Formula (VII), both members of the pair $R^{7a}$ and $R^{7d}$ are the same and both members of the pair $R^{7b}$ and $R^{7c}$ are the same. In order to make the molecule chiral, the identity of $R^{7a}$ and $R^{7d}$ is different from the identity of $R^{7b}$ and $R^{7c}$. The invention includes species in which both members of a single one of the two pairs mentioned in this paragraph are hydrogen.

In a further embodiment of Formula (IV), the chiral species has the structure of Formula (VIII):

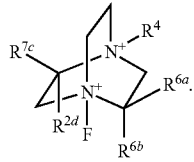
(VIII)

In a sub-embodiment of Formula (VIII), both members of the pair $R^{6a}$ and $R^{7c}$ are the same and both members of the pair $R^{6b}$ and $R^{7d}$ are the same. In order to make the molecule chiral, the identity of $R^{6a}$ and $R^{7c}$ is different from the identity of $R^{6b}$ and $R^{7d}$. The invention includes species in which both members of a single one of the two pairs mentioned in this paragraph are hydrogen.

In a further embodiment of Formula (IV), the chiral species has the structure of Formula (IX):

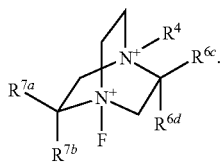
(IX)

In a sub-embodiment of Formula (IX), both members of the pair $R^{6c}$ and $R^{7a}$ are the same and both members of the pair $R^{6d}$ and $R^{7b}$ are the same. In order to make the molecule chiral, the identity of $R^{6c}$ and $R^{7a}$ is different from the identity of $R^{6d}$ and $R^{7b}$. The invention includes species in which both members of a single one of the two pairs mentioned in this paragraph are hydrogen.

The chiral species may have a structure selected from Formulae (X) to (XVII):

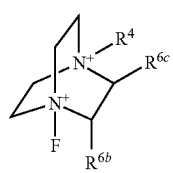
(X)

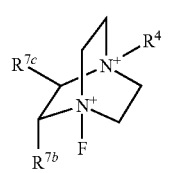
(XI)

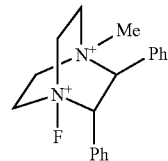
(XII)

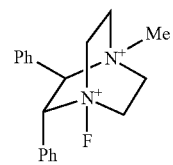
(XIII)

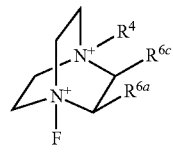
(XIV)

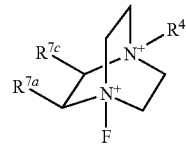
(XV)

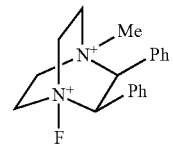
(XVI)

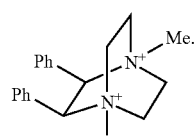
(XVII)

The chiral species may be selected from:

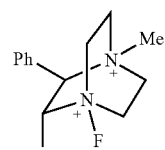
29

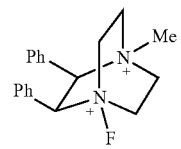
112

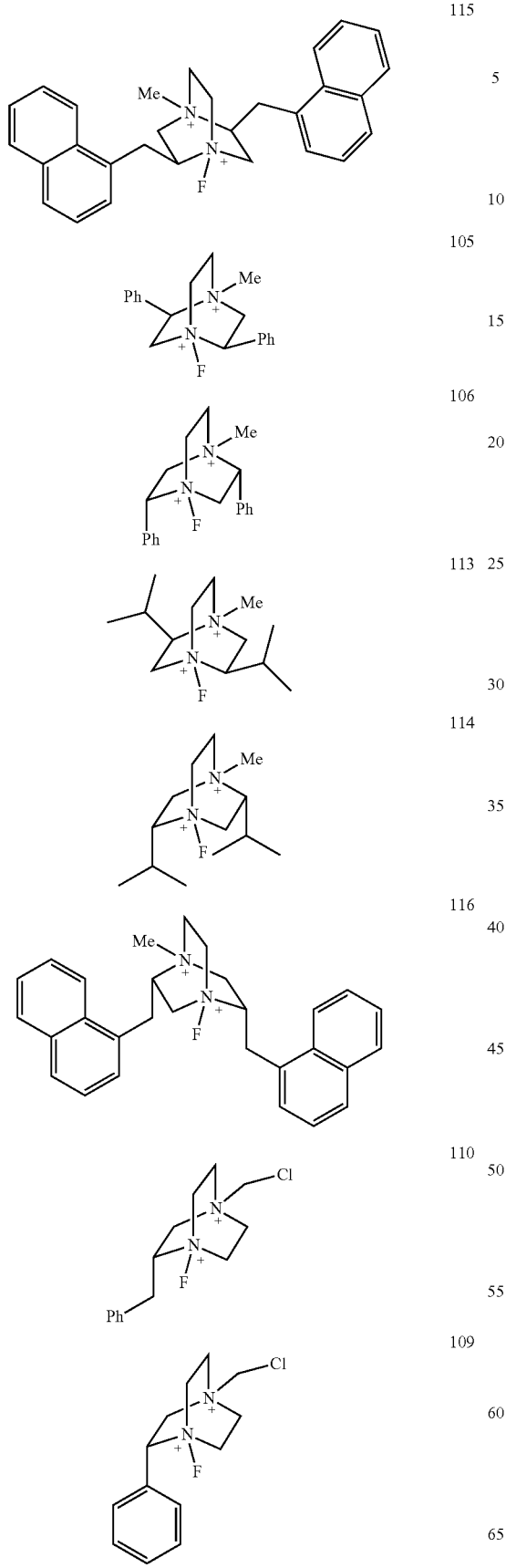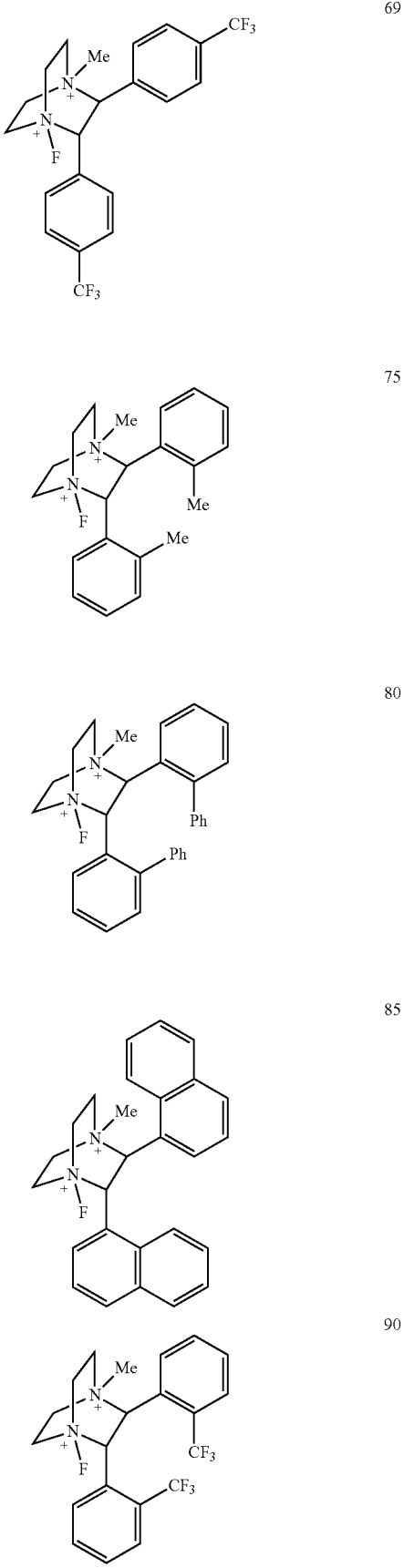

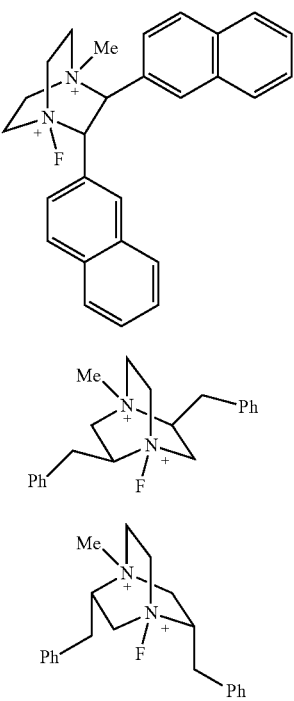

95

107

108 or an enantiomer thereof.

Chiral Substituents

For any of formulae I, II, III, Ib, Ic, Id, IV, Va, Vb, VI, VII, VIII, IX, X, XI, XIV, XV, at least one of the substituents (i.e. at least one of $R^1$, $R^2$, $R^3$, $R^{1a}$, $R^{1b}$, $R^{1c}$, $R^{1d}$, $R^{2a}$, $R^{2b}$, $R^{2c}$, $R^{2d}$, $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$) may comprise a chiral centre, e.g. an asymmetric carbon atom.

Thus, the chiral substituent comprises a carbon atom with four groups attached which are all different, wherein one of those groups comprises the DABCO scaffold and the other three are selected from individual atoms, organic groups and inorganic groups.

In compounds in which there are two or more substituents which comprise a chiral centre, the two or more substituents which comprise a chiral centre are generally selected independently of each other. In one embodiment, however, the two or more substituents which comprise a chiral centre are the same.

The chiral centre may be proximal to the DABCO scaffold, i.e. the carbon which is directly bonded to the DABCO scaffold may be asymmetric. Thus, the substituent may comprise a carbon atom directedly bonded to the DABCO scaffold, the carbon being substituted with four groups which are all different, wherein one of the groups is the directly bonded DABCO scaffold and the other three are selected from individual atoms, organic groups and inorganic groups.

The disclosures of paragraphs [0066] to [0088] may apply to any embodiment in which any one or more of $R^1$, $R^2$, $R^3$, $R^{1a}$, $R^{1b}$, $R^{1c}$, $R^{1d}$, $R^{2a}$, $R^{2b}$, $R^{2c}$, $R^{2d}$, $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ has an asymmetric carbon atom which is directly bonded to the DABCO scaffold. For the purposes of clarity, these substituents will be referred to in the following paragraphs as "proximally asymmetric substituents". The term "proximally asymmetric substituent" should be considered to refer to any one or more of $R^1$, $R^2$, $R^3$, $R^{1a}$, $R^{1b}$, $R^{1c}$, $R^{1d}$, $R^{2a}$, $R^{2b}$, $R^{2c}$, $R^{2d}$, $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ which has an asymmetric carbon atom which is directly bonded to the DABCO scaffold. In compounds in which there are two or more proximally asymmetric substituents, the two or more proximally asymmetric substituents are generally selected independently of each other. In one embodiment, however, the two or more proximally asymmetric substituents are the same.

In an embodiment, the or each proximally asymmetric substituent, selected independently of any other proximally asymmetric substituent, has the formula (XVIII):

(XVIII)

wherein $R^{11}$, $R^{12}$ and $R^{13}$ are each different and are selected from: H, and M-$R^{14}$, M is a bond or an inert linker containing 1, 2, 3, 4 or 5 in-chain atoms; and $R^{14}$ is H or a moiety having from 1 to 20 plural valent atoms, selected from heteroaryl, heteroaryl substituted with one or more $R^{20}$ groups, hydrocarbyl, hydrocarbyl substituted with one or more substituents selected from $R^{20}$ groups; wherein any one substituent $R^{14}$ is selected independently from each other $R^{14}$ and each M is selected independently from each other M, provided always that $R^{11}$, $R^{12}$ and $R^{13}$ are not the same.

In an embodiment, M has from 1-4 in-chain atoms e.g. linkers having one or two in-chain atoms. Thus, M may be a bond or an inert linker selected from alkyl, ether, amide, amine, thioether, carboxy, carbonyl. $R^{14}$ may have from 1 to 15 plural valent atoms. In an embodiment, in at least one occurrence $R^{14}$ has greater than 3 plural valent atoms, e.g. greater than 6 plural valent atoms.

The term "ether linker" includes reference to an alkyl chain in which a single —$CH_2$-group is replaced by —O—. As examples an ether linker with one in-chain atom is —O—, an ether linker with two in chain atoms may be —$CH_2$O— and it may be —O$CH_2$—, and an ether linker with three in chain atoms may be —$CH_2CH_2$O—, —O$CH_2CH_2$— or —$CH_2$O$CH_2$— etc.

The term "thioether linker" includes reference to an alkyl chain in which a single —$CH_2$-group is replaced by —S—. As examples a thioether linker with one in-chain atom is —S—, a thioether linker with two in chain atoms may be —$CH_2$S— and it may be —S$CH_2$—, and a thioether with three in chain atoms may be —$CH_2CH_2$S—, —S$CH_2CH_2$— or —$CH_2$S$CH_2$— etc.

The term "amine linker" includes reference to an alkyl chain in which a single —$CH_2$-group is replaced by —N($R_N$)—. As examples an amine linker with one in-chain atom is —N($R_N$)—, wherein $R_N$ is a substituent on the nitrogen which may be a single atom (e.g. H) and may be an organic group (e.g. hydrocarbyl). An amine linker with two in chain atoms may be —$CH_2$N($R_N$)— and it may be —N($R_N$)$CH_2$—, and an amine linker with three in chain atoms may be —$CH_2CH_2$N($R_N$)—, —N($R_N$)$CH_2CH_2$— or —$CH_2$N($R_N$)$CH_2$— etc.

In an embodiment, $R^{14}$ is a moiety having from 1 to 20 plural valent atoms, selected from heteroaryl, heteroaryl substituted with one or more $R^{20}$ groups, hydrocarbyl, hydrocarbyl substituted with one or more $R^{20}$ groups.

In an embodiment, a single one of $R^{11}$, $R^{12}$ and $R^{13}$ is H.

In an embodiment, at least one M is a bond or an alkyl linker. In a further embodiment, at least one of $R^{11}$, $R^{12}$ and $R^{13}$ is a M-$R^{14}$ group wherein M is a bond or an alkyl linker and $R^{14}$ has greater than 3 plural valent atoms, e.g. at least 6 plural valent atoms. In another embodiment, at least one M is a bond. In an embodiment, a single one of $R^{11}$, $R^{12}$ and $R^{13}$ is H and at least one M is a bond or an alkyl linker. In an embodiment, one of $R^{11}$, $R^{12}$ and $R^{13}$ is H and at least one of $R^{11}$, $R^{12}$ and $R^{13}$ is a M-$R^{14}$ group wherein M is a bond or an alkyl linker and $R^{14}$ has greater than 3 plural valent atoms, e.g. at least 6 plural valent atoms. In a specific embodiment, a single one of $R^{11}$, $R^{12}$ and $R^{13}$ is H and at least one of $R^{11}$, $R^{12}$ and $R^{13}$ is a M-$R^{14}$ group wherein M is a bond and $R^{14}$ has greater than 3 plural valent atoms, e.g. at least 6 plural valent atoms.

In an embodiment, at least one of $R^{11}$, $R^{12}$ and $R^{13}$ is a M-$R^{14}$ group wherein M is a linker selected from: ether, thioether and amine. In a further embodiment, at least one of $R^{11}$, $R^{12}$ and $R^{13}$ is a M-$R^{14}$ group wherein M is a linker selected from ether and thioether, (e.g. $M^2$ is an ether linker, for example —O—).

In an embodiment, at least one of $R^{11}$, $R^{12}$ and $R^{13}$ is a M-$R^{14}$ group wherein M is a linker selected from: ether, thioether and amine and $R^{14}$ is independently a moiety having from 1 to 20 plural valent atoms, selected from heteroaryl, heteroaryl substituted with one or more $R^{20}$ groups, hydrocarbyl, hydrocarbyl substituted with one or more $R^{20}$ groups. In a further embodiment, at least one of $R^{11}$, $R^{12}$ and $R^{13}$ is a M-$R^{14}$ group wherein M is a linker selected from ether and thioether, (e.g. $M^2$ is an ether linker, for example —O—) and $R^{14}$ is independently a moiety having from 1 to 20 plural valent atoms, selected from heteroaryl, heteroaryl substituted with one or more $R^{20}$ groups, hydrocarbyl, hydrocarbyl substituted with one or more $R^{20}$ groups.

In an embodiment, at least one of $R^{11}$, $R^{12}$ and $R^{13}$ is a M-$R^{14}$ group wherein M is a linker selected from: ether, thioether and amine and $R^{14}$ is a hydrocarbyl group. In a further embodiment, at least one of $R^{11}$, $R^{12}$ and $R^{13}$ is a M-$R^{14}$ group wherein M is a linker selected from ether and thioether (e.g. $M^2$ is an ether linker, for example —O—) and $R^{14}$ is a hydrocarbyl group optionally substituted with one or more $R^{20}$ groups. In an embodiment, at least one of $R^{11}$, $R^{12}$ and $R^{13}$ is a M-$R^{14}$ group wherein M is a linker selected from: ether, thiophenyl and amine and $R^{14}$ is an aryl or heteroaryl group optionally substituted with one or more $R^{20}$ groups. In a further embodiment, at least one of $R^{11}$, $R^{12}$ and $R^{13}$ is a M-$R^{14}$ group wherein M is a linker selected from ether and thioether (e.g. $M^2$ is an ether linker, for example —O—) and $R^{14}$ is an aryl or heteroaryl group optionally substituted with one or more $R^{20}$ groups.

In another embodiment, at least one of $R^{11}$, $R^{12}$ and $R^{13}$ is a M-$R^{14}$ group wherein M is a linker selected from: ether, thioether and amine and $R^{14}$ is H. In a further embodiment, at least one of $R^{11}$, $R^{12}$ and $R^{13}$ is a M-$R^{14}$ group wherein M is a linker selected from ether and thioether (e.g. $M^2$ is an ether linker, for example —O—) and $R^{14}$ is H.

In a preferred embodiment, at least one of $R^{11}$, $R^{12}$ and $R^{13}$ is a M-$R^{14}$ group wherein M is a linker selected from: ether, thiophenyl and amine and $R^{14}$ is an aryl group optionally substituted with one or more $R^{20}$ groups. In a further embodiment, at least one of $R^{11}$, $R^{12}$ and $R^{13}$ is a M-$R^{14}$ group wherein M is a linker selected from ether and thioether (e.g. $M^2$ is an ether linker, for example —O—) and $R^{14}$ is an aryl group optionally substituted with one or more $R^{20}$ groups.

In an embodiment, a single one of $R^{11}$, $R^{12}$ and $R^{13}$ is H; a single one of $R^{11}$, $R^{12}$ and $R^{13}$ is a $M^1$-$R^{14a}$ group wherein $M^1$ is a bond or an alkyl linker; and a single one of $R^{11}$, $R^{12}$ and $R^{13}$ is a $M^2$-$R^{14b}$ wherein $M^2$ is a linker selected from: ether, thioether and amine and $R^{14b}$ is independently a moiety having from 1 to 20 plural valent atoms, selected from heteroaryl, heteroaryl substituted with one or more $R^{20}$ groups, hydrocarbyl, hydrocarbyl substituted with one or more $R^{20}$ groups In an embodiment, the or each proximally asymmetric substituent, selected independently of any other proximally asymmetric substituent, has the formula (XIX) or (XX):

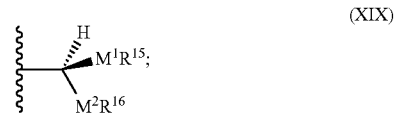

wherein $M^1$ is a bond or an alkyl linker,
$M^2$ is a linker selected from: ether, thioether and amine,
$R^{15}$ and $R^{16}$ are independently H or a moiety having from 1 to 20 plural valent atoms (e.g. from 1 to 15), selected from heteroaryl, heteroaryl substituted with one or more $R^{20}$ groups, hydrocarbyl, hydrocarbyl substituted with one or more $R^{20}$ groups;
provided that if $M^1$ is a bond, $R^{15}$ is not H.

In an embodiment, $M^1$ is a bond or an alkyl linker having from 1-4 in-chain atoms e.g. alkyl linkers having one or two in-chain atoms.

In an embodiment, $M^2$ is a linker having from 1-4 in-chain atoms e.g. ether, thioether and amine linkers having one or two in-chain atoms.

In an embodiment, $R^{16}$ is H. In an alternative embodiment, $R^{16}$ is an aryl group, optionally substituted with one or more $R^{20}$ groups. In an embodiment, $R^{16}$ is a phenyl group, optionally substituted with one or more $R^{20}$ groups. In an alternative embodiment, $R^{16}$ is a napthyl group, optionally substituted with one or more $R^{20}$ groups.

In an embodiment, $M^2$ is a linker selected from ether and thioether (e.g. $M^2$ is an ether linker, for example —O—). In a specific embodiment, $R^{16}$ is aryl, optionally substituted with one or more $R^{20}$ groups and $M^2$ is a linker selected from ether and thioether (e.g. $M^2$ is an ether linker, for example —O—). In an embodiment, $R^{16}$ is a phenyl group, optionally substituted with one or more $R^{20}$ groups and $M^2$ is a linker selected from ether and thioether (e.g. $M^2$ is an ether linker, for example —O—). In an alternative embodiment, $R^{16}$ is a napthyl group, optionally substituted with one or more $R^{20}$ groups and $M^2$ is a linker selected from ether and thioether (e.g. $M^2$ is an ether linker, for example —O—).

In an embodiment, $M^1$ is a bond. In an embodiment, $R^{15}$ is a hydrocarbyl group. In an embodiment, $R^{15}$ is a hydrocarbyl group having greater than 3 plural valent atoms, e.g. at least 6 plural valent atoms. In an embodiment, $R^{15}$ is an aryl group (e.g. a phenyl group or a naphthyl group) optionally substituted with one or more $R^{20}$ groups. In an alternative embodiment, $R^{15}$ is an alkyl group (e.g. an iso-propyl or tert-butyl group) optionally substituted with one or more $R^{20}$ groups. In a specific embodiment, $M^1$ is a bond and $R^{15}$ is a hydrocarbyl group optionally substituted with one or more $R^{20}$ groups. In an embodiment, $M^1$ is a bond and $R^{15}$ is a hydrocarbyl group optionally substituted with one or more $R^{20}$ groups and having greater than 3 plural valent atoms, e.g. at least 6 plural valent atoms. In an embodiment, $M^1$ is a bond and $R^{15}$ is an aryl group (e.g. a phenyl group or a naphthyl group) optionally substituted with one or more $R^{20}$ groups. In an alternative embodiment, $M^1$ is a bond and $R^{15}$ is an alkyl group (e.g. an iso-propyl or tert-butyl group) optionally substituted with one or more $R^{20}$ groups.

In an embodiment, the or each proximally asymmetric substituent, selected independently of any other proximally asymmetric substituent, has the formula (XXI) or (XXII):

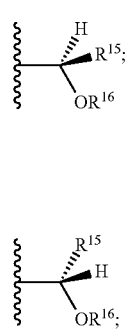

wherein $R^{15}$ and $R^{16}$ are independently H or a moiety having from 1 to 20 plural valent atoms, selected from heteroaryl, heteroaryl substituted with one or more $R^{20}$ groups, hydrocarbyl, hydrocarbyl substituted with one or more $R^{20}$ groups.

In an embodiment, $R^{15}$ is a hydrocarbyl group optionally substituted with one or more $R^{20}$ groups. In an embodiment, $R^{15}$ is a hydrocarbyl group optionally substituted with one or more $R^{20}$ groups and having greater than 3 plural valent atoms, e.g. at least 6 plural valent atoms. In an embodiment, $R^{15}$ is an aryl group (e.g. a phenyl group or a naphthyl group) optionally substituted with one or more $R^{20}$ groups. In an alternative embodiment, $R^{15}$ is an alkyl group (e.g. an iso-propyl or tert-butyl group) optionally substituted with one or more $R^{20}$ groups.

In an embodiment, $R^{16}$ is H. In an alternative embodiment, $R^{16}$ is an aryl group, optionally substituted with one or more $R^{20}$ groups. In an embodiment, $R^{16}$ is a phenyl group, optionally substituted with one or more $R^{20}$ groups. In an alternative embodiment, $R^{16}$ is a napthyl group, optionally substituted with one or more $R^{20}$ groups.

Thus, in an embodiment, the non racemic chiral species has the structure (XXIII) or that of its enantiomer:

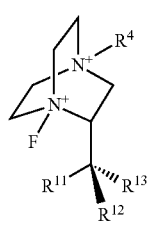

wherein $R^4$, $R^{11}$, $R^{12}$ and $R^{13}$ are as described elsewhere herein.

In an embodiment, the non-racemic chiral species has a structure selected from (XXIV) and (XV) or that of their enantiomers:

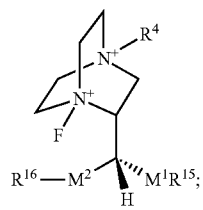

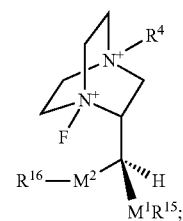

wherein $R^4$, $M^1$, $M^2$, $R^{15}$, and $R^{16}$ are as described elsewhere herein.

In an embodiment, the non-racemic chiral species has the structure (XV) or that of its enantiomer.

In an embodiment, the non-racemic chiral species has a structure selected from (XXVI) and (XXVII) or that of their enantiomers:

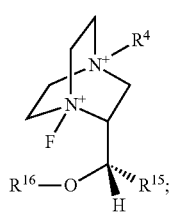

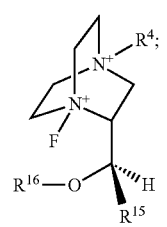

wherein $R^4$, $R^{15}$ and $R^{16}$ are as described elsewhere herein.

In an embodiment, the non-racemic chiral species has the structure (XVII) or that of its enantiomer.

In any of the above embodiments, a hydrocarbyl group may be selected from alkyl and aryl optionally substituted with one or more $R^{20}$ groups.

In an embodiment, the non-racemic chiral species has a structure selected from:

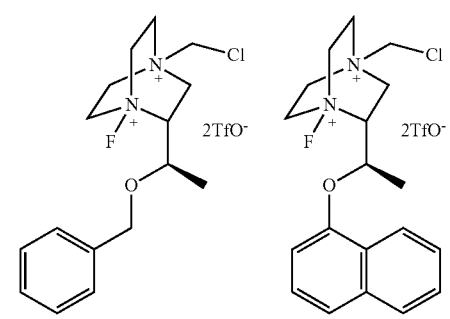
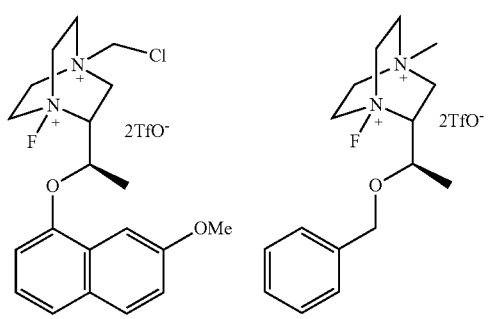
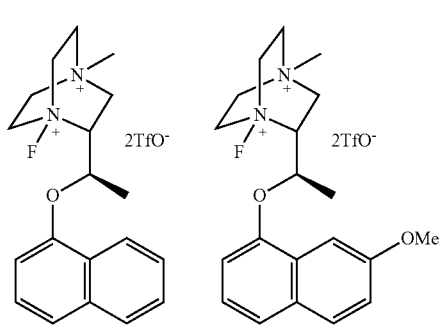
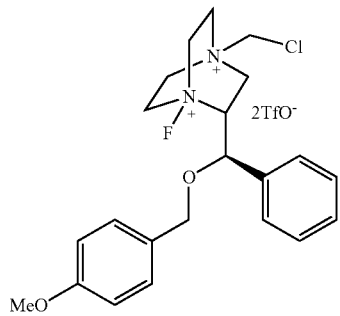
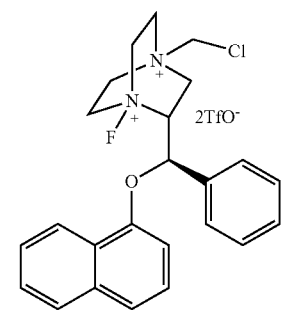
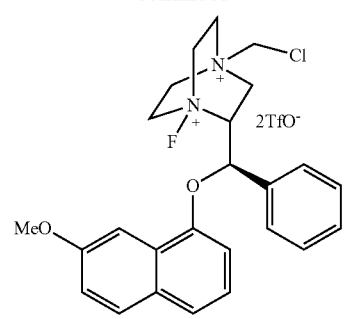
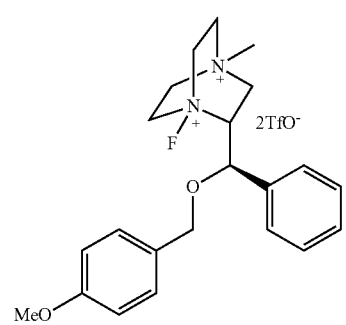
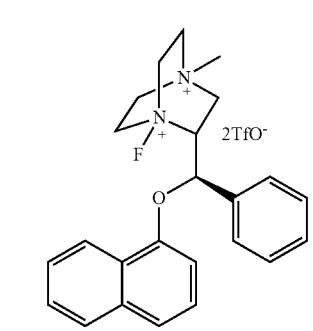
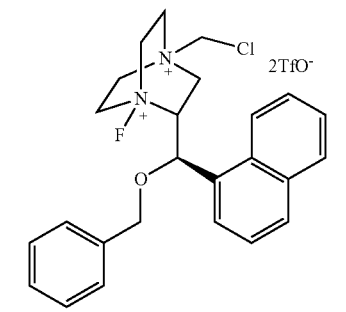
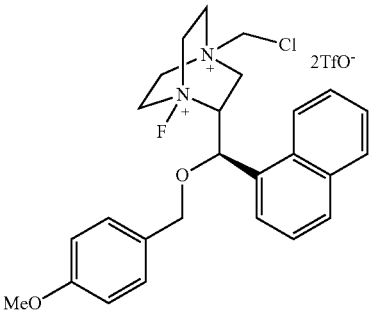

-continued

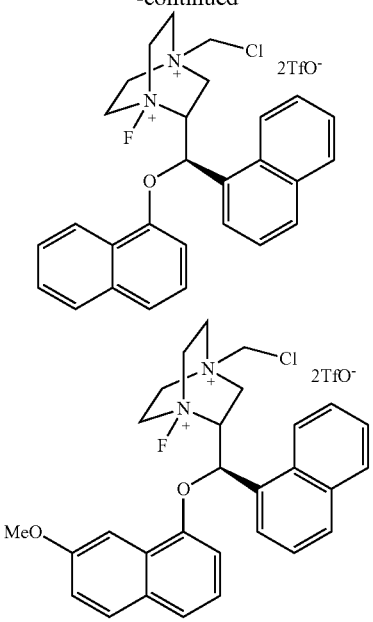

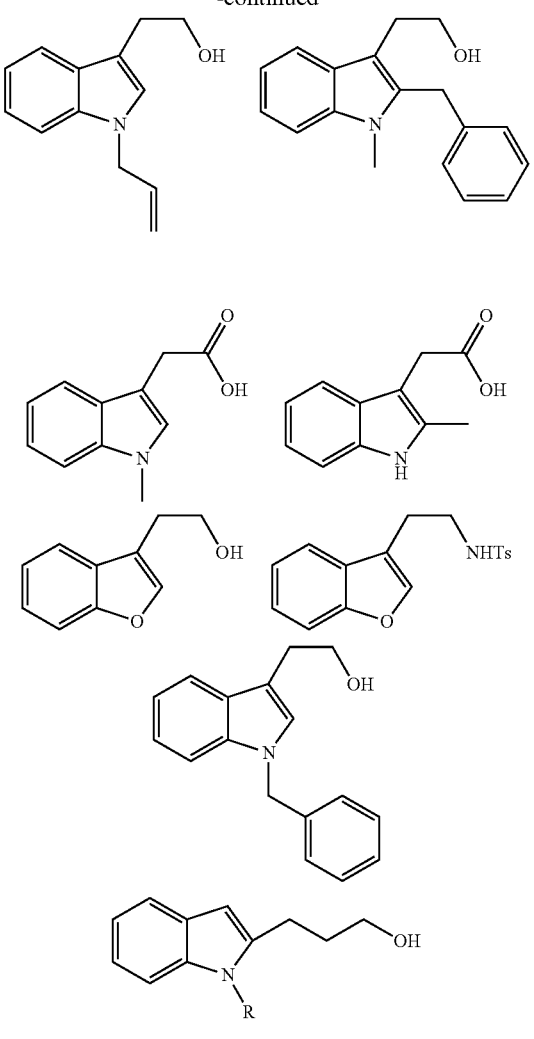

Use

The fluorinating reagents of the invention may be used in manner known per se as electrophilic fluorinating agents (see for example R E Banks et al., *J. Am. Chem. Soc.* Perkin Trans. I, 1988, 2805). Suitable substrates include, for example, those having the following structures, which are merely exemplary substrates for the guidance of the skilled reader as to illustrative members of each substrate class and are by no means limiting as to potential substrate compounds or as to classes of potential substrate compounds:

Fluorodesilylation Substrates

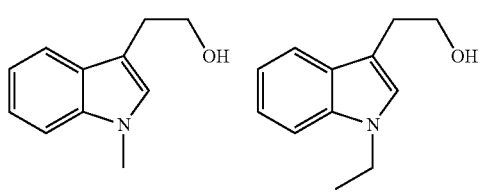

n = 1 or 2

X = CH$_2$, R = Bn
X = CH$_2$, R = p-MeBn
X = CH$_2$, R = o-MeOBn
X = CH$_2$, R = 2-naphtylmethyl
X = O, R = Bn
X = O, R = p-MeBn
X = O, R = p-ClBn
X = O, R = Et n = 1 or 2

R$^1$ = H, R$^2$ = Me, R$^3$ = Me, R$^4$ = Ph
R$^1$ = H, R$^2$ = Ph, R$^3$ = Ph, R$^4$ = Ph
R$^1$ = H, R$^2$ = Me, R$^3$ = Me, R$^4$ = Me
R$^1$ = Me, R$^2$ = Me, R$^3$ = Me, R$^4$ = Me
R$^1$ = Bn, R$^2$ = Me, R$^3$ = Me, R$^4$ = Me

Fluorocyclisation Substrates

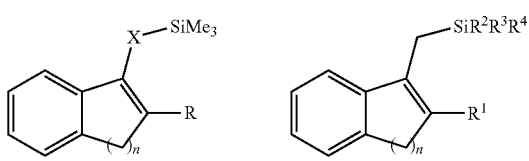

Cyano Ester Substrates

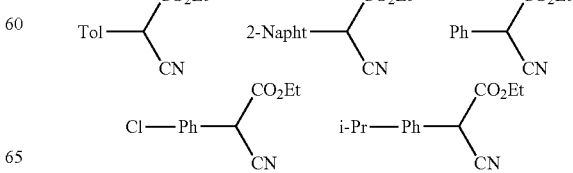

Ketone and Keto Ester Substrates

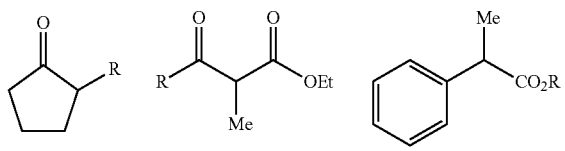

R = CO₂Et,    R = Me        R = Me
R = CO₂Bn    R = Ph        R = Et

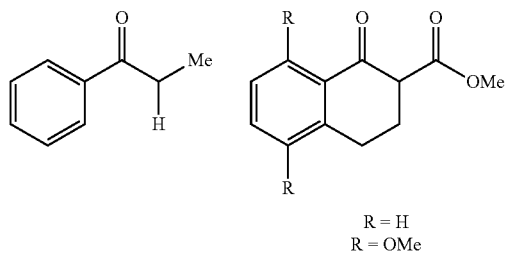

R = H
R = OMe

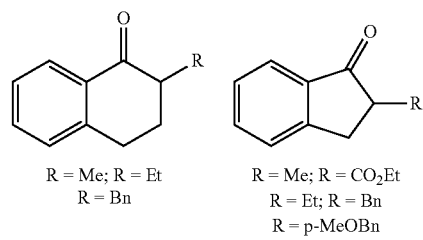

R = Me; R = Et          R = Me; R = CO₂Et
R = Bn                  R = Et; R = Bn
                        R = p-MeOBn

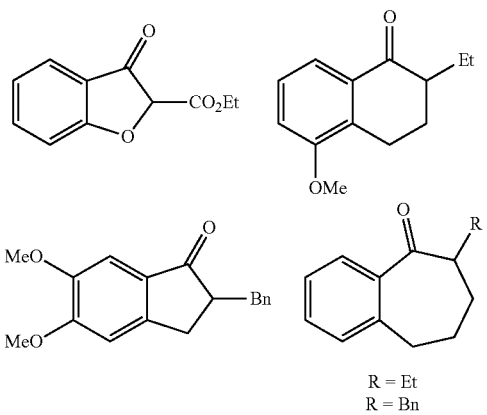

R = Et
R = Bn

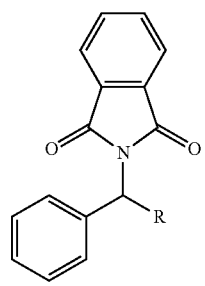

R = CO₂Et
R = CN

Oxindole Substrates

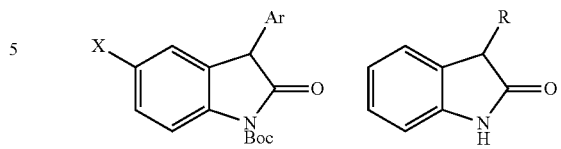

X = H, Ar = Ph              R = Bn
X = H, Ar = p-Tol           R = p-MeOBn
X = Me, Ar = p-Tol          R = Me
X = OMe, Ar = p-Tol         R = Et
X = OMe, Ar = p-FC₆H₄       R = i-Pr
                            R = CO₂Et

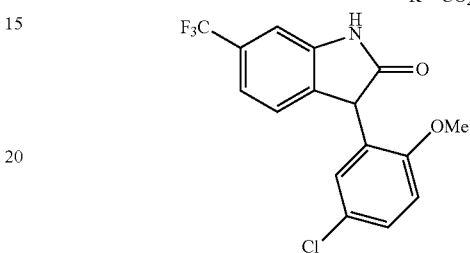

Dipeptide Substrates

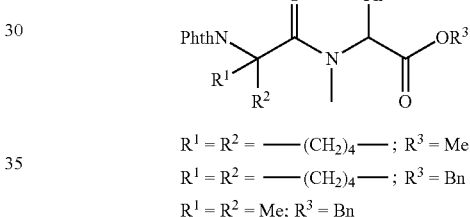

R¹ = R² = ——(CH₂)₄——; R³ = Me
R¹ = R² = ——(CH₂)₄——; R³ = Bn
R¹ = R² = Me; R³ = Bn

Different agents of the invention will have varying respective reactivities towards different substrates. Accordingly, a library comprising two or more species of the invention will provide a choice of reagents to use with different substrates. The invention includes a library comprising salts of a plurality of species of the invention, e.g. 10, 50, 100, 200 or more species. Each salt comprises a single species of the invention (disregarding possible trace contamination) and a counter-ion selected independently of the counter-ions of the other salts of the library. Each salt is contained in an individual container.

The chiral fluorinating agents of the invention may be used in the enantioselective fluorination of substrates. The substrate may be fluorinated by: (i) deprotonating the substrate with a base, e.g. LiHMDS, at low temperature, e.g. from −78° C. to room temperature, and (ii) reacting the deprotonated substrate with a fluorinating agent of Formula Ia or Ib. The fluorinating agent of Formula Ia or Ib may be pre-prepared fluorinating reagent or it may be prepared in situ, i.e. by the reaction of a compound of Formula II or III with a fluorinating agent, e.g. Selectfluor. The resulting enantiomeric excess of the fluorinated substrate is in part dependent on the chiral fluorinating agent used.

Fluorinated organic compounds made using the fluorinating agents of the invention and pharmaceutical or other compositions containing them, may contain a detectable amount of a species of the invention. Such compositions are included in the invention.

Synthesis

The chiral species of Formula Ia may be produced via the synthetic route as illustrated generally in the figure below:

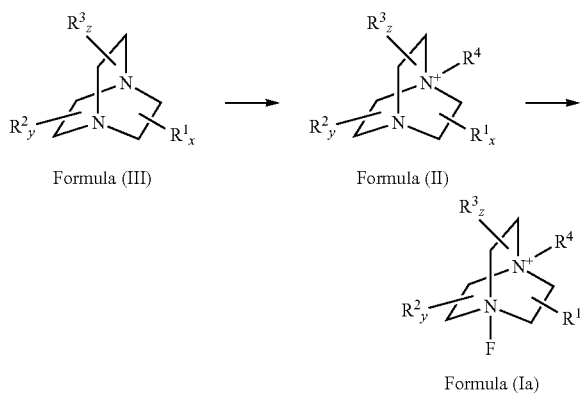

Formula (III)   Formula (II)

Formula (Ia)

Thus, the compound of Formula III is first quaternised to a quaternary ammonium species of Formula II, $R^4$ being a moiety which quaternises nitrogen. The quaternary ammonium species of Formula II is then fluorinated to the species of Formula Ia.

The quaternisation of the compound of Formula III may be effected by reacting the compound of Formula III with $R^4$—Z, wherein $R^4$ is a substituent and Z is a leaving group. $R^4$ may be as previously described and is in particular an alkyl group. In one embodiment, Z is a halide other than $F^-$, e.g. $Cl^-$, $Br^-$ or $I^-$, a sulfonate, e.g. tosylate, mesylate, a fluoroalkyl sulfonate ester, for example nonaflate or triflate, or fluorosulfonate. Suitably, the quaternisation is carried out in a non-polar or slightly polar solvent, for example diethyl ether The fluorination of the quaternary ammonium species of Formula II to the species of Formula Ia may be effected by reacting the species of Formula II with an electrophilic fluorinating agent, preferably fluorine. Alternatively, the electrophilic fluorinating agent may be Selectfluor, for example. The fluorine may be provided as a mixture of fluorine gas and an inert gas, e.g. nitrogen gas, preferably 10% $F_2/N_2$. In an embodiment, the species of Formula (II) is in a polar aprotic solvent (e.g. acetonitrile, DMF or DMSO) and the fluorination is carried out in the presence of a suitable counterion to form a salt with the species of Formula (III), the counterion being associated with a cation which forms a fluoride salt insoluble in the reaction medium. For example the fluorination may be carried out in the presence of NaOTf in solution.

The method for producing the compound of Formula III is dependent on the desired structure of the compound of Formula III. The synthesis of intermediates of Formula (III) may be carried out using approaches which follow procedures in the literature, for example Jung E and Rohloff J C, J. Org. Chem. 1985, 50, 4909-4913; Donkor I O and Sanders, L M, Bioorg. Med. Chem. Lett. 2001, 11, 2647-2649; Oi R and Sharpless K B, Tetrahedron Lett. 1991, 32, 4853-4854 and Oishi T and Hirama M, Tetrahedron Lett 1992, 33, 639.

The skilled person would easily recognise and select a suitable method for the preparation of the desired compound of formula III. Provided below are three general methods for producing the compounds of Formula III:

Method A—One or Two Substituents on One Ethane Bridge

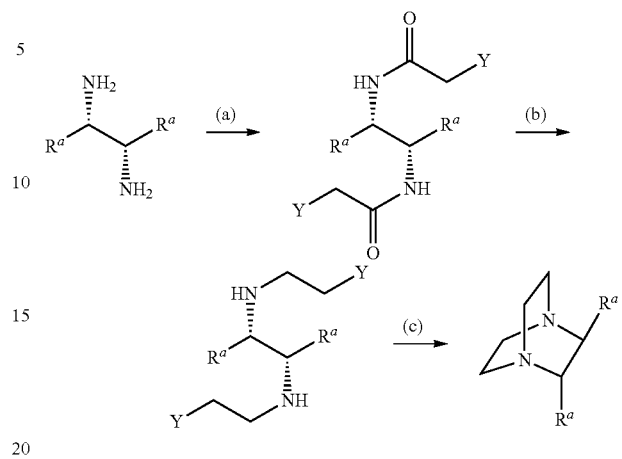

In the above reaction scheme, $R^a$ designates H or a moiety selected from those previously described as possibilities for substituents on carbon atoms of the DABCO scaffold, e.g. in paragraphs [0024] to [0041], [0045], to [0088]. As illustrated above, in method A, a diamine is first acylated with, for example, an acyl chloride (e.g. chloroacetyl chloride) to afford a diamide compound (step (a)). The diamide compound is then reduced to diamine compound (step (b)). The resulting diamine compound is then cyclised to the DABCO compound of Formula III (step (c)). The configuration of the resulting DABCO compound is dependent on the configuration of the initial diamine.

Y is a leaving group. Y may be a halide (such as Cl, Br, I), a sulfonate (mesylate, triflate, tosylate) or it may be any other group which can be displaced by a secondary amine in a nucleophillic substitution reaction.

The initial acylation step (a) is generally carried out in the presence of a base, for example triethylamine. The acylation step (a) is generally carried out in the presence of a nucleophilic catalyst, for example 4-dimethylaminopyridine (DMAP). The acylation step (a) is suitably carried out in an aprotic solvent, for example dichloromethane.

The reduction step (b) is suitably carried out using a mild reducing agent such as borane tetrahydrofuran in an aprotic solvent, for example tetrahydrofuran. The cyclisation step (c) may be carried out by heating the diamine, for example to a temperature between 100° C. and 200° C., in a polar solvent, for example dimethylformamide.

Method B—One or Two Substituents on One an Ethane Bridge

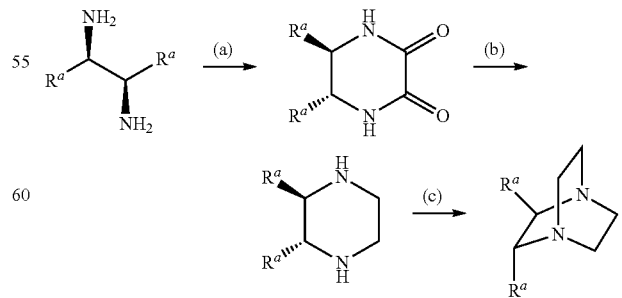

In the above reaction scheme, $R^a$ designates H or a moiety selected from those previously described as possibilities for substituents on carbon atoms of the DABCO scaffold, e.g. in paragraphs in paragraphs [0024] to [0041], [0045], to [0088]. As illustrated above, in method B, a diamine is first acylated with oxalic acid or an activated oxalic acid, for example an oxalate di-ester such as e.g. diethyl oxalate, to afford a piperazine-2,3-dione compound (step (a)). The acylation is suitably carried out at an elevated temperature in toluene. The piperazine-2,3-dione compound is then reduced to a piperazine compound (step (b)). The reduction step may be carried out in THF at a temperature of from 50° C. to 90° C., e.g. 70° C. The reducing agent may be any reducing agent, e.g. LiAlH$_4$, DIBAL-H, BH$_3$. The resulting piperazine compound is di-N-alkylated to form the DABCO compound of Formula III (step (c)). The di-N-alkylation step (c) may carried out by reacting the piperazine compound with an alkane (ethane in the illustrated embodiment) which is 1,2-disubstituted with Br or another leaving group (e.g. the disubstituted alkane is 1,2-dibromoethane). The di-N-alkylation reaction is suitably carried out in the presence of a base, for example triethylamine.

Method C—One or Two Ethane Bridges Substituted

HBTU in the presence of DIPEA at room temperature for two hours. The dipeptide may be cyclised by firstly removing the amine protecting group (denoted P$^1$). The deprotected dipeptide can then be cyclised by heating the dipeptide in a polar solvent, e.g. sec-butanol and toluene. The subsequent the reduction step is carried out using a mild reducing agent such as borane tetrahydrofuran. The reduction may additionally further comprise treating the reduction intermediate with a palladium/carbon catalyst, e.g in methanol and tetrahydrofuran.

The final products produced by following Method C comprise compounds of Formulae (VIII) and (IX), in particular those in which each ethane bridge has a single substituent. Where the C—H hydrogen of the starting amino acid is replaced by a substituent, each ethane bridge will have two substituents, i.e. all the "R" groups shown in Formulae (VIII) and (IX) are substituents. It will be appreciated that these compounds may, therefore, be synthesised from natural and/or unnatural amino acids, and that it is possible to choose the end product enantiomer by selecting the enantiomer of the amino acid starting material. As will

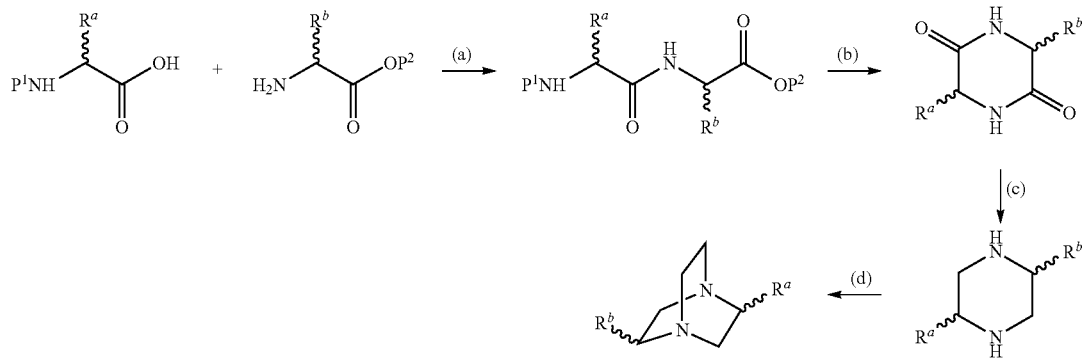

In the above reaction scheme, R$^a$ and R$^b$ each designate a moiety selected from those previously described as possibilities for substituents on carbon atoms of the DABCO scaffold, e.g. in paragraphs [0024] to [0041], [0045], to [0088]. Typically, R$^a$ and R$^b$ are the same and, where they are different, a mixture of end products may obtained and may then be separated by conventional means, e.g. chromatography, crystallisation. P$^1$ is an amino protecting group (e.g. benzyl, para-methoxy benzyl, tert-butyl carbonate, benzyl carbonate, tosylate, allyl etc.) and P$^2$ is a carboxy protecting group (benzyl, e.g. benzyl, pMeO-benzyl; silyl e.g. TBS, TBDPS, TES, TIPS; acetate etc.). The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

As illustrated above, in method C, two amino acids form a dipeptide (step (a)). The dipeptide is then cyclised to form a piperazine-2,5-dione compound (step (b)). The piperazine-2,5-dione compound is then reduced to a piperazine compound (step (c)), following the method described above in relation to Method B. The resulting piperazine compound is then di-N-alkylation to a DABCO compound of Formula III (step (d)).

The formation of the dipeptide can be effected using conventional peptide coupling conditions and reagents. For example, the protected amino acids can be coupled using be apparent from the above synthesis, it is most practical for both substituted bridges to be derived from the same amino acid, i.e have the same substituents.

Where glycine is chosen as one of two amino acids from which the chiral fluorinating agent is made, the fluorinating agent has a single substituent derived from the side chain of the other amino acid, e.g.

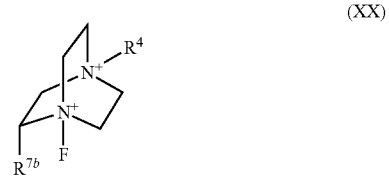

(XX)

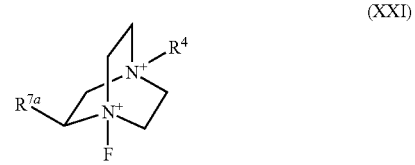

(XXI)

-continued (XXII)

(XXIII)

It will be appreciated from the aforegoing that exemplary intermediates are of the following formulae:

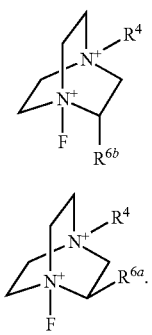

Method D—Preparation of Diamine Compounds with Multiple Chiral Centres

Compounds of formula III in which the DABCO scaffold is substituted with a substituent bearing a chiral centre proximal to the can be prepared using any of methods A to C. In the case of method C it is necessary to provide as one of the starting materials, an amino acid with two chiral centres. In the case of methods A and B, it is necessary to provide a diamine with two chiral centres. Such diamine starting materials can be prepared from amino acid derivatives with two chiral centres according to method D, exemplified in the scheme below:

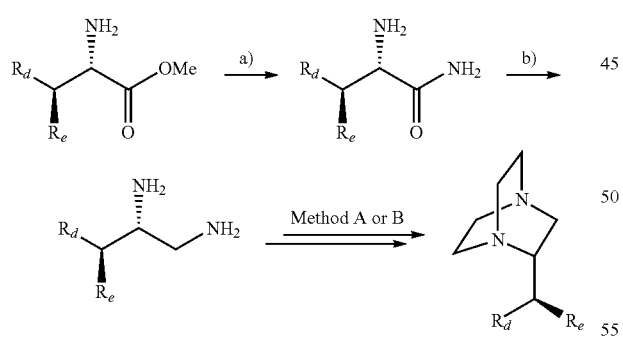

Method D comprises the conversion of an ester derivative (illustrated above as a methyl ester, but it could be an suitable ester) to an amide (step a)). This can be achieved using ammonia (which can conveniently be prepared in situ from ammonium hydroxide and a base such as a bicarbonate or carbonate, e.g. $NaHCO_3$). Reduction of the amide to an amine (step b)) can be achieved using reducing agents familiar to those in the art (e.g. $BH_3$, $LiAlH_4$). Thus method D provides a diamine which can be used as the starting material in either method A or method B.

EXAMPLES

Example 1

(1R,2R)—N,N'-(1,2-Diphenylethane-1,2-diyl)bis(2-chloroacetamide) 1

To a solution of (R,R)-1,2-diphenylethylenediamine (1.00 g, 4.71 mmol, 1 eq.), DMAP (20 mg, 0.16 mmol, 0.03 eq.) and $NEt_3$ (3.2 mL, 23.50 mmol, 5 eq.) in DCM (40 mL) chloroacetyl chloride (1.60 g, 14.13 mmol, 3 eq.) was added dropwise at 5° C. and the solution stirred at it for 3 h. Water was added and the aq. layer made acidic using 1M HCl. The product was extracted into DCM, and concentrated in vacuo to give a brown solid (1.69 g, 98%). $^1$H NMR (400 MHz, DMSO) δ: 9.03-9.01 (m, 2H, NH), 7.20-7.14 (m, 10H, ArH), 5.19-5.17 (m, 2H, H), 4.06 (s, 4H, H). $^{13}$C NMR (100.6 MHz, DMSO) δ: 166.4 (C), 140.5 (C), 128.8 (CH), 128.8 (CH), 128.3 (CH), 128.3 (CH), 128.0 (CH), 58.3 (CH), 46.4 ($CH_2$). MS–EI m/z 283.1 (7), 336.1 (10), 363.1 (M⁻, 90). IR (v, $cm^{-1}$): 3291 (NH), 1959 (NC=O), 1887 (NC=O). The α-value was not determined at this stage as the compound was used without further purification.

Example 2

N,N'-((1S,2S)-1,2-Bis(4-(trifluoromethyl)phenyl)ethane-1,2-diyl)bis(2-chloroacetamide) 2

2 was obtained from (1S,2S)-1,2-bis(4-(trifluoromethyl)phenyl)-ethane-1,2-diamine (420 mg, 1.21 mmol, 1 eq.) according to the procedure of Example 1 as a light brown solid (628 mg, 97%). $^1$H NMR (400 MHz, DMSO) δ: 9.36-9.34 (d, J=7.6 Hz, 2H, NH), 7.64-7.62 (d, J=8.1 Hz, 4H, Hc), 7.57-7.54 (d, J=8.1 Hz, 4H, H), 5.41-5.39 (d, J=7.1 Hz, 2H, H), 4.08 (s, 4H, H). $^{13}$C NMR (100.6 MHz, DMSO) δ: 166.7 (C), 145.0 (C), 129.0 (CH), 128.7 (d, J=32.0 Hz, C b), 125.8 (q, J=4.0 Hz, CH c), 125.0 (q, J=271.6 Hz, C), 57.5 (CH), 46.4 ($CH_2$). $^{19}$F NMR (376 MHz, DMSO) δ: −60.9. HRMS required for $C_{20}H_{16}Cl_2F_6N_2O_2$ ([M+Na]⁺) 523.0385, found 523.0391. IR (v, $cm^{-1}$): 3302 (NH), 3060 (NH), 1650 (NCO). MP=274-278° C. The optical rotation could not be determined due to problems with solubility.

Example 3

(R,R)-2,3-Diphenyl-1,4-diazabicyclo[2.2.2]octane 3a

To a solution of (1R,2R)—N,N'-(1,2-diphenylethane-1,2-diyl)bis(2-chloroacetamide) 1 (220 mg, 0.60 mmol, 1 eq.) in THF (8 mL) $BH_3$.THF (1 M solution in THF, 2.4 mL, 2.40 mmol, 4 eq.) was added dropwise at 0° C. and the solution was heated to reflux for 12 h. MeOH was added at 0° C. to quench any excess of $BH_3$ and the reaction mixture was concentrated in vacuo. 5% aq. HCl and DCM were added, and the organic layer was discarded. The aq. layer was made basic with 3M aq. NaOH and extracted into DCM. The combined organic extracts were dried, filtered, and concentrated in vacuo to give a yellow oil.

The N,N'-Bis(2-chloroethyl)-1,2-diphenylethane-1,2-diamine (4) (2.85 g, 8.45 mmol) was dissolved in DMF (36 mL) and refluxed for 5 h followed by solvent removal in vacuo. The crude product was dissolved in $H_2O$ and the solution brought to pH 10 using 3M aq. NaOH. The product was extracted into DCM (×3) and the combined organic extracts were washed with brine, dried, and concentrated in vacuo. The crude product was purified by flash column chromatography (CHCl$_3$:MeOH 97:3) to give a brown oil (1.45 g, 54% over two steps). (R,R)-21 (42% yield over three steps, R$_f$=0.34 (CHCl$_3$:MeOH 95:5)): $^1$H NMR (400 MHz, CDCl$_3$) δ: 7.48-7.27 (m, 10H, ArH), 4.18 (s, 2H, H), 3.04-2.99 (m, 4H, H), 2.83-2.76 (m, 2H, H), 2.64-2.59 (m, 2H, H). $^{13}$C NMR (100.6 MHz, CDCl$_3$) δ: 141.2 (C), 128.4 (CH), 128.4 (CH), 127.7 (CH), 127.7 (CH), 127.1 (CH), 62.4 (CH), 49.5 (CH$_2$), 41.1 (CH$_2$). MS–EI m/z 251.2 (5), 265.2 (M$^+$, 100). [α]$^{25}_D$=−94.8 (c 0.9, MeOH); lit. (R. Oi, B. Sharpless, *Tetrahedron Letters* 1991, 32, 4853) for (S,S)-21 [α]$_{25}^D$=+93.1 (c 4.34, MeOH).

Example 4

(S,S)-2,3-Bis(4-(trifluoromethyl)phenyl)-1,4-diazabicyclo[2.2.2]octane 5

(1S,2S)—N,N'-Bis(2-chloroethyl)-1,2-bis(4-(trifluoromethyl)phenypethane-1,2-diamine (6) was prepared from (S,S)-2 (600 mg, 1.13 mmol; see Example 2) according to the procedure of Example 3. The crude product (200 mg) was not fully isolated but directly employed in the cyclisation as stated below.

Following the same procedure as Example 3, the target compound was obtained from crude (S,S)-6 (200 mg, 0.42 mmol) as a brown oil (R$_f$=0.55 (CHCl$_3$:MeOH 95:5), 83 mg, 17% yield over two steps). $^1$H NMR (400 MHz, CDCl$_3$) δ: 7.64-7.62 (d, J=8.4 Hz, 4H, H), 7.58-7.56 (d, J=8.4 Hz, 4H, Hd), 4.14 (s, 2H, H), 3.02-2.98 (m, 4H, H), 2.73-2.61 (m, 4H, H). $^{13}$C NMR (100.6 MHz, CDCl$_3$) δ: 145.0 (C), 129.6 (q, J=32.6 Hz, C), 128.0 (CH), 125.3 (q, J=4.0 Hz, CH), 124.1 (q, J=272.4 Hz, C), 62.1 (CH), 49.4 (CH$_2$), 41.2 (CH$_2$). $^{19}$F NMR (376 MHz, CDCl$_3$) δ: −62.5. HRMS required for C$_{20}$H$_{15}$F$_6$N$_2$ ([M+H]$^+$): 401.1447, found 401.1448. IR (v, cm$^{-1}$): 3695, 3584, 3055. [α]$^{25}_D$=+25.0 (c 0.26, DCM).

Example 5

5,6-Diphenylpiperazine-2,3-dione 7a (R,S) and 7b (R,R)

To a solution of 1,2-diphenylethylenediamine (300 mg, 1.43 mmol, 1 eq.) in toluene (10 mL) diethyl oxalate (227 mg, 1.55 mmol, 1.1 eq.) was added dropwise and the solution heated to reflux for 22 h. The reaction was monitored by TLC (EtOAc:MeOH 90:10). The reaction mixture was cooled with an ice bath and filtered; the cake was rinsed with EtOAc and collected. The filtrate was concentrated in vacuo and filtered again, using Et$_2$O as the solvent to give a second crop of the product. (R,S)-7a (white solid, 288 mg, 76%): $^1$H NMR (400 MHz, DMSO) δ: 8.98 (bs, 2H, NH), 7.22-7.12 (m, 6H, ArH), 6.77-6.73 (m, 4H, ArH), 5.07 (s, 2H, Ha). $^{13}$C NMR (100.6 MHz, DMSO) δ: 159.4 (C), 136.8 (C), 128.7 (CH), 128.7 (CH), 128.6 (CH), 128.6 (CH), 128.5 (CH), 59.3 (CH). HRMS required for C$_{16}$H$_{14}$N$_2$O$_2$ ([M+Na]$^+$): 289.0947, found 289.0953. IR (v, cm$^{-1}$): 3305, 3187, 3065, 2901, 1727, 1679. MP=289-291° C. (R,R)-7b (yellow oil, 189 mg, 50%): $^1$H NMR (400 MHz, MeOD) δ: 7.35-7.31 (m, 6H, ArH), 7.26-7.24 (m, 4H, ArH), 4.91 (s, 2H, H). $^{13}$C NMR (100.6 MHz, MeOD) δ: 159.6 (C), 137.7 (C), 128.7 (CH), 128.7 (CH), 128.6 (CH), 128.6 (CH), 127.6 (CH), 62.0 (CH). HRMS required for C$_{16}$H$_{14}$N$_2$O$_2$ ([M+Na]$^+$): 289.0947, found 289.0944. IR (v, cm$^{-1}$): 3221, 2402, 1688. [α]$^{25}_D$=+36.1 (c 0.41, MeOH).

Example 6

2,3-Diphenylpiperazine 8

To a solution of 5,6-diphenylpiperazine-2,3-dione (800 mg, 3.0 mmol, 1 eq.) in THF (60 mL) BH$_3$.THF (1M solution in THF, 12 mL, 12 mmol, 4 eq.) was added dropwise at 0° C. The reaction mixture was heated to reflux for 22 h, and then cooled to rt. 30 mL of H$_2$O were added dropwise followed by 30 mL of 3M HCl. The organic solvent was distilled off and the remaining solution heated for 1 further hour and then cooled to rt. The aq. solution was extracted with Et$_2$O, made basic with 3M aq. NaOH, and extracted into DCM. The combined organic extracts were dried, filtered, and concentrated in vacuo. Further purification was achieved by adding a saturated solution of HCl in MeOH until the solution was acidic. The MeOH was evaporated; Et$_2$O was added to solubilise impurities and removed with a Pasteur pipette. The solution was brought to basic pH with 3M aq. NaOH and extracted with DCM (×3); the combined organic phases were dried, and concentrated in vacuo to obtain the final product (R,S)-8a (364 mg, 51% yield): $^1$H NMR (400 MHz, DMSO) δ: 7.44-7.00 (m, 10H, ArH), 4.18 (s, 2H, H), 3.05-3.01 (m, 2H, H), 2.75-2.70 (m, 2H, H). $^{13}$C NMR (100.6 MHz, DMSO) δ: 143.1 (C), 129.2 (CH), 129.2 (CH), 128.6 (CH), 128.6 (CH), 126.8 (CH), 62.6 (CH), 44.2 (CH$_2$). HRMS required for C$_{16}$H$_{18}$N$_2$ ([M+H]$^+$): 239.1543, found 239.1543. IR (v, cm$^{-1}$): 3314, 3060, 3028, 2943, 2847. (R,R)-8b (614 mg, 86% yield): $^1$H NMR (400 MHz, CDCl$_3$) δ: 7.13-7.07 (m, 10H, ArH), 3.73 (s, 2H, H), 3.15 (s, 4H, H). $^{13}$C NMR (100.6 MHz, CDCl$_3$) δ: 141.2 (C), 128.0 (CH), 128.0 (CH), 127.8 (CH), 127.8 (CH), 127.3 (CH), 68.1 (CH), 47.0 (CH$_2$). IR (v, cm$^{-1}$): 3281 (NH), 2961 (NH). HRMS required for C$_{16}$H$_{18}$N$_2$ ([M+H]$^+$): 239.1543, found 239.1546. [α]$^{22}_D$=+86.8 (c 0.63, DCM).

Example 7

2,3-Diphenyl-1,4-diazabicyclo[2.2.2]octane 9

To a solution of 2,3-diphenylpiperazine (116 mg, 0.49 mmol, 1 eq.) and NEt$_3$ (0.23 mL, 1.96 mmol, 1.4 eq.) in toluene (5 mL) 1,2-dibromoethane (91 mg, 0.49 mmol, 1 eq.) was added dropwise and the resulting solution heated to reflux for 12 h and then cooled to rt. The reaction mixture was brought to pH 10 using 1M aq. NaOH and the organic layer was separated. The aq. layer was extracted with DCM (×3) and the combined organic extracts were dried, filtered, and concentrated in vacuo. For (R,S)-3b, the crude product mixture was purified by flash column chromatography (CHCl$_3$:MeOH 95:5, R$_f$=0.29) to give a brown oil (18 mg, 14%). (R,R)-3a was not obtained via this procedure, as only starting material was recovered.

Characterization of 3b—R$_f$=0.29 (CHCl$_3$:MeOH 95:5)): $^1$H NMR (400 MHz, CDCl$_3$) δ: 7.15-7.11 (m, 6H, ArH), 7.02-6.99 (m, 4H, ArH), 4.63 (s, 2H, H), 3.19-3.11 (m, 4H, H), 3.07-3.01 (m, 2H, H), 2.74-2.68 (m, 2H, Hc'). $^{13}$C NMR (100.6 MHz, CDCl$_3$) δ: 138.6 (C), 129.3 (CH), 129.3 (CH), 127.6 (CH), 127.6 (CH), 126.2 (CH), 62.6 (CH), 50.0 (CH$_2$), 41.1 (CH$_2$). HRMS required for C$_{18}$H$_{20}$H$_2$ ([M+H]$^+$): 265.1699, found 265.1705.

Example 8

(S)-1-Naphthylalanine methyl ester 10

To a solution of (S)—N-Boc-1-naphthylalanine (800 mg, 2.54 mmol, 1 eq.) in MeOH (8 mL) trimethylsilyl chloride (1.28 mL, 12.68 mmol, 5 eq.) was added dropwise and the solution was left stirring at rt for 38 h, followed by solvent removal in vacuo. Anhydrous Et$_2$O (20 mL) was added and the resulting slurry stirred for 15 min, and filtered. The cake was rinsed with Et$_2$O and dried to give a white solid (610 mg, 88%). $^1$H NMR (400 MHz, MeOD) δ: 8.08-8.06 (d, J=8.3 Hz, 1H, ArH), 7.96-7.88 (dd, J=24.0, 8.1 Hz, 2H, ArH), 7.65-7.42 (m, 4H, ArH), 4.41-4.37 (t, J=7.3 Hz, 1H, H), 3.85-3.80 (dd, J=14.4, 6.6 Hz, 1H, H), 3.70 (s, 3H, H), 3.58-3.52 (dd, J=14.4, 8.3 Hz, 1H, H). $^{13}$C NMR (100.6 MHz, MeOD) δ: 169.6 (C), 134.6 (C), 131.9 (C), 130.4 (C), 129.3 (CH), 129.0 (CH), 128.3 (CH), 127.0 (CH), 126.2 (CH), 125.7 (CH), 122.9 (CH), 53.7 (CH), 52.8 (CH$_3$), 34.0 (CH$_2$). HRMS required for C$_{14}$H$_{15}$NO$_2$ ([M+H]$^+$): 230.1167, found 230.1160. IR (v, cm$^{-1}$): 2832 (NH), 1744 (CO). [α]$^{25}_D$=+32.9 (c 0.12, MeOH).

Example 9

(S)-Methyl 2-((R)-2-(tert-butoxycarbonylamino)-3-(naphthalen-1-yl)propanamido)-3-(naphthalen-1-yl)propanoate 11

To a solution of the amino acids (S)—N-Boc-1-naphthylalanine (250 mg, 0.79 mmol, 1 eq.) and (S)-1-naphthylalanine methyl ester 10 (200 mg, 0.87 mmol, 1.1 eq.) in DCM (11 mL) HBTU (450 mg, 1.19 mmol, 1.5 eq.) and DiPEA (357 mg, 2.37 mmol, 3 eq.) were added. The reaction mixture was stirred for 2 h at rt, and quenched with sat. aq. NH$_4$Cl. The aq. layer was extracted into DCM and the combined organic layers were dried, filtered, and concentrated in vacuo. The crude product was purified by flash column chromatography (hexane:EtOAc 60:40, R$_f$=0.50 in hexane:EtOAc 70:30) to give a white solid (368 mg, 88%). $^1$H NMR (400 MHz, CDCl$_3$) δ: 8.14-8.00 (m, 2H, ArH), 7.87-7.82 (m, 2H, ArH), 7.77-7.71 (m, 2H, ArH), 7.58-7.46 (m, 4H, ArH), 7.39-7.25 (m, 3H, ArH), 7.01-6.98 (m, 1H, ArH), 5.99 (bs, 1H, NH), 5.08 (bs, 1H, NH), 4.78 (b, 1H, H), 4.43 (b, 1H, H), 3.48-3.40 (m, 7H, H), 1.40-1.15 (m, 9H, H). $^{13}$C NMR (100.6 MHz, CDCl$_3$) δ: 171.2 (C), 170.8 (C), 133.9 (C), 133.8 (C), 133.0 (C), 132.8 (C), 132.1 (C), 131.8 (C), 128.9 (CH), 128.8 (CH), 128.0 (CH), 127.9 (CH), 127.4 (CH), 126.5 (CH), 126.5 (CH), 126.3 (CH), 125.8 (CH), 125.8 (CH), 125.4 (CH), 125.2 (CH), 123.6 (CH), 123.5 (CH), 55.5 (CH), 53.3 (CH$_3$), 52.1 (CH), 36.0 (CH$_2$), 35.4 (CH$_2$), 28.2 (CH$_3$). HRMS required for C$_{32}$H$_{34}$N$_2$O$_5$ ([M+Na]$^+$): 549.2360, found 549.2363. IR (v, cm$^{-1}$): 3333 (NH), 1742 (NCO), 1665 (NCO). [α]$^{25}_D$=−54.7 (c 0.64, DMSO). MP=129-132° C.

Example 10

(3S,6S)-3,6-Bis(naphthalen-1-ylmethyl)piperazine-2,5-dione 12

Precursor 11 (668 mg, 1.57 mmol) was dissolved in formic acid (46 mL) and the solution stirred at it for 2 h. After evaporation in vacuo the remaining solid was dissolved in sec-butanol (88 mL) and toluene (23 mL) and the solution was refluxed for 2 h. After having cooled down to it the reaction solution was concentrated in vacuo and the crude product recrystallised from methanol/toluene to give a white solid (399 mg, 65%). $^1$H NMR (400 MHz, DMSO) δ: 8.10 (m, 2H, NH), 8.00-7.97 (m, 2H, ArH), 7.90-7.87 (m, 2H, ArH), 7.78-7.76 (d, $^3$J=8.1 Hz, 2H, ArH), 7.55-7.50 (m, 4H, ArH), 7.38-7.34 (m, 2H, ArH), 6.80-6.70 (m, 2H, ArH), 4.01-3.98 (m, 2H, H), 2.96-2.91 (dd, $^2$J=14.0 Hz, $^3$J=4.8 Hz, 2H, H), 2.46-2.41 (dd, $^2$J=14.0 Hz, $^3$J=6.4 Hz, 2H, H). $^{13}$C NMR (100.6 MHz, DMSO) δ: 167.1 (C), 134.4 (C), 133.4 (C), 132.6 (C), 129.5 (CH), 129.4 (CH), 128.9 (C), 128.7 (C), 128.4 (C), 128.2 (CH), 127.0 (CH), 126.4 (CH), 126.2 (CH), 124.7 (CH), 56.2 (CH), 37.8 (CH$_2$). HRMS required for C$_{26}$H$_{22}$N$_2$O$_2$ ([M+Na]$^+$): 417.1573, found 417.1571. IR (v, cm$^{-1}$): 3193 (NH), 3045 (NH), 1672 (NCO). [α]$^{22}_D$=−70.3 (c 0.55, CH$_3$COOH). MP=273-275° C.

Example 11

(2S,5S)-2,5-Bis(naphthalen-1-ylmethyl)piperazine 13

To a well-stirred suspension of 29 (180 mg, 0.46 mmol, 1 eq.) in THF (3 mL) BH$_3$.THF (1M solution in THF, 2.74 mmol, 2.74 mL, 6 eq.) was added dropwise at 0° C. The solution was stirred at it for 1 h followed by 2 h at reflux. The solution was cooled to rt, filtered, cooled to 0° C. and slowly treated with 12% HBr/AcOH (3 mL). The mixture was stirred for 2 h and left standing overnight. The crude product precipitated as the dihydrobromide salt and was collected by filtration, using Et$_2$O to wash the cake. The filtrate solution was concentrated in vacuo and the remains dissolved in DCM and filtrated again to give a second crop of the product as a white solid (225 mg, 93%). After neutralisation: $^1$H NMR (400 MHz, CDCl$_3$) δ: 8.15-8.13 (d, J=8.1 Hz, 2H, ArH), 7.88-7.86 (m, 2H, ArH), 7.78-7.75 (m, 2H, ArH), 7.55-7.47 (m, 4H, ArH), 7.44-7.41 (m, 4H, ArH), 3.50-3.45 (dd, J=13.4, 6.1 Hz, 2H, H), 3.39-3.34 (dd, J=13.4, 7.8 Hz, 2H, H), 3.26 (m, 2H, H), 3.05-3.00 (dd, J=11.9, 5.8 Hz, 2H, H), 2.93-2.89 (dd, J=11.9, 3.3 Hz, 2H, H). $^{13}$C NMR (100.6 MHz, CDCl$_3$) δ: 135.2 (C), 134.0 (C), 132.2 (C), 128.8 (CH), 127.4 (CH), 127.2 (CH), 126.0 (CH), 125.6 (CH), 125.4 (CH), 124.0 (CH), 54.6 (CH), 47.9 (CH$_2$), 35.5 (CH$_2$). HRMS required for C$_{26}$H$_{26}$N$_2$ ([M+H]$^+$): 367.2169, found 367.2164. IR (v, cm$^{-1}$): 2917 (NH), 2726 (NH). [α]$^{22}_D$=+19.7 (c 0.4, DCM). MP: 172-174° C.

Example 12

(2S)-2,5-Bis(naphthalen-1-ylmethyl)-1,4-diazabicyclo[2.2.2]octane 14a/b

To a solution of 13 (207 mg, 0.57 mmol, 1 eq.) and NEt$_3$ (0.67 mL) in toluene (10 mL) dibromoethane (173 mg, 0.92 mmol, 1.63 eq.) was added dropwise and the solution was heated to reflux for 5 days. The reaction mixture was cooled to rt and brought to pH 9/10 with 1M aq. NaOH. The organic phase was separated and the aq. layer extracted with DCM (×3). The combined organic phases were dried, filtered, and concentrated in vacuo. The crude product mixture was purified by flash column chromatography (CHCl$_3$:MeOH 97:3) to give the two diastereomers (193 mg, combined yield 87%) as brown oils in a 2:1 ratio. 14b: $^1$H NMR (500 MHz, CDCl$_3$) δ: 8.13-8.11 (d, J=8.5 Hz, 2H, ArH), 7.91-7.90 (d, J=7.8 Hz, 2H, ArH), 7.80-7.78 (dd, J=7.8, 1.6 Hz, 2H, ArH), 7.60-7.56 (dt, J=6.6, 1.6 Hz, 2H, ArH), 7.54-7.51 (dt, J=7.9, 1.0 Hz, 2H, ArH), 7.47-7.43 (m, 4H, ArH), 3.58-3.54 (dd, $^2$J=13.9 Hz, $^3$J=5.7 Hz, 2H, H), 3.31-3.26 (dd, $^2$J=13.9 Hz, $^3$J=8.6 Hz, 2H, H), 3.17-3.11 (m, 2H, H), 3.06-3.01 (dd, $^2$J=13.6 Hz, $^3$J=8.2 Hz, 2H, H), 2.84-2.78 (m, 4H, H), 2.77-2.72 (dd, $^2$J=13.6 Hz, $^3$J=8.8 Hz, 2H, H). $^{13}$C NMR (125.8 MHz, CDCl$_3$) δ: 134.6 (C), 134.0 (C), 132.0 (C), 129.0 (CH), 127.3 (CH), 126.8 (CH), 126.1 (CH), 125.6 (CH), 125.5 (CH), 123.6 (CH), 55.0 (CH), 48.9 (CH$_2$), 47.6 (CH$_2$), 36.5 (CH$_2$). HRMS required for C$_{28}$H$_{28}$N$_2$ ([M+

H]+): 393.2325, found 393.2324. IR (v, cm⁻¹): 3055, 2987, 2306. $[\alpha]^{25}_D$=+60.6 (c 0.09, DCM).

14a: ¹H NMR (500 MHz, CDCl₃) δ: 8.01-7.99 (d, ³J=7.9 Hz, 2H, ArH), 7.84-7.82 (dd, ³J=6.9 Hz, ²J=1.9 Hz, 2H, ArH), 7.72-7.71 (d, ³J=8.2 Hz, 2H, ArH), 7.49-7.41 (m, 4H, ArH), 7.39-7.36 (m, 2H, ArH), 7.33-7.32 (d, ³J=6.3 Hz, 2H, ArH), 3.49-3.45 (dd, ²J=13.2 Hz, ³J=5.3 Hz, 2H, H), 3.28-3.21 (m, 2H, H), 3.16-3.12 (dd, ²J=13.2 Hz, ³J=8.8 Hz, 2H, H), 3.10-3.05 (m, 2H, H), 2.93-2.89 (dd, ²J=13.3 Hz, ³J=8.2 Hz, 2H, Hc), 2.86-2.81 (m, 2H, H), 2.72-2.67 (dd, ²J=13.3 Hz, ³J=7.7 Hz, 2H, H). ¹³C NMR (125.8 MHz, CDCl₃) δ: 134.5 (C). 134.0 (C), 131.8 (C), 128.9 (CH), 127.2 (CH), 126.7 (CH), 126.0 (CH), 125.5 (CH), 125.4 (CH), 123.5 (CH), 56.4 (CH₂), 54.2 (CH), 41.3 (CH₂), 36.5 (CH₂). HRMS required for $C_{28}H_{28}N_2$ ([M+H]⁺): 393.2325, found 393.2328. IR (v, cm⁻¹): 3054, 2986, 2305. $[\alpha]^{25}_D$=+70.4 (c 0.42, DCM).

Compound 14a is a precursor for a fluorinating agent 115, the structure of which is depicted in paragraph [0060] above. Compound 14b is a precursor for a fluorinating agent 116, the structure of which is depicted in paragraph [0060] above.

Example 13

(S)-Methyl 2-((S)-2-(tert-butoxycarbonylamino)-3-phenylpropanamido)-3-phenylpropanoate 15

To a solution of $_L$-phenylalanine methyl ester hydrochloride (4.87 g, 22.62 mmol) and N-Boc-$_L$-phenylalanine (5.00 g, 18.85 mmol) in CH₂Cl₂ (188 mL) at 0° C. was added HBTU (10.72 g, 28.27 mmol) and DIPEA (9.80 mL, 56.54 mmol). The mixture was stirred for 2 h at r.t. The solution was quenched with sat. aq. NH₄Cl (20 mL) and the aqueous layer was extracted with CH₂Cl₂ (2×30 mL). The organic layers were dried, filtered and concentrated under reduced pressure. The residue was purified by flash column chromatography (60:40 EtOAc:hexane) to give 15 as white solid (7.81 g, 97%) $R_f$ 0.30 (30:70 EtOAc:hexane); IR (v, KBr/cm⁻¹): 3340, 1744, 1696, 1607, 1665, ¹H NMR (500 MHz, CDCl₃) δ: 1.41 (s, 9H, C(CH₃)₃), 3.00-3.10 (m, 4H, ArCH₂), 3.67 (s, 3H, OCH₃), 4.35 (d, J=6.3 Hz, 1H, NHCH), 4.79 (q, J=6.2 Hz, 1H, NHCH), 4.97 (br d, J=5.5 Hz, 1H, NF), 6.31 (br d, J=7.0 Hz, 1H, NH), 6.97-7.00 (m, 2H, ArH), 7.23-7.30 (m, 8H, ArH); ¹³C NMR (125.8 MHz, CDCl₃) 6:28.2 (C(CH₃)₃), 37.9 (ArCH₂), 38.2 (ArCH₂), 52.3 (OCH₃), 53.2 (NHCH), 55.7 (NHCH), 80.2 (C(CH₃)₃), 126.9 (CH), 127.1 (CH), 128.5 (2×CH), 128.7 (2×CH), 129.2 (2×CH), 129.3 (2×CH), 135.6 (C), 136.5 (C), 155.2 (NHCOCH), 170.7 (CO), 171.3 (CO); mp 116-117° C.; $[\alpha]^{22}_D$–12.5 (c 1, MeOH);); HRMS (ESI)⁺: m/z calcd for $C_{24}H_{30}N_2O_5$ [M+Na]⁺449.2043, found 449.2027.

Example 14

(S)-Methyl 2-((S)-2-(tert-butoxycarbonylamino)-3-methylbutanamido)-3-methylbutanoate 16

To a solution of $_L$-valine methyl ester hydrochloride (4.63 g, 27.62 mmol) and N-Boc-$_L$-valine (5.0 g, 23.01 mmol) in CH₂Cl₂ (230 mL) at 0° C. was added HBTU (13.09 g, 34.52 mmol) and DIPEA (12.0 mL, 69.04 mmol). The mixture was stirred for 2 h at r.t. The solution was quenched with sat. aq. NH₄Cl (20 mL) and the aqueous layer was extracted with CH₂Cl₂ (2×30 mL). The organic layers were dried, filtered and concentrated under reduced pressure. The residue was purified by flash column chromatography (60:40 EtOAc:hexane) to give 16 as white solid (7.36 g, 98%); $R_f$ 0.50 (30:70 EtOAc:hexane); IR (v, KBr/cm⁻¹): 3350, 1784, 1676, 1617, 1635, ¹H NMR (500 MHz, CDCl₃) δ: 0.94 (td, J=14.9, 6.8 Hz, 12H, [CH(CH₃)₂]₂), 1.45 (s, 9H, C(CH₃)₃), 2.15-2.19 (m, 2H, [CH(CH₃)₂]₂), 3.74 (s, 3H, OCH₃), 3.91 (dd, J=8.5, 6.6 Hz, 1H, NHCH), 4.5 (dd, J=8.7, 4.9 Hz, 1H, NHCH), 5.05 (dd, J=7.2, 0.3 Hz, 1H, NH), 6.36 (dd, J=7.0, 0.4 Hz, 1H, NH); ¹³C NMR (125.8 MHz, CDCl₃) δ: 17.7 (CHCH₃), 17.9 (CHCH₃), 18.9 (CHCH₃), 19.3 (CHCH₃), 28.3 (C(CH₃)₃), 30.6 (CH(CH₃)₂), 31.2 (CH(CH₃)₂), 52.1 (OCH₃), 57.0 (NHCH), 60.2 (NHCH), 79.9 (C(CH₃)₃), 156.8 (NHCOCH), 171.5 (CO), 172.1 (CO); mp 145-147° C.; $[\alpha]^{22}_D$–27.0 (c 1, MeOH); HRMS (ESI)⁺: m/z calcd for $C_{16}H_{30}N_2O_5$ [M+Na]⁺353.1847, found 353.1837.

Example 15

(3S,6S)-3,6-Bis(phenylmethyl)piperazine-2,5-dione, 17

A solution of (S)-methyl 2-((S)-2-(tert-butoxycarbonylamino)-3-phenyl-propanamido)-3-phenylpropanoate (6.80 g, 15.9 mmol) in formic acid (159 mL) was stirred for 2 h at r.t and the solution was concentrated under reduced pressure. The residue was dissolved in sec-butanol (600 mL) and toluene (160 mL) and refluxed for 2 h. The resulting precipitate was filtered, and then recrystallised from methanol/acetone to give 17 as white solid (4.30 g, 92%); IR (v, KBr/cm⁻¹): 3187, 3080, 1669, 1665, 1497, 1461; ¹H NMR (500 MHz, CF₃CO₂D) δ: 2.32 (dd, J=14.0, 7.6 Hz, 2H, H₁), 3.08 (dd, J=14.0, 3.7 Hz, 2H, H₂), 4.58 (dd, J=7.0, 4.0 Hz, 2H, NHCH), 7.13 (d, J=7.5 Hz, 4H, ArH), 7.34-7.42 (m, 6H, ArH); ¹³C NMR (125.8 MHz, CF₃CO₂D) δ: 39.6 (2×ArCH₂), 56.6 (2×NHCH), 128.5 (2×CH), 129.4 (4×CH), 129.9 (4×CH), 133.6 (2×C), 170.9 (2×NHCO); mp 308-310° C.; $[\alpha]^{22}_D$–99.0 (c 0.2, AcOH); HRMS (FI)⁺: m/z calcd for $C_{18}H_{18}N_2O_2$ [M]⁺294.1368, found 294.1355.

Example 16

(3S,6S)-3,6-Bis(isopropyl)piperazine-2,5-dione 18

A solution of (S)-methyl 2-((S)-2-(tert-butoxycarbonylamino)-3-methyl-butanamido)-3-methylbutanoate (7.30 g, 22.0 mmol) in formic acid (170 mL) was stirred for 2 h at r.t. The solution was concentrated under reduced pressure and the residue was dissolved in sec-butanol (650 mL) and toluene (170 mL) and refluxed for 2 h. The resulting precipitate was filtered, and then recrystallised from methanol/ether to give 18 as white solid (2.40 g, 55%); IR (v, KBr/cm⁻¹): 3180, 3050, 1661, 1660, 1477, 1451; ¹H NMR (500 MHz, DMSO-d₆) δ: 0.84 (d, J=6.8 Hz, 6H, CH(CH₃)₂, H₁), 0.96 (d, J=7.1 Hz, 6H, CH(CH₃)₂, H₂), 2.08-2.21 (m, 2H, CH(CH₃)₂), 3.69 (t, J=2.3 Hz, 2H, NHCH), 7.94 (br s, 2H, WI); ¹³C NMR (125.8 MHz, DMSO-d₆) δ: 17.3 (CH(CH₃)₂), 18.7 (CH(CH₃)₂), 30.7 (CH(CH₃)₂), 31.0 (CH(CH₃)₂) 59.1 (2×NHCH), 167.4 (2×NHCO); mp 272-273° C.; $[\alpha]^{22}_D$–61.0 (c 0.48, AcOH); HRMS (FI)⁺: m/z calcd for $C_{10}H_{18}N_2O_2$ [M]⁺198.1447, found 198.1440.

Example 17

(2S,5S)-2,5-Bis(phenylmethyl)piperazine dihydrobromide 19

To a vigorously stirred suspension of (3S,6S)-3,6-bis-(phenylmethyl)-piperazine-2,5-dione (1.20 g, 5.10 mmol) in THF (26 mL) was added dropwise BH₃THF (1 M solution in THF, 30 mL) at 0° C. The mixture was stirred for 1 h, slowly warming to r.t and heated to reflux for 2 h. The solution was filtered, cooled to 0° C., and 12% HBr/AcOH (10 mL) was slowly added. After stirring for 2 h, dry hexane was added and the solution was left to stand overnight in the freezer. The resulting dihydrobromide precipitates were collected by filtration, and then recrystallised from methanol/ether to give 19 as white solid (1.20 g, 55%). IR (ν, KBr/cm$^{-1}$): 3300, 2700, 1455, 1070, 970, 740; $^1$H NMR (500 MHz, DMSO-d$_6$) δ: 3.22-3.32 (overlap m, 8H, ArCH$_2$, NHCH$_2$), 3.89 (dq, J=9.9, 5.0 Hz, 2H, NHCH), 7.30-7.43 (m, 10H, ArH), 9.40 (br s, 4H, NH); $^{13}$C NMR (125.8 MHz, DMSO-d$_6$) δ: 33.8 (2×ArCH$_2$), 40.7 (2×NHCH$_2$), 51.9 (2×NHCH), 127.4 (2×CH), 128.9 (4×CH) 129.4 (4×CH), 135.3 (2×C); mp 226-228° C.; [α]$^{22}_D$–13.4 (c 2, H$_2$O); HRMS (FI)$^+$: m/z calcd for C$_{18}$H$_{24}$Br$_2$N$_2$ [M]$^+$426.0306. found 426.0286

Example 18

(2S,5S)-2,5-Bis(isopropyl)piperazine dihydrobromide, 20

To a vigorously stirred suspension of (3S,6S)-3,6-bis-(isopropyl)-piperazine-2,5-dione (1.70 g, 8.60 mmol) in THF (43 mL) was added dropwise BH$_3$.THF (1 M solution in THF, 52 mL) at 0° C. The mixture was stirred for 1 h, warming to r. t and heated to reflux for 2 h. The solution was filtered, cooled to 0° C., and 12% HBr/AcOH (15 mL) was slowly added. After stirring for 2 h, dry hexane was added and the solution was left to stand overnight in the freezer. The resulting dihydrobromide precipitates were collected by filtration, and then recrystallised from methanol/ether to give 13 as white solid (1.10 g, 39%); IR (ν, KBr/cm$^{-1}$): 3425, 3029, 2915, 1470, 970; $^1$H NMR (500 MHz, DMSO-d$_6$) δ: 0.96-1.03 (dd, J=22.3, 6.6 Hz, 12H, [CH(CH$_3$)$_2$]$_2$), 2.10-2.18 (m, 2H, [CH(CH$_3$)$_2$]$_2$), 2.49-2.51 (m, 2H, [NHCH]$_2$), 3.28-3.37 (m, 4H, [NHCH$_2$]$_2$), 8.86 (br s, 2H, NH), 9.48 (br s, 2H NH); $^{13}$C NMR (125.8 MHz, DMSO-d$_6$) δ: 19.6 [CH(CH$_3$)$_2$]$_2$), 27.2 [CH(CH$_3$)$_2$]$_2$), 40.8 ([NHCH$_2$]$_2$), 56.3 (NHCH); mp 265-267° C.; [α]$^{22}_D$–22.1 (c 1, H$_2$O); HRMS (FI)$^+$: m/z calcd for C$_{10}$H$_{24}$Br$_2$N$_2$ [M]$^+$330.0306, found 330.0286

Example 19

(2S,5S)-2,5-Bis(phenylmethyl)piperazine 21

To a vigorously stirred suspension of (3S,6S)-3,6-bis (phenylmethyl)-piperazine-2,5-dione (4.30 g, 14.60 mmol) in THF (72 mL), BH$_3$.THF (1M solution in THF, 87 mL, 84 mmol) was added dropwise at 0° C. The mixture was stirred for 1 h, warming to r.t and heated to reflux for 2 h. The solution was filtered, cooled at 0° C., carefully quenched with methanol (20 mL), and then concentrated under reduced pressure. The residual crystalline material was dissolved in methanol (17 mL) and THF (7 mL), and then a suspension of 10% palladium on carbon (177 mg, 50% wet) in methanol (17 mL) was added. The mixture was stirred for 12 h at r t. The crude reaction mixture was filtered and concentrated under reduce pressure. Purification by flash column chromatography (8:92 methanol:chloroform) gave 21 as colourless oil (3.20 g, 82%); R$_f$ 0.51 (5:95 methanol: chloroform); IR (ν, neat/cm$^{-1}$): 3320, 3020, 2700, 1455, 1305 1190, 990, 742; $^1$H NMR (500 MHz, CDCl$_3$) δ: 1.59 (br s, 2H, NH), 2.79-3.03 (overlap m, 10H, ArCH$_2$, NHCH$_2$, NHCH), 7.21-7.35 (m, 10H, ArH); $^{13}$C NMR (125.8 MHz, CDCl$_3$) δ: 38.1 (2×ArCH$_2$), 47.5 (2×NHCH$_2$), 55.2 (2×NHCH), 125.7 (2×CH) 128.0 (4×CH), 128.7 (4×CH), 138.9 (2×C); HRMS (FI)$^+$: m/z calcd for C$_{18}$H$_{22}$N$_2$ [M]$^+$ 266.1775, found 266.1783.

Example 20

(2S,5S)-2,5-Bis(isopropyl)piperazine 22

To a vigorously stirred suspension of (3S,6S)-3,6-bis (isopropyl)piperazine-2,5-dione (4.56 g, 23.06 mmol) in THF (115 mL), BH$_3$.THF (1 M solution in THF, 138 mL, 138.37 mmol) was added dropwise at 0° C. The mixture was stirred for 1 h, warming to r.t, then heated to reflux for 2 h. The solution was filtered, cooled at 0° C., carefully quenched with methanol (30 mL), and then concentrated under reduced pressure. The residual crystalline material was dissolved in methanol (30 mL) and THF (12 mL), and then a suspension of 10% palladium on carbon (320 mg, 50% wet) in methanol (30 mL) was added. The mixture was stirred for 12 h at r.t. The crude reaction mixture was filtered and concentrated under reduce pressure. Purification by flash column chromatography (8:92 methanol:chloroform) gave 22 as colourless oil (3.2 g, 75%); R$_f$ 0.16 (5:95 methanol:chloroform); IR (ν, neat/cm$^{-1}$): 3425, 3029, 2915, 1470, 970; $^1$H NMR (500 MHz, CDCl$_3$) δ: 0.83 (d, J=6.7 Hz, 6H, CH(CH$_3$)$_2$), 0.88 (d, J=6.7 Hz, 6H, CH(CH$_3$)$_2$), 1.73 (br s, 2H, NH), 1.80-1.89 (m, 2H, [CH(CH$_3$)$_2$]$_2$), 2.23 (dt, J=8.8, 4.5 Hz, 2H, [NHCH]$_2$), 2.76 (d, 4H, [NHCH$_2$]$_2$); $^{13}$C NMR (125.8 MHz, CDCl$_3$) δ: 19.2 (CH(CH$_3$)$_2$), 19.6 (CH (CH$_3$)$_2$), 27.7 (CH(CH$_3$)$_2$]$_2$), 45.8 ([NHCH$_2$]$_2$), 60.2 (NHCH); [α]$^{22}_D$–22.5 (c 1, H$_2$O); HRMS (ESI)$^+$: m/z calcd for C$_{10}$H$_{22}$N$_2$ [M-FI-1]$^+$171.1783, found 171.1651.

Compound 22 can be converted to fluorinating agents 113 and 114, the structures of which are depicted in paragraph [0060] above.

Example 21

(1R,2S,4R,5S)-2,5-Bis(phenylmethyl)-1,4-diazabicyclo[2.2.2]octane 23a (1S,2S,4S,5S)-2,5-Bis(phenylmethyl)-1,4-diazabicyclo[2.2.2]octane 23b To a solution of (2S,5S)-2,5-bis(phenylmethyl)piperazine (1.00 g, 3.75 mmol) in toluene (10 mL), 1,2-dibromoethane (0.43 g, 2.30 mmol) and triethylamine (2 mL) were added and the solution was heated to reflux for 12 h. The reaction mixture was then cooled to r.t and brought to pH 9-10 with 1M aq. NaOH. The organic phase was separated and the aqueous phase was extracted with chloroform (3×15 mL). The combined organic phases were dried, filtered and concentrated under reduced pressure. Purification by flash column chromatography (2:98 methanol:chloroform) gave 23a and 23b as brown oils in a 1:1 ratio.

(1R,2S,4R,5S)-2,5-Bis(phenylmethyl)-1,4-diazabicyclo [2.2.2]octane, 23a (0.21 g, 19%); R$_f$ 0.35 (2:98 methanol: chloroform); IR (ν, neat/cm$^{-1}$): 3060, 2965, 2809, 1673, 1460, 1311, 1161, 775; $^1$H NMR (500 MHz, CDCl$_3$) δ: 2.51-2.58 (m, 2H), 2.64-2.77 (m, 4H), 2.90-2.97 (m, 6H), 3.07 (td, J=9.5, 3.5 Hz, 2H), 7.20 (dt, J=7.5, 2.6 Hz, 6H, ArH), 7.27-7.31 (m, 4H, ArH); $^{13}$C NMR (125.8 MHz, CDCl$_3$) δ: 39.2 (2×CH$_2$), 41.2 (2×CH$_2$), 55.6 (2×CH), 56.4 (2×CH$_2$), 126.2 (2×CH) 128.4 (4×CH), 128.8 (4×CH), 139.0 (2×C); [α]$^{22}_D$+104.3 (c 0.5, MeOH); HRMS (ESI)$^+$: m/z calcd for C$_{20}$H$_{24}$N$_2$ [M+H]$^+$ 293.1973, found 293.1939.

(1S,2S,4S,5S)-2,5-Bis(phenylmethyl)-1,4-diazabicyclo[2.2.2]octane, 23b (0.19 g, 17%); $R_f$ 0.30 (2:98 methanol: chloroform); IR (v, neat/cm$^{-1}$): 3055, 2960, 2812, 1670, 1465, 1310, 1131, 770; $^1$H NMR (500 MHz, CDCl$_3$) δ: 2.67-2.80 (m, 10H), 2.96 (td, J=15.9, 6.6 Hz, 4H), 7.18-7.33 (m, 10H, ArH); $^{13}$C NMR (100.6 MHz, CDCl$_3$) δ: 39.1 (2×CH$_2$), 47.5 (2×CH$_2$), 49.0 (2×CH$_2$), 56.4 (2×CH), 126.4 (2×CH) 128.6 (4×CH), 129.1 (4×CH), 139.0 (2×C); $[α]^{22}_D$+ 133.8 (c 0.3, MeOH); HRMS (ESI)$^+$: m/z calcd for C$_{20}$H$_{24}$N$_2$ [M-FI-1]$^+$293.1961, found 293.1939.

Example 25

1-Chloromethyl-4-aza-1-azoniabicylo[2.2.2]octane chloride 24

1,4-Diazabicyclo[2.2.2]octane (0.50 g, 4.46 mmol) was solubilised in CH$_2$Cl$_2$ and acetone (5 mL, 1:1) and the mixture was left to stand, without stirring, under an atmosphere of argon for 48 h at r.t. The resulting white precipitate formed was filtered and washed with acetone (2×10 mL) to afford 24 as white solid (0.60 g, 68%); IR (v, KBr/cm$^{-1}$): 1107, 723; $^1$H NMR (500 MHz, D$_2$O) δ: 3.25 (t, J=7.6 Hz, 6H, H3, H5, H7), 3.55 (t, J=7.6 Hz, 6H, H2, H6, H8), 5.12 (s, 2H, CH$_2$Cl); $^{13}$C NMR (125.8 MHz, D$_2$O) δ:44.3 (C3, C5, C7), 51.6 (C2, C6, C8), 68.6 (CH$_2$Cl); mp 145-147° C.; HRMS (FI)$^+$: m/z calcd for C$_7$H$_{14}$Cl$_2$N$_2$[M]$^+$197.1108, found 196.0534.

Example 26

1-Chloromethyl-4-aza-1-azoniabicylo[2.2.2]octane tetrafluoroborate 25

To a solution of 1-chloromethyl-4-aza-1-azoniabicylo[2.2.2]octane chloride (0.55 g, 2.79 mmol) in anhydrous CH$_3$CN (5 mL), sodium tetrafluoroborate (0.31 g, 2.79 mmol) was added. The reaction mixture was stirred for 24 h at r.t and filtered to remove sodium chloride formed. The precipitate was washed with anhydrous acetonitrile (3×10 mL). The combined filtrates were concentrated under reduced pressure to afford 25 as white solid (0.69 g, 99%). IR (v, KBr/cm$^{-1}$): 1115, 1023, 805; $^1$H NMR (500 MHz, D$_2$O) δ: 3.28 (t, J=7.6 Hz, 6H, H3, H5, H7), 3.57 (t, J=7.6 Hz, 6H, H2, H6, H8), 5.13 (s, 2H, CH$_2$Cl); $^{13}$C NMR (125.8 MHz, D$_2$O) δ: 44.3 (C3, C5, C7), 51.6 (C2, C6, C8), 68.6 (CH$_2$Cl); $^{19}$F NMR (470.4 MHz, D$_2$O) δ: −151.0 (s, BF$_4$); mp 131-133° C.; HRMS (FI)$^+$: m/z calcd for C$_7$H$_{14}$BClF$_4$N$_2$ [M]$^+$248.4571, found 248.0876

Example 27

1-Methyl-4-aza-1-azoniabicylo[2.2.2]octane trifluoromethanesulfonate 26

To a solution of 1,4-diazabicyclo[2.2.2]octane (0.57 g, 5.08 mmol) in Et$_2$O (67 mL), methyl trifluoromethanesulfonate (0.73 g, 4.42 mmol) was added dropwise at 0° C. The reaction mixture was stirred for 1 h at 0° C., then for 2 h at r.t and the resulting white precipitate was filtered and washed with acetone (2×10 mL) to afford 26 as white solid (1.26 g, 90%); IR (v, KBr/cm$^{-1}$): 1469, 1315, 1272, 1153, 1030, 911; $^1$H NMR (500 MHz, D$_2$O) δ: 3.03 (s, 3H, OCH$_3$), 3.19 (t, J=7.6 Hz, 6H, H3, H5, H7), 3.38 (t, J=7.6 Hz, 6H, H2, H6, H8); $^{13}$C NMR (125.8 MHz, D$_2$O) δ: 44.6 (OCH$_3$), 51.9 (C3, C5, C7), 54.3 (C2, C6, C8), 121.6 (CF$_3$); $^{19}$F NMR (470.4 MHz, D$_2$O) δ: −79.7 (s, SO$_3$CF$_3$); mp 214-216° C.; HRMS (FI)$^+$: m/z calcd for C$_8$H$_{15}$F$_3$N$_2$O$_3$S [M]$^+$276.0765, found 276.0755.

Example 28

(2R,3R)-1-methyl-2,3-diphenyl-4-aza-1-azoniabicyclo[2.2.2]octane trifluoromethanesulfonate 27

To a solution of 2,3-diphenyl-1,4-diazabicyclo[2.2.2]octane (0.50 g, 1.89 mmol) in Et$_2$O (92 mL), methyl trifluoromethanesulfonate (0.27 g, 1.64 mmol) was added dropwise at 0° C. The reaction mixture was stirred for 1 h at 0° C., then for 2 h at r.t. The resulting white precipitate was filtered and washed with acetone (2×10 mL) to afford 27 as a brown solids.

(2R,3R)-1-methyl-2,3-diphenyl-4-aza-1-azoniabicyclo[2.2.2]octane trifluoro methanesulfonate, 27 (0.70 g, 99%); IR (v, KBr/cm$^{-1}$): 1469, 1272, 1153, 1030, 992; $^1$H NMR (500 MHz, CD$_3$CN) δ: 2.60 (s, 3H, CH$_3$), 3.10-3.18 (m, 3H, CH$_2$), 3.39-3.48 (m, 2H, CH$_2$), 3.52-3.57 (m, 2H, CH$_2$), 3.75 (t, J=11.3 Hz, 1H, CH$_2$), 4.75 (d, J=9.6 Hz, 1H, CH), 4.81 (d, J=9.6 Hz, 1H, CH), 7.29-7.37 (m, 5H, ArH), 7.56-7.59 (m, 3H, ArH), 7.78 (dd, J=1.8, 7.4 Hz, 2H, AH); $^{13}$C NMR (125.8 MHz, CD$_3$CN) δ: 40.8 (CH$_2$), 47.1 (CH$_2$), 50.0 (CH$_3$), 50.7 (CH$_2$), 58.4 (CH$_2$), 63.4 (CH), 72.6 (CH), 120.8 (CF$_3$), 128.1 (CH), 129.2 (CH), 129.7 (CH), 130.9 (CH), 131.4 (C), 132.3 (CH), 137.8 (C); mp 197-199° C.; $[α]^{22}_D$−85.7 (c 0.27, MeOH); HRMS (ESI)$^+$: m/z calcd for C$_{20}$H$_{23}$F$_3$N$_2$O$_3$S [M]$^+$428.1381, found 428.1273, Example 29

1-Fluoro-4-methyl-1,4-diazoniabicylo[2.2.2]octane bis(trifluoromethanesulfonate) 28

To a solution of 1-methyl-4-aza-1-azoniabicylo[2.2.2]octane trifluoromethanesulfonate (0.10 g, 0.36 mmol) and sodium trifluoromethane-sulfonate (0.06 g, 0.36 mmol) in acetonitrile (6 mL), a homogeneous 1:9 (v/v) mixture of F$_2$ (0.013 g, 0.36 mmol) and N$_2$ was passed at a rate of 15 mL/min at −35° C. for 5$^{1/2}$ minutes. The product was filtered to remove sodium fluoride and concentrated under reduced pressure to afford 28 as white solid (0.16 g, 99%), IR (v, KBr/cm$^{-1}$): 1524, 1264, 1170, 1035, 914; $^1$H NMR (500 MHz, CD$_3$CN) δ: 3.34 (s, 3H, OCH$_3$), 4.26 (t, J=7.4 Hz, 6H, H2, H6, H8), 4.71 (q, J=7.5 Hz, 6H, H3, H5, H7); $^{13}$C NMR (125.8 MHz, CD$_3$CN) δ: 53.3 (OCH$_3$), 57.5 (C2, C6, C8), 54.3 (C3, C5, C7), 120.3 (CF$_3$); $^{19}$F NMR (470.4 MHz, CD$_3$CN) δ: +46.5 (s, NF$^+$), −79.7 (s, CF$_3$SO$_3$$^{31}$); HRMS: analysis ongoing.

Example 30

(2R,3R)-1-fluoro-4-methyl-2,3-diphenyl-1,4-diazoniabicyclo[2.2.2]octane bis(trifluoromethanesulfonate) 29

To a solution of (2R,3R)-1-methyl-2,3-diphenyl-4-aza-1-azoniabicyclo[2.2.2]octane trifluoro-methanesulfonate (0.10 g, 0.23 mmol) and sodium trifluoromethane-sulfonate (0.04 g, 0.23 mmol) in acetonitrile (7 mL), a homogeneous 1:9 (v/v) mixture of F$_2$ (0.09 g, 0.23 mmol) and N$_2$ was passed at a rate of 15 mL/min at −35° C. for 3% minutes. The product was filtered to remove sodium fluoride and concentrated under reduced pressure to afford 29 as a white yellow-brown solid.

(2R,3R)-1-fluoro-4-methyl-2,3-diphenyl-1,4-diazoniabicyclo[2.2.2]octane bis(trifluoromethanesulfonate), 29 (0.142 g, 86%), IR (v, KB$^r$/cm$^{-1}$) 1469, 1279, 1153, 1032, 75$^6$, 713; $^1$H NMR (500 MHz, CD$_3$CN) δ: 2.95 (s, 3H, CH$_3$), 4.24 (t, J=11.9 Hz, 1H, CH$_2$), 4.42-4.49 (m, 1H, CH$_2$), 4.55 (dt, J=11.8, 8.9 Hz, 1H, CH$_2$), 4.70-4.82 (m, 3H, CH$_2$), 5.02 (q, J=9.9 Hz, 1H, CH$_2$), 5.30-5.$^.3$7 (m, 1H, CH$_2$), 6.03 (d, J=10.9 Hz, 1H, CH), 6.54 (d, J=$_1$0.9 Hz, 1H, CH), 7.58-7.61 (m, 4H, ArH), 7.65-7.69 (m, 2H, ArH), 7.89-7.93 (m, 4H, ArH); $^{13}$C NMR (125.8 MHz, CD$_3$CN) δ: 50.9 (CH$_3$), 53.5 (CH$^2$), 53.6 (CH$_2$), 58.8 (C$_{H2}$), 59.9 (CH$_2$), 74.$^5$ (CH), 77.8 (CH), $_1$20.7 (CF$_3$), 131.4 (CH), 131.6 (CH), 132.8 (CH), 134.5 (CH), 134.8 (C); mp 174-176° C.; [α]$^{22}_D$ −21.7 (c 1, MeOH); $^{19}$F NMR (470.4 MHz, CD$_3$CN) δ: +35.4 (s, NF$^+$), −79.7 (s, CF$_3$SO$_3^-$). The structure of compound 29 is depicted in paragraph [0060] above.

Example 31

(S)-2-Amino-3-phenylpropanamide 30

To a solution of L-Phenylalanine methyl ester hydrochloride (26.1 g, 121 mmol, 1 eq) in chloroform (200 ml) was added saturated NaHCO$_3$ solution until pH paper indicated the solution to be basic. The free amine was extracted with chloroform (2×200 ml), dried over MgSO$_4$ and evaporated under reduced pressure. The resulting L-Phenylalanine methyl ester was dissolved in toluene (300 ml) and to this solution was added saturated ammonium hydroxide solution (150 ml). The reaction was stirred at room temperature for 24 hours before being evaporated to dryness under reduced pressure. The crude product did not require further purification (19.5 g, 119 mmol, 98%).

$^1$H NMR (400 MHz, DMSO): δ=1.90 (brs, 2H, NH$_2$), 2.59 (dd, J=13.4 Hz, 8.3 Hz, 1H), 2.92 (dd, J=13.4 Hz, J=5.1 Hz, 1H), 3.34 (dd, J=8.3 Hz, 5.1 Hz, 1H), 6.96 (brs, 1H), 7.16-7.30 (m, 5H), 7.32 (brs, 1H); $^{13}$C NMR (100.6 MHz, CDCl$_3$): δ=42.0, 57.1, 126.9, 128.9, 130.2, 139.8, 177.6.

Example 32

(R)-2-amino-3-phenylpropanamide 31

To a solution of L-Phenylalanine methyl ester hydrochloride in chloroform (200 ml) was added saturated NaHCO$_3$ solution until pH paper indicated the solution to be basic. The free amine was extracted with chloroform (2×200 ml), dried over MgSO$_4$ and evaporated under reduced pressure. The resulting L-Phenylalanine methyl ester was dissolved in toluene (300 ml) and to this solution was added saturated ammonium hydroxide solution (150 ml). The reaction was stirred at room temperature for 24 hours before being evaporated to dryness under reduced pressure. The crude product did not require further purification (19.5 g, 119 mmol, 98%).

H NMR (400 MHz, DMSO): δ=1.90 (brs, 2H, NH$_2$), 2.59 (dd, J=13.4 Hz, 8.3 Hz, 1H), 2.92 (dd, J=13.4 Hz, J=5.1 Hz, 1H), 3.34 (dd, J=8.3 Hz, 5.1 Hz, 1H), 6.96 (brs, 1H), 7.16-7.30 (m, 5H), 7.32 (brs, 1H); $^{13}$C NMR (100.6 MHz, CDCl): δ=42.0, 57.1, 126.9, 128.9, 130.2, 139.8, 177.6.

Example 33

(S)—N,N'-(3-Phenylpropane-1,2-diyl)bis(2-chloroacetamide) 32

To a solution of LiAlH$_4$ (13.9 g, 365 mmol) in THF (250 ml) at 0° C. in a 1 L flask was carefully added (R)-2-amino-3-phenylpropanamide (17.7 g, 108 mmol) and the reaction was heated at reflux for 8 hours before being cooled to 0° C. and quenched with 1% KOH (dropwise addition). The reaction mixture was then filtered through a pad of celite and washed with THF. The solvent was evaporated under reduced pressure and the product purified by vacuum distillation (0.25 mmHg, 86-88° C.) to afford the diamine as a colourless liquid (10.0 g). To a solution of this intermediate (1.00 g, 6.67 mmol) in DCM (100 ml) at 0° C. was added triethylamine (4.65 ml, 33.4 mmol), DMAP (41 mg) and chloroacetal chloride (1.59 ml, 20.0 mmol) dropwise. The reaction was warmed to room temperature and stirred for 3 hours before quenching with NaHCO$_3$ (100 ml), stirred for 1 hour, extracted into DCM (2×100 ml), dried over MgSO$_4$ and evaporated under reduced pressure. The crude residue was redissolved in DCM (200 ml), washed with 2M HCl (2×100 ml), then water (100 ml), dried over MgSO$_4$ and evaporated under reduced pressure to afford the title compound as a brown solid (1.93 g, 6.40 mmol, 96% yield).

$^1$H NMR (400 MHz, CDCl$_3$): δ=2.82 (dd, J=13.8 Hz, J=7.5 Hz, 1H), 2.98 (dd, J=6.3 Hz, 1H), 3.39-3.50 (m, 2H), 4.01 (d, J=3.1 Hz, 2H), 4.05 (d, J=1.3 Hz, 2H), 4.27-4.35 (m, 1H), 6.98 (brs, 1H, NH), 7.00 (brs, 1H, NH), 7.22 (d, J=7.3 Hz, 2H), 7.26 (t, J=7.2 Hz, 1H), 7.33 (t, J=7.5 Hz, 2H); $^{13}$C NMR (100.6 MHz, CDCl$_3$): δ=38.4, 42.4, 42.5, 43.3, 51.7, 127.1, 128.9, 129.1, 136.4, 166.7, 167.2; HRMS (ESI$^+$): N/Z CLACD FOR [c$_{13}$h$_{16}$Cl$_2$N$_2$NaO$_2$]$^+$(M+Na)$^+$: 325.0481, found 325.0474; IR (v, cm$^{-1}$): 3055 (NH), 2987 (NH), 1673 (NC=O).

Example 34

(R) 3-benzyl-1-(2-chloroethyl)piperazine 33

To a solution of (R)—N,N'-(3-phenylpropane-1,2-diyl)bis(2-chloroacetamide) (200 mg, 0.66 mmol) in THF (5 ml) at 0° C. was added BH$_3$. THF (1 M, 2.64 ml, 2.64 mmol). The reaction was heated at reflux overnight before being cooled to room temperature and quenched with methanol. After 30 minutes the solution was concentrated in vacuo. Purification by flash chromatography (SiO$_2$, MeOH/CHCl$_3$ 1:19) afforded the title compound as a pale yellow oil (144 mg, 0.60 mmol, 91% yield).

$^1$H NMR (400 MHz, CDCl$_3$): δ=2.49 (dd, J=12.0 Hz, J=9.8 Hz, 1H), 2.69 (t, J=6.6 Hz, 2H), 2.74 (t, J=11.9 Hz, 2H), 2.88 (td, J=12.1 Hz, J=6.1 Hz, 1H), 2.98 (t, J=11.7 Hz, 1H), 3.03-3.18 (m, 2H), 3.39 (dt, J=13.1 Hz, J=3.8 Hz, 2H), 3.43 (t, J=6.7 Hz, 2H), 7.16-7.30 (m, 5H); $^{13}$C NMR (100.6 MHz, CDCl$_3$): δ=36.7, 40.6, 43.3, 49.2, 54.1, 56.5, 58.9, 127.2, 128.9, 129.2, 135.3; IR (v, cm$^{-1}$): 3054 (NH); HRMS (ESI$^+$, m/z): [C$_{13}$H$_{20}$ClN$_2$]$^+$(M+H)$^+$calc. 239.1310, found 239.1310.

Example 35

(2S)-2-Benzyl-1,4-diazabicyclo[2.2.2]octane 34

To a solution of (R)—N,N'-(3-phenylpropane-1,2-diyl)bis(2-chloroacetamide)(200 mg, 0.66 mmol) in THF (5 ml) at 0° C. was added BH$_3$. THF (1 M, 2.64 ml, 2.64 mmol). The reaction was heated at reflux overnight before being cooled to room temperature and quenched with methanol. After 30 minutes the solution was concentrated in vacuo. Purification by flash chromatography (SiO2, MeOH/CHCl$_3$ 1:19) afforded the piperazine as a pale yellow oil (144 mg).

This intermediate (100 mg, 0.42 mmol) was heated to reflux in DMF (5 ml) and stirred overnight before being cooled to room temperature and concentrated in vacuo. The residue was dissolved in 1M NaOH (5 ml), extracted into chloroform (3×15 ml), dried over MgSO$_4$ and evaporated.

Purification by flash chromatography (SiO2, 1:9 MeOH/CHC13) afforded product 7 as a yellow oil (34 mg, 0.17 mmol, 36% yield over two steps).

$^1$H NMR (500 MHz, CDCl$_3$): δ=2.45 (ddd, J=13.1 Hz, J=6.7 Hz, J=1.9 Hz, 1H), 2.64-2.81 (m, 6H), 2.81-2.86 (m, 1H), 2.86 (dd, J=8.9 Hz, J=1.9 Hz, 1H), 2.90 (td, J=9.2 Hz, 1.8 Hz, 1H), 2.92-2.98 (m, 1H), 2.98-3.04 (m, 1H), 3.07-3.14 (m, 1H), 7.19-7.23 (m, 3H), 7.27-7.32 (m, 2H); $^{13}$C NMR (125 MHz, CDCl$_3$): δ=39.8, 40.9, 46.1, 47.3, 49.8, 53.8, 56.3, 126.3, 128.5, 128.9, 138.8; HRMS (ESI$^+$): m/z calcd [C$_{13}$H19N2]$^+$(M+H)$^+$: 203.1544, found 203.1543.

Example 36

(S)-3-Benzyl-1-(chloromethyl)-4-aza-1-azoniabicyclo[2.2.2]octane chloride 35

(S)-2-Benzyl-1,4-diazabicyclo[2.2.2]octane (300 mg, 1.48 mmol) was dissolved in DCM (5 ml) and left under argon, without stirring, for 96 hours. Removal of the solvent under reduced pressure afforded the product as a solid (426 mg, 1.48 mmol, quantitative yield).

$^1$H NMR (400 MHz, MeOD): δ=2.91 (dd, J=13.8 Hz, 7.8 Hz, 1H), 3.03 (dd, J=13.8 Hz, J=7.1 Hz, 1H), 3.15-3.22 (m, 2H), 3.29 (t, J=7.8 Hz, 2H), 3.40-3.66 (m, 7H), 5.18 (d, J=9.9 Hz, 1H), 5.23 (d, J=9.9 Hz, 1H), 7.22-7.28 (m, 1H), 7.29-7.35 (m, 4H); $^{13}$C NMR (125 MHz, CDCl$_3$): δ=37.6, 39.3, 46.6, 50.9, 51.9, 55.6, 56.9, 68.1, 126.9, 128.7, 129.2, 137.1; HRMS (ESI$^+$M): m/z calcd for [C$_{14}$H$_{20}$ClN$_2$]$^+$(M)$^+$: 251.1306, found 251.1310.

Example 37

(S)-3-Benzyl-1-(chloromethyl)-4-aza-1-azoniabicyclo[2.2.2]octane tetrafluoroborate 36

To a solution of (S)-3-benzyl-1-(chloromethyl)-4-aza-1-azoniabicyclo[2.2.2]octane chloride (27) (200 mg, 0.70 mmol) in acetonitrile (5 ml) at it was added lithium tetrafluoroborate (65 mg, 0.70 mmol) and the reaction was stirred for 24 hours before filtering and concentrating in vacuo. Recrystallising twice from methanol/ether afforded the title compound as a grey solid (237 mg, 0.70 mmol, 99% yield).

$^1$H NMR (400 MHz, MeOD): δ=2.90 (dd, J=13.9 Hz, J=7.9 Hz, 1H), 3.02 (dd, J=13.9 Hz, J=7.2 Hz, 1H), 3.13-3.21 (m, 2H), 3.28 (t, J=7.6 Hz, 2H), 3.39-3.65 (m, 7H), 4.86 (s, 2H), 5.12 (d, J=9.9 Hz, 1H), 5.17 (d, J=9.9 Hz, 1H), 7.21-7.27 (m, 1H), 7.28-7.34 (m, 4H); $^{13}$C NMR (125 MHz, CDCl$_3$): δ=37.6, 39.3, 46.6, 50.8, 51.9, 55.5, 56.9, 68.0, 126.9, 128.7, 129.2, 137.1; $^{19}$F NMR (376.6 MHz, CDCl$_3$): δ=−153.7; HRMS (ESI$^+$): m/z calcd for [C$_{14}$H$_{20}$ClN$_2$]$^+$(M)$^+$: 251.1306, found 251.1310.

Example 38

(R)-1-Phenylethane-1,2-diamine 37

(R)-1-phenylethane-1,2-diamine was prepared following a 2 step procedure. To a solution of (R)-(−)-2-phenylglycine methyl ester hydrochloride (8.5 g, 51.52 mmol) in toluene (100 mL) was added an aqueous solution of NH$_4$OH (28% in water, 50 mL) and the mixture was stirred at room temperature for 24 h. The solvent was evaporated and the solid obtained was dried affording 7.09 g (92% conversion) of (R)-2-amino-2-phenylacetamide.

To a suspension of lithium aluminium hydride (LiAlH$_4$) (5.4 g, 141.80 mmol) in tetrahydrofuran (150 mL) at 0° C. was added portionwise (R)-2-amino-2-phenylacetamide (7.09 g, 47.26 mmol). The reaction was stirred at 0° C. for 10 minutes and then heated at reflux overnight. The mixture was cooled to 0° C. and then quenched by the careful addition of water and NaOH 1 M. The mixture was stirred for 10 minutes until a white precipitate was observed, filtered through celite and evaporated. The residue was purified by distillation affording 2.02 g (32% yield) of (R)-1-phenylethane-1,2-diamine.

Example 39

(R)—N,N'-(1-Phenylethane-1,2-diyl)bis(2-chloroacetamide) 38

The crude mixture after reduction with LiAlH$_4$ (3.10 g, 22.79 mmol) was dissolved in dichloromethane (120 mL) and 4-dimethylaminopyridine (95 mg, 0.775 mmol), triethylamine (16 mL, 114 mmol) and chloroacetyl chloride (5.4 mL, 68.40 mmol) were added sequentially at 0° C. and the solution was stirred at room temperature overnight. Water and HCl 1 M were added, stirred for 15 minutes and then extracted with dichloromethane. The combined organic extracts were dried, filtered and evaporated and the residue was purified by silica gel flash column chromatography (Hexane:ethyl acetate, from 1:1 to 3:7) affording 2.96 g (34% yield after 2 steps) of (R)—N,N'-(1-phenylethane-1,2-diyl)bis(2-chloroacetamide). $^1$H NMR (400 MHz, MeOD) δ 3.58 (dd, J=8.3, 6.0 Hz, 2H, CH$_2$), 4.02 (s, 2H, CH$_2$Cl), 4.06 (s, 2H, CH$_2$Cl), 5.13 (dd, J=8.1, 6.2 Hz, 1H, CH), 7.26-7.31 (m, 1H), 7.34-7.37 (m, 4H); $^{13}$C NMR (100.6 MHz, MeOD) δ 43.2, 43.4, 45.5, 55.3, 127.9, 127.9, 129.0, 129.9, 129.9, 140.6, 169.2, 170.1; IR (neat) (v, cm$^{-1}$) 3312, 1642, 1533, 1262; HRMS required for C$_{12}$H$_{14}$Cl$_2$N$_2$NaO$_2$ ([M+Na]$^+$): 311.0325, found 311.0326; [α]$^{22}_D$−50 (c 0.53, MeOH); mp 112-113° C.

Example 40

(R)-2-Phenyl-1,4-diazabicyclo[2.2.2]octane 39

To a solution of (R)—N,N'-(1-phenylethane-1,2-diyl)bis(2-chloroacetamide) (500 mg, 1.73 mmol) in THF (22 mL) at 0° C. was added dropwise BH$_3$.THF (1M in THF, 7 mL, 6.95 mmol) and the reaction was heated at reflux for 12 hours. The reaction mixture was cooled to room temperature and MeOH was added dropwise to consume the remaining BH$_3$.THF and stirred for 12 hours at room temperature. Then the solvent was evaporated, HCl 2M was added and the mixture was stirred at the same temperature for 12 more hours. NaOH 3M was added to bring the reaction mixture to pH 14 and was extracted with dichloromethane. The combined organic extracts were dried, filtered and evaporated to give 411 mg of a crude which was used in the next step with no further purification.

The crude product (411 mg) was dissolved in dimethylformamide (25 mL) and heated at 150° C. for 12 hours. The solvent was evaporated, water and NaOH 3M were added until reach pH 14 and extracted with dichloromethane. The combined organic extracts were dried, filtered and evaporated and the residue was purified by silica gel flash column chromatography (chloroform:methanol, 95:5 then 50:50) affording 65 mg (20% yield after 2 steps) of (R)-2-phenyl- 1,4-diazabicyclo[2.2.2]octane. $^1$H NMR (400 MHz, CDCl$_3$) δ 2.48-2.54 (m, 1H, CH$_2$), 2.60 (t, J=7.0 Hz, 2H, CH$_2$), 2.67-2.74 (m, 3H), 2.85-2.97 (m, 3H), 3.29 (dd, J=9.6, 9.6 Hz, 1H, CH$_2$), 3.83 (t, J=8.6 Hz, 1H, CH), 7.13-7.17 (m, 1H), 7.23-7.28 (m, 4H); $^{13}$C NMR (100.6 MHz, CDCl$_3$) δ 40.9, 46.4, 47.1, 49.2, 52.9, 56.4, 126.5, 126.8, 126.8, 128.1, 128.1, 141.2; IR (neat) (ν, cm$^{-1}$) 2869, 1454, 1067; HRMS required for C$_{12}$H$_{17}$N$_2$ ([M+H]$^+$): 189.1386, found 189.1390. [α]$^{22}_D$-82 (c 0.11, MeOH); mp 64-65° C.

Example 41

(3R)-1-(Chloromethyl)-3-phenyl-4-aza-1-azoniabicyclo[2.2.2]octane chloride 40

Starting from (R)—N,N-(1-phenylethane-1,2-diyl)bis(2-chloroacetamide) (1.72 g, 5.97 mmol) and after reduction with BH$_3$.THF and cyclization in DMF the crude (R)-2-phenyl-1,4-diazabicyclo[2.2.2]octane (652 mg) was dissolved in dichloromethane (5 mL) and dry acetone (5 mL) and was stirred at room temperature for 2 weeks while monitoring by mass spectrometry. The final suspension was filtered off on filter paper and the solid was rinsed with hexane and dried to afford 255.7 mg (16% yield in 3 steps) of (3R)-1-(chloromethyl)-3-phenyl-4-aza-1-azoniabicyclo [2.2.2]octane chloride. $^1$H NMR (500 MHz, CD$_3$CN) δ 2.94-3.01 (m, 1H, CH$_2$), 3.04-3.09 (m, 1H, CH$_2$), 3.35 (dt, J=13.5, 8.8 Hz, 1H, CH$_2$), 3.43-3.55 (m, 2H, CH$_2$), 3.62-3.67 (m, 3H, CH$_2$), 3.87 (t, J=10.4 Hz, 1H, CH$_2$), 4.20 (ddd, J=12.3, 9.5, 3.0 Hz, 1H, CH$_2$), 4.51 (t, J=9.0 Hz, 1H, CH), 5.53 (d, J=9.6 Hz, 1H, CH$_2$Cl), 5.60 (d, J=9.6 Hz, 1H, CH$_2$Cl), 7.35 (t, J=7.3 Hz, 1H), 7.41-7.47 (m, 4H); $^{13}$C NMR (125.8 MHz, CD$_3$CN) δ 40.6, 46.8, 51.7, 52.6, 56.4, 56.7, 68.9, 127.9, 127.9, 129.0, 129.7, 129.7, 138.8; IR (neat) (ν, cm$^{-1}$) 2957, 1658, 1097; HRMS required for C$_{13}$H$_{18}$ClN$_2$ ([M]$^+$): 237.1153, found 237.1157; [α]$^{22}_D$-17 (c 0.57, MeOH); mp 147-148° C.

Example 42

(3R)-1-(Chloromethyl)-3-phenyl-4-aza-1-azoniabicyclo[2.2.2]octane trifluoromethanesulfonate 41

A solution of (3R)-1-(chloromethyl)-3-phenyl-4-aza-1-azoniabicyclo[2.2.2]octane chloride (200 mg, 0.84 mmol) and sodium trifluoromethanesulfonate (145 mg, 0.84 mmol) in acetonitrile (12 mL) was stirred for 46 h at room temperature. The solvent was evaporated, 3 mL of dry acetonitrile was added and the suspension was filtered. The solid was rinsed twice with acetonitrile (2×5 mL) and the filtrate was evaporated to afford 282 mg (99% yield) of (3R)-1-(chloromethyl)-3-phenyl-4-aza-1-azoniabicyclo[2.2.2]octane trifluoromethanesulfonate. $^1$H NMR (400 MHz, CD$_3$CN) δ 2.95-3.04 (m, 1H, CH$_2$), 3.07-3.14 (m, 1H, CH$_2$), 3.27-3.39 (m, 3H, CH$_2$), 3.40-3.51 (m, 4H, CH$_2$), 4.05 (ddd, J=12.1, 9.5, 2.7 Hz, 1H, CH$_2$), 4.50 (t, J=9.0 Hz, 1H, CH), 5.03 (d, J=10.0 Hz, 1H, CH$_2$Cl), 5.07 (d, J=10.0 Hz, 1H, CH$_2$Cl), 7.34-7.46 (m, 5H); $^{13}$C NMR (125.8 MHz, CD$_3$CN) δ 40.6, 46.7, 52.1, 53.1, 56.4, 57.1, 69.3, 127.6, 127.6, 129.1, 129.8, 129.8, 138.6; $^{19}$F {1H} NMR (376.6 MHz, CD$_3$CN) δ-79.2; IR (neat) (ν, cm$^{-1}$) 1249, 1156, 1028; HRMS required for C$_{13}$H$_{18}$ClN$_2$ ([M]$^+$): 237.1153, found 237.1150; MS-EI$^-$ m/z 148.94 (OTf); [α]$^{22}_D$-11 (c 0.94, MeOH).

X-Ray Crystollagraphy General Procedure

A typical single crystal was chosen and was mounted on a hair using perfluoropolyether oil and cooled rapidly to 150 K in a stream of cold N$_2$ using an Oxford Cryosystems Cryostream N$_2$ open flow-cooling device. Diffraction data were measured using an Enraf-Nonius KappaCCD diffractometer (graphite-monochromated MoKα radiation, λ=0.71073 Å) to a maximum resolution of 0.77 Å. Intensity data were processed using the DENZO-SMN package and were corrected for absorption and other effects using SCALEPACK. The systematic absences in the intensity data were examined to determine the space group (P212121). The structures were solved using the direct-methods program SIR92, which located all non-hydrogen atoms. Subsequent full-matrix least-squares refinement was carried out using the CRYSTALS program suite to refine coordinates and anisotropic thermal parameters of all non-hydrogen atoms. Hydrogen atoms were located in the difference map and refined before being added to the model using a riding constraint.

Example 43

(2R,3R)-1-methyl-2,3-diphenyl-4-aza-1-azoniabicyclo[2.2.2]octane trifluoromethanesulfonate 27

(2R,3R)-1-methyl-2,3-diphenyl-4-aza-1-azoniabicyclo [2.2.2]octane trifluoro-methanesulfonate (30 mg) was dissolved in methanol (3 ml). After standing for 24 h, suitable crystals formed gradually.

| | |
|---|---|
| Crystal identification | 027JOI01 |
| Chemical formula (sum) | C$_{20}$H$_{23}$F$_3$N$_2$O$_3$S |
| Chemical formula (moiety) | C$_{19}$H$_{23}$N$_2$, CF$_3$O$_3$S |
| Formula weight | 428.47 |
| Temperature (K) | 150 |
| Wavelength (Å) | 0.71073 |
| Crystal system | Orthorhombic |
| Space group name | P 21 21 21 |
| Space group hall | P 2ac 2ab |
| a (Å) | 8.1290(2) |
| b (Å) | 15.2413(3) |
| c (Å) | 16.1054(4) |
| α (°) | 90 |
| β (°) | 90 |
| γ (°) | 90 |
| Cell volume (Å$^3$) | 1995.40(8) |
| Flack | -0.01(6) |

Examples 44 to 47

Examples 44 to 46 use a mono-quaternised DABCO analogue as an enantioselective fluorinating agent to model the di-quaternised fluorinating agents of the invention as regards enantioselectivity. The mono-quaternised DABCO analogue is (R,R)—N-fluoro-2,3-diphenyl-1,4-diazabicyclo [2.2.2]octane (42) and has the structure:

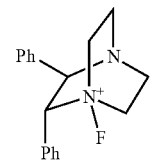

(42)

The mono-quaternised DABCO analogue (42) can be pre-prepared or made in situ by reacting a DABCO analogue (3a):

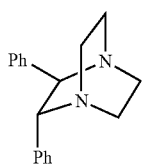

(3a)

with SelectFluor.

Example 44

The following example provides a comparison between (i) an enantioselective fluorination reaction using Selectfluor and dihydroquinine 4-chlorobenzoate (DHQB) (first reaction); and (ii) a mixture of Selectfluor and the DABCO analogue (3a) (second reaction). As illustrated, both the yield and the enantiomeric excess is much higher for the second reaction than for the first reaction.

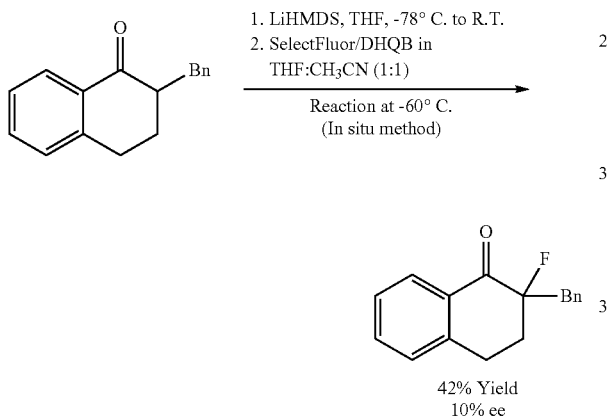

Example 45

The following example provides a comparison between (i) an enantioselective fluorination reaction using Selectfluor and dihydroquinine 4-chlorobenzoate (DHQB) (first reaction); and (ii) the mono-quaternised DABCO analogue (42) (second reaction). As illustrated, both the yield and the enantiomeric excess is much higher for the second reaction than for the first reaction.

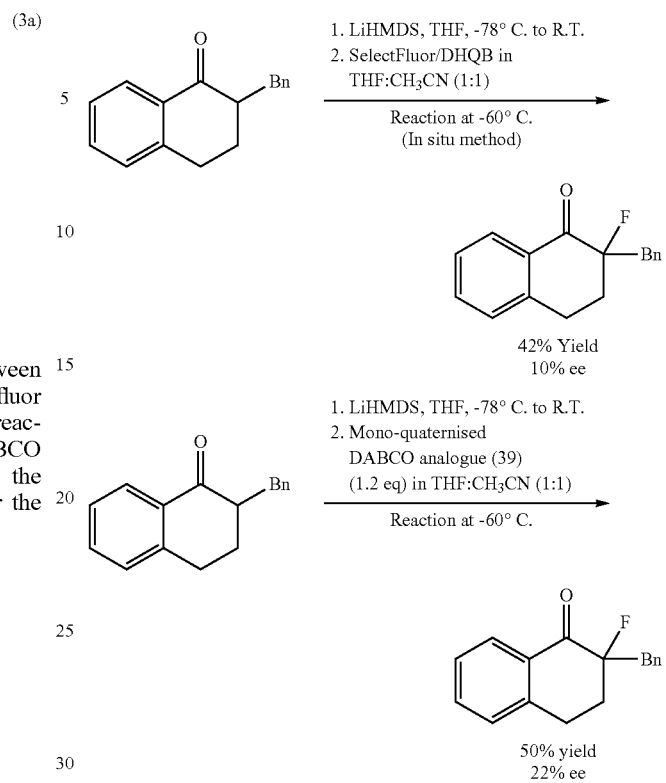

Example 46

The following example provides a comparison between (i) an enantioselective fluorination reaction using Selectfluor and dihydroquinine 4-chlorobenzoate (DHQB) (first reaction); and (ii) a mixture of Selectfluor and the DABCO analogue (3a) (second reaction). As illustrated, both the yield and the enantiomeric excess is much higher for the second reaction than for the first reaction.

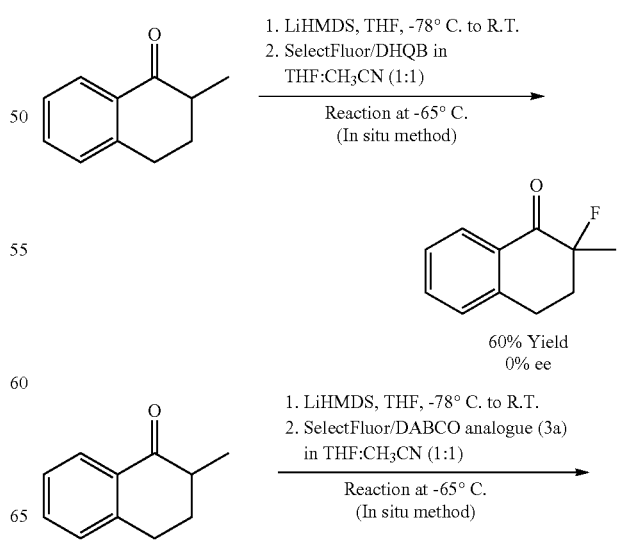

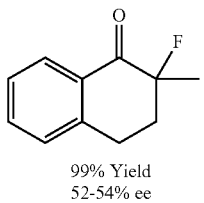

99% Yield
52-54% ee

Example 47

The following example provides a comparison between (i) an enantioselective fluorination reaction using Selectfluor and dihydroquinine 4-chlorobenzoate (DHQB) (first reaction); and (ii) the mono-quaternised DABCO analogue (42) (second reaction). As illustrated, both the yield and the enantiomeric excess is much higher for the second reaction than for the first reaction.

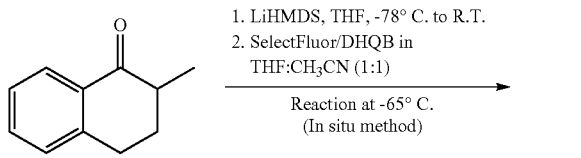

60% Yield
0% ee

90% yield
11% ee

Fluorination Reactions—General Procedures

Preparation of the Fluorinating Reagent

A solution of Selectfluor was added to a solution of (R,R)-3a at −80° C.; the resulting solution was left to stir at this temperature for 15 min. For achiral reactions with Selectfluor as the fluorinating reagent crude product mixtures were directly subjected to chiral HPLC after work-up, for all other systems the crude product mixture was filtrated through neutral alumina eluting with $Et_2O$ to remove the chiral transfer reagent.

Fluorinations of In Situ Prepared Enolates

To a solution of the starting material (20 mg, 1 eq) in THF (1 mL) at −78° C. LiHMDS (1M solution in THF, 1.5 eq.) was added. The resulting solution was stirred for 5 min, then warmed to it and stirred for 45 min. The solution was cooled down to −78° C. and added to a solution of the fluorinating reagent (1.2 eq.) in the solvent of choice (3 mL). The reaction mixture was brought to the temperature of interest and left stirring overnight. The reaction was quenched with sat. aq. $NH_4Cl$ (3 mL) and $Et_2O$ (5 mL) and warmed to rt. The aq. layer was extracted with $Et_2O$ and the combined organic layers were washed with water and brine, dried, filtered, and concentrated in vacuo.

Fluorinations of β-Keto Esters

To a solution of the fluorinating reagent (1.2 eq) in the solvent of choice (3 mL) a solution of the starting material (20 mg, 1 eq) in the respective solvent system (1 mL) was added at −78° C. and the solution stirred overnight at the temperature of interest. The reaction was quenched by the addition of water and warmed to rt. The product was extracted into DCM, and the combined organic layers dried, filtered and concentrated in vacuo.

2-Fluoro-2-methyl-3,4-dihydro-2H-naphthalen-1-one (43)[9]

A colourless oil was obtained. The two enantiomers were separated by HPLC (Chiralcel OB, hexane/iPrOH 90:10, 1 mL/min): 11.1 min (R) and 16.4 (S). $^1H$ NMR (400 MHz, $CDCl_3$) δ: 8.09-8.07 Hz (d, J=7.8 Hz, 1H, ArH), 7.55-7.51 (dt, J=7.6, 1.3 Hz, 1H, ArH), 7.38-7.34 (t, J=7.6 Hz, 1H, ArH), 7.28-7.26 (d, J=8.3 Hz, 1H, ArH), 3.15 (m, 1H, H), 3.02 (m, 1H, H), 2.49 (m, 1H, H), 2.29 (m, 1H, H), 1.63-1.58 (d, J=22.2 Hz, 3H, H). $^{13}C$ NMR (100.6 MHz, $CDCl_3$) δ: 194.2 (d, J=18.1 Hz, C), 142.7 (C), 134.0 (CH), 130.7 (C), 128.7 (CH), 128.3 (CH), 127.1 (CH), 93.8 (d, J=179.3 Hz, C), 35.0 (d, J=22.9 Hz, CH2), 26.2 (d, J=9.5 Hz, CH2), 20.9 (d, J=25.8 Hz, CH3). $^{19}F$ NMR (376 MHz, $CDCl_3$) δ: −152.4 Ppm. HRMS m/z calcd for $C_{11}H_{11}FO$ ([M+NH4]+): 196.1135, found 196.1135.

Fluorination of α-Methyl Tetralone with N-Fluorinated DABCO Derivative 3a

| Entry | Base | Fluorinating Reagent | Solvent | Conditions | Yield [%] | ee [%] |
|---|---|---|---|---|---|---|
| 1 | LiHMDS | 3a/Selectfluor (1/1) | THF/MeCN (1/1) | −65° C., 12 h | 99 (conversion) | 52-54 |
| 2 | LiHMDS | 3a/Selectfluor (1/1) | THF/MeCN (1/1) | −70° C., 12 h | 64 | 56 |
| 3 | LiHMDS | 3a/Selectfluor (1/1) | THF/MeCN (1/1) | −75° C., 12 h | 66 | 40 |

2-Ethoxycarbonyl-2-fluoro-1-indanone (44)[9]

The fluorination of 2-ethoxy-1-indanone with N-fluorinated was achieved using LiHMDS as the base, 3a/Selectfluor in a 1:1 ratio as a fluorinating agent, THF/MeCN is a 1:1 ratio as the solvent and the reaction was carried out at −78° C. for 12 hours. The yield was 100% (conversion) and the ee was 20%.

A colourless oil was obtained. Separation of the enantiomers was achieved by HPLC (Chiralcel OJ-H, hexane: iPrOH 90:10, 1 mL/min), major enantiomer: 22 min, minor: 36 min). $^1$H NMR (500 MHz, CDCl$_3$) δ: 7.86-7.84 (m, 1H, ArH), 7.73-7.69 (m, 1H, ArH), 7.53-7.49 (m, 2H, ArH), 4.31-4.27 (q, J=7.3 Hz, 2H, H), 3.83-3.77 (dd, $^2$JH-H=17.7 Hz, $^3$J$_{H-F}$ 11.7 Hz, 1H, H), 3.48-3.40 (dd, $^2$J$_{H-H}$=17.7 Hz, $^3$J$_{H-F}$=23.3 Hz, 1H, H), 1.29-1.26 (t, J=7.3 Hz, 3H, H); $^{13}$C NMR (125.5 MHz, CDCl$_3$) δ: 195.2 (d, J=18.1 Hz, C), 167.3 (d, J=27.7 Hz, C), 150.9 (C), 136.7 (CH), 133.3 (C), 128.6 (CH), 126.6 (CH), 125.6 (CH), 94.5 (d, J=202.2 Hz, C), 62.6 (CH2), 38.3 (d, J=23.9 Hz, CH$_3$); $^{19}$F NMR (376 MHz, CDCl3) δ: −164.4; MS−EI m/z 245.1 ([M+Na]$^+$, 50), 281.2 (100), 467.1 (65).

Further Reactions

The following further reactions were also carried out:

Fluorodesilylation of alkenyl trimethylsilane 45

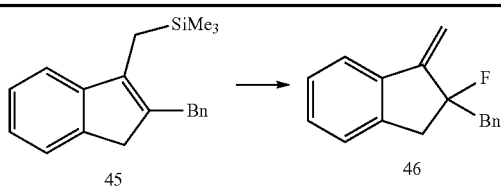

| Entry | Reagents | Solvent | Conditions | Yield [%] | ee [%] |
|---|---|---|---|---|---|
| 1 | 14a | MeCN | −20° C., 3 h | 80 | 29 |

Fluorination of silyl enol either 47

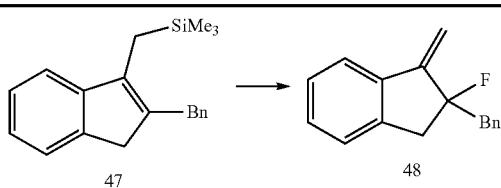

| Entry | Reagents | Solvent | Conditions | Yield [%] | ee [%] |
|---|---|---|---|---|---|
| 1 | 14a | MeCN | −20° C., 3 h | 85 | 30 |

Fluorocyclisation of substituted indene 49

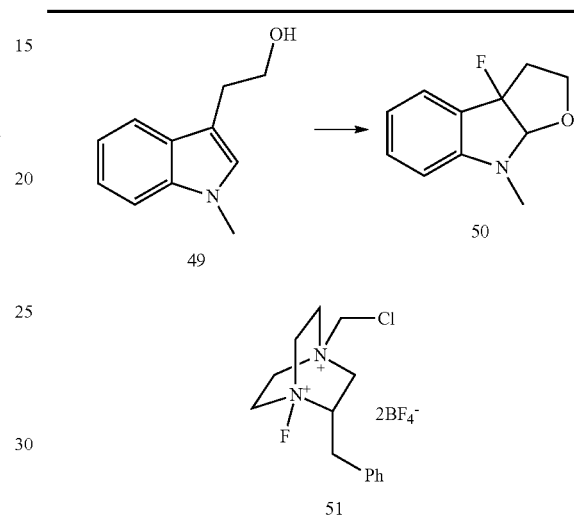

| Entry | Reagents | Solvent | Conditions | Conversion [%] | ee [%] |
|---|---|---|---|---|---|
| 1 | 36(1.2 eq), NaHCO$_3$ | MeCN | r.t., overnight | 58 | 8 |
| 2 | 51/ N-fluoropentachloropyridinium triflate (1/1, 1.2 eq), NaHCO$_3$ | MeCN | r.t., overnight | 59 | 9 |

Compound 51 was prepared by mixing compound 36 with LiBF$_4$ in MeCN at room temperature for 24 hours.

Example 48

(2S,3R)-Methyl 2-amino-3-(benzyloxy)butanoate hydrochloride 52

Following the same procedure as for 18, the target compound 39 was obtained from (2S,3R)-2-amino-3-(benzyloxy)butanoic acid trifluoroacetate (26.0 g, 80.5 mmol) as a yellow solid (21 g, quant.).

$^1$H NMR (200 MHz, DMSO) δ=1.28 (d, J=6.40 Hz, 3 H) 3.69 (s, 3 H) 4.05 (m, J=5.93, 3.03 Hz, 1 H) 4.20 (br. s., 1H) 4.42 (d, J=11.86 Hz, 1 H) 4.59 (d, J=12.03 Hz, 1 H) 7.15-7.50 (m, 5 H) 8.48 (br. s., 2 H); $^{13}$C NMR (101 MHz, MeOD): δ=16.6, 54.2, 59.2, 72.2, 73.0, 129.2, 129.4, 129.6, 138.8, 169.4; HRMS (ESI)$^+$: m/z calcd for C$_{12}$H$^{18}$NO$_3$[M+1-1]$^+$: 224.1281, found 224.1279; mp: 100° C.; [α]$^{22}_D$=−34.4 (c=0.5, MeOH).

Example 49

(2S,3R)-2-Amino-3-(benzyloxy)butanamide 53

To a solution of (2S,3R)-methyl 2-amino-3-(benzyloxy) butanoate hydrochloride (22.1 g, 85.2 mmol) in chloroform (100 ml) was added saturated aqueous NaHCO$_3$ (100 ml) basified with NaOH pellets to pH 12. The free amine was extracted with chloroform (3×200 ml), dried over MgSO$_4$ and evaporated under reduced pressure to give a brown oil (17.53 g). The free amine was dissolved in toluene (8 ml) and saturated aqueous NH$_4$OH (38 ml) was added. The reaction was stirred in a sealed tube at rt, then at 60° C. for 24 hours each. After evaporation of the solvent, the brown residue was extracted with chloroform (200 ml) and 0.1 M aqueous Na$_2$CO$_3$ solution. The aqueous layer was washed with chloroform (3×200 ml) and the organic layers were combined, dried with MgSO$_4$ and evaporated to dryness to afford 40 as a brown solid (11.8 g, 56.7 mmol, 72%).

$^1$H NMR (250 MHz, MeOD) δ=1.29 (d, J=4.87 Hz, 3 H) 3.94 (br. s., 1 H) 4.52 (d, J=11.57 Hz, 1 H) 4.65 (d, J=11.27 Hz, 1 H) 7.37 (br. s., 5 H); $^{13}$C NMR (101 MHz, MeOD) δ=16.8, 60.5, 72.4, 77.5, 128.8, 129.0, 129.5, 140.0, 178.6; IR (ν, cm$^{-1}$): 3399 (NH), 3220 (NH), 1673 (NC=O); [α]$^{22}_D$=−49.2 (c=0.25, MeOH); HRMS (ESI): m/z calcd for C$_{11}$H$_{17}$N$_2$O$_2$ [M+1-1]$^+$: 209.1285, found 209.1282.

Example 50

(2S,3R)—N,N'-(3-Benzyloxybutane-1,2-diyl)bis(2-chloroacetamide) 54

(2S,3R)-2-amino-3-(benzyloxy)butanamide (9.36 g, 44.96 mmol, 1 eq) was dissolved in dry THF (70 mL) over activated molecular sieves under argon and cooled to 0° C. BH$_3$.THF (1 M solution in THF, 225 mL, 224.8 mmol, 5 eq) was added dropwise and the solution was stirred under reflux conditions for 24 hours. After cooling to 0° C., methanol (15 mL) was added slowly and the mixture stirred at it for 3 hours. The solvent was evaporated and the residue treated with 6 N HCl (20 mL) for 2 hours under stirring. The solvent was removed, 1 M KOH (100 mL) were added to the residue and extracted with chloroform (4×80 mL). The organic layers were dried with MgSO$_4$ and evaporated to afford a brown oil (8.3 g). The amine (7.88 g, 40.58 mmol, 1 eq) was dissolved in dry dichloromethane (200 ml) under argon and cooled to 0° C. Triethylamine (28.3 mL, 206.9 mmol, 5 eq) followed by DMAP (248 mg, 2.069 mmol, 0.05 eq) and chloroacetyl chloride (9.7 mL, 121.7 mmol, 3 eq) were added and the dark solution was stirred at it for 8 hours. After quenching with NaHCO$_3$ (100 ml) and stirring for 1 hour at rt, the layers were separated and the aqueous layer extracted with DCM (3 x). The combined organic layers were washed with 1 M HCl and water, dried over MgSO$_4$ and evaporated under reduced pressure. After purification by flash chromatography (DCM/MeOH: 99/1), 41 was obtained as a colourless oil (7.27 g, 20.93 mmol, 48%).

$^4$H NMR (400 MHz, CDCl$_3$) δ=1.23 (d, J=6.32 Hz, 3 H), 3.45 (ddd, J=13.64, 8.08, 5.31 Hz, 1 H), 3.56 (m, 1 H), 3.75 (qd, J=6.23, 2.02 Hz, 1 H), 3.98 (d, J=2.78 Hz, 2 H), 4.07 (s, 2 H), 4.43 (d, J=11.62 Hz, 1 H), 4.68 (d, J=11.62 Hz, 1 H), 6.97-7.14 (m, 2 H), 7.28-7.43 (m, 5 H); $^{13}$C NMR (101 MHz, CDCl$_3$) δ=16.3, 42.5, 53.5, 70.7, 73.4, 127.9, 128.0, 128.5, 137.6, 166.6, 167.0; HRMS (ESI)$^+$: m/z calcd for C$_{15}$H$_{20}$Cl$_2$N$_2$NaO$_3$ [M+Na]$^+$: 369.0743, found 369.0730; IR (ν, cm$^{-1}$): 3316 (NH), 1662 (NCO), 1540 (NH); R$_1$: 0.63 (EtOAc/Hexane=7/3); [α]$^{22}_D$=22.4 (c=0.25, CHCl$_3$).

Example 51

(S)-2-((R)-1-(Benzyloxy)ethyl)-1,4-diaza-bicyclo[2.2.2]octane 55

(2S,3R)—N,N'-(3-benzyloxybutane-1,2-diyl)bis(2-chloroacetamide) (2.77 g, 7.98 mmol, 1 eq) was dissolved in dry THF (160 ml) over activated molecular sieves under argon and cooled to 0° C. BH$_3$.THF (1 M solution in THF, 32 ml, 31.9 mmol, 4 eq) was added dropwise and the solution was stirred under reflux conditions overnight. After cooling to rt, MeOH (40 ml) was added and stirring was continued for 3 hours. The solvent was evaporated and the crude product dissolved in chloroform and extracted with 0.1 M Na$_2$CO$_3$. The aqueous layer was washed with DCM (3×), the combined organic layers were dried over MgSO$_4$ and evaporated to dryness to afford the crude diamine (2.08 g) as a yellow oil. Dry DMF (25 ml) was added and the solution was stirred at 110° C. overnight. After evaporation of the solvent under reduced pressure the crude product was purified by flash chromatography (CHCl$_3$/MeOH: 99.5/0.5-98/2+0.5% aq. NH$_3$) to afford the title compound as a yellow oil (840 mg, 3.41 mmol, 43%).

$^1$H NMR (250 MHz, CDCl) δ=1.15 (d, J=6.09 Hz, 3 H) 2.35 (dd, J=12.64, 7.16 Hz, 1 H) 2.49-2.78 (m, 6 H) 2.78-3.07 (m, 4 H) 3.38-3.58 (m, 1 H) 4.60 (d, J=12.49 Hz, 1 H) 4.71 (d, J=12.49 Hz, 1 H) 7.27-7.47 (m, 5 H); $^{13}$C NMR (63 MHz, CDCl$_3$) δ=16.2, 41.8, 46.4, 47.3, 49.7, 50.6, 60.4, 70.4, 73.3, 127.5, 127.9, 128.3, 138.8; HRMS (ESI)$^+$: m/z calcd for C$_{15}$H$_{23}$N$_2$O [M+1-1]$^+$: 247.1805, found 247.1803; R$_1$: 0.34 (DCM/MeOH=95/5+1% aq. NH$_3$ (25%)); [α]$^{22}_D$=14.2 (c=0.15, CHCl$_3$).

Example 52

(S)-2-((R)-1-(Naphthalen-1-yloxy)ethyl)-1,4-diaza-bicyclo[2.2.2]octane 56

To (S)-2-((R)-1-(benzyloxy)ethyl)-1,4-diaza-bicyclo [2.2.2]octane (155 mg, 0.63 mmol) in ethanol (10 ml) and concentrated HCl (0.6 ml) was added palladium hydroxide (20% on charcoal) (44 mg, 10 mol %). After stirring for 2 days under a H$_2$-atmosphere (1 atm), the reaction was filtered through a pad of celite and evaporated to dryness to give a sticky yellow solid.

The alcohol was dissolved in dry DMSO (4 ml) under argon and cooled to 0° C. in an ice-water bath. Sodium hydride (60% dispersed on oil, 83 mg, 2.1 mmol) was added carefully until the bubbling ceased. Copper iodide (120 mg, 0.63 mmol) and pyridine (0.15 ml, 1.2 mmol) were added and stirring was continued at room temperature for 1 h. 1-Iodonaphthalene (0.09 ml, 0.63 mmol) was added and the dark green solution was heated to reflux for 7 h. After cooling to room temperature, chloroform (10 ml) and water (10 ml) followed by ethylenediaminetetraacetate disodium salt dehydrate (350 mg) and concentrated aqueous ammonia solution (0.5 ml) were added and the mixture was stirred for 1 hour. The layers were separated, the aqueous layer washed with chloroform (3 times), the organic layers were combined, dried with MgSO$_4$ and evaporated to dryness. The crude oil was purified by flash chromatography (CHCl$_3$/MeOH: 99/1-98/2+0.5% aq. NH$_3$) to afford compound 43 (59 mg, 33 yield) as a brown oil.

$^1$H NMR (200 MHz, CDCl$_3$) δ=1.36 (d, J=6.14 Hz, 3H) 2.57-3.16 (m, 10H) 3.23-3.45 (m, 1H) 4.59-4.71 (m, J=6.21 Hz, 1H) 6.92 (dd, J=7.21, 1.15 Hz, 1H) 7.31-7.56 (m, 4H) 7.72-7.89 (m, 1H) 8.17-8.35 (m, 1H); $^{13}$C NMR (63 MHz, CDCl$_3$) δ=16.4, 42.5, 46.4, 47.4, 50.0, 59.8, 74.4, 107.3, 120.7, 122.5, 125.1, 125.7, 126.3, 127.5, 140.9; HRMS (ESI)$^+$: m/z calcd for C$_{18}$H$_{23}$N$_2$O [M+1-1]$^+$: 283.1810, found 283.1813, [α]$^{20}_D$=−9.3 (c=0.23, CHCl$_3$).

Example 53

(S)-2-((R)-1-(Benzyloxy)ethyl)-1-(chloromethyl)-1,4-diaza-bicyclo[2.2.2]octane chloride 57

(S)-2-((R)-1-(Benzyloxy)ethyl)-1,4-diaza-bicyclo[2.2.2]octane (602 mg, 2.48 mmol) was dissolved in dry dichloromethane (20 ml) and left at room temperature under argon, without stirring, for 108 hours. Removal of the solvent under reduced pressure afforded (S)-2-((R)-1-(benzyloxy)ethyl)-1-(chloromethyl)-1,4-diaza-bicyclo[2.2.2]octane chloride (757 mg, 93%) as a white solid.

$^1$H NMR (500 MHz, (CD$_3$)$_2$CO) δ 1.29 (d, J=6.31 Hz, 4H), 3.08-3.16 (m, 1H), 3.33 (t, J=7.72 Hz, 2H), 3.35-3.41 (m, 1H), 3.56-3.72 (m, 3H), 3.73-3.85 (m, 2H), 3.85-3.99 (m, 2H), 4.06 (ddd, J=11.66, 9.30, 3.00 Hz, 1H), 4.60 (d, J=11.66 Hz, 1H), 4.69 (d, J=11.66 Hz, 1H), 5.94 (d, J=9.46 Hz, 1H), 5.99 (d, J=9.46 Hz, 1H), 7.22-7.30 (m, 1H), 7.35 (t, J=7.57 Hz, 2H), 7.43 (d, J=7.57 Hz, 2H); $^{13}$C NMR (63 MHz, (CD$_3$)$_2$CO) δ 16.4, 42.3, 48.3, 51.5, 52.1, 53.8, 59.6, 68.8, 72.4, 74.7, 128.3, 128.7, 129.2, 139.9; HRMS (ESI)$^+$: m/z calcd for [M+H]$^+$: 295.1572, found 295.1572; [α]$^{20}_D$=−13.3 (c=0.12, MeOH).

Example 54

(S)-1-(Chloromethyl)-3-((R)-1-(naphthalen-1-yloxy)ethyl)-1,4-diaza-bicyclo[2.2.2]octane chloride 58

(S)-2-((R)-1-(Naphthalen-1-yloxy)ethyl)-1,4-diaza-bicyclo[2.2.2]octane (18 mg, 0.057 mmol) was dissolved in dry dichloromethane (20 ml) and left at room temperature under argon, without stirring, for 4 days. Removal of the solvent under reduced pressure afforded (S)-1-(chloromethyl)-3-((R)-1-(naphthalen-1-yloxy)ethyl)-1,4-diaza-bicyclo[2.2.2]octane chloride (19 mg, 93%) as a white solid.

$^1$H NMR (250 MHz, acetonitrile-d$_3$) δ 1.40 (d, J=3.96 Hz, 3 H), 2.97-3.21 (m, 2 H), 3.29 (d, J=6.70 Hz, 2 H), 3.34-3.62 (m, 6 H), 3.75 (d, J=8.83 Hz, 2 H), 4.75-4.94 (m, 1 H), 5.07-5.29 (m, 2 H), 7.02 (d, J=6.40 Hz, 1 H), 7.33-7.58 (m, 4 H), 7.85 (br. s., 1 H), 8.13 (br. s., 1 H).

Example 55

(S)-2-((R)-1-(Benzyloxy)ethyl)-1-(chloromethyl)-1,4-diaza-bicyclo[2.2.2]octane tetrafluoroborate 59

(S)-2-((R)-1-(Benzyloxy)ethyl)-1-(chloromethyl)-1,4-diaza-bicyclo[2.2.2]octane chloride (711 mg, 2.15 mmol) was suspended in dry acetonitrile (15 ml) under argon. Sodium tetrafluoroborate (236 mg, 2.15 mmol) was added and the reaction was stirred at room temperature for 24 hours. The precipitate was filtered off and washed with acetonitrile and the filtrate was evaporated under reduced pressure to afford (S)-2-((R)-1-(benzyloxy)ethyl)-1-(chloromethyl)-1,4-diaza-bicyclo[2.2.2]octane tetrafluoroborate as a white solid (623 mg, 76%).

$^1$H NMR (250 MHz, (CD$_3$)$_2$CO) δ 1.31 (d, J=6.09 Hz, 3H), 3.10-3.25 (m, 1H), 3.28-3.47 (m, 3H), 3.48-3.89 (m, 8H), 4.56 (d, J=11.57 Hz, 1H), 4.72 (d, J=11.57 Hz, 1H), 5.21-5.51 (m, 2H), 7.11-7.57 (m, 5H); $^{13}$C NMR (63 MHz, (CD$_3$)$_2$CO) δ 16.4, 42.3, 48.2, 51.9, 52.7, 54.2, 59.4, 69.1, 72.3, 74.6, 128.4, 128.6, 129.2, 139.7; HRMS (ESI)$^+$: m/z calcd for 295.1577, found 295.1575; [α]$^{20}_D$=−6.4 (c=0.09, MeOH).

Example 56

(S)-2-((R)-1-(Benzyloxy)ethyl)-1-(chloromethyl)-1,4-diaza-bicyclo[2.2.2]octane trifluoromethanesulfonate 60

(S)-2-((R)-1-(Benzyloxy)ethyl)-1-(chloromethyl)-1,4-diaza-bicyclo[2.2.2]octane chloride (39 mg, 0.117 mmol, 1 eq) and sodium trifluoromethanesulfonate (20 mg, 0.117 mmol, 1 eq) were stirred in dry acetonitrile (1 ml) at room temperature overnight. The precipitate was filtered off and washed with acetonitrile and the filtrate was evaporated to dryness to yield (S)-2-((R)-1-(benzyloxy)ethyl)-1-(chloromethyl)-1,4-diaza-bicyclo[2.2.2]octane trifluoromethanesulfonate (45 mg, 86%) as a white solid.

$^1$H NMR (250 MHz, CD$_3$CN) δ 1.24 (d, J=6.40 Hz, 3H), 2.89-3.07 (m, 1H), 3.08-3.56 (m, 9H), 3.64 (quin, J=5.86 Hz, 1H), 4.46 (d, J=11.57 Hz, 1H), 4.66 (d, J=11.57 Hz, 1H), 4.86-5.05 (m, 2H), 7.23-7.46 (m, 5H); $^{13}$C NMR (63 MHz, CD$_3$CN) δ 16.3, 42.2, 47.9, 52.0, 52.9, 54.3, 59.2, 69.4, 72.3, 74.5, 128.7, 128.8, 129.5, 139.7.

Example 57

(S)-2-((R)-1-(Benzyloxy)ethyl)-4-(chloromethyl)-4-fluoro-1,4-diaza-bicyclo[2.2.2]octane trifluoromethanesulfonate 61

(S)-2-((R)-1-(benzyloxy)ethyl)-1-(chloromethyl)-1,4-diaza-bicyclo[2.2.2]octane trifluoromethane sulfonate (37 mg, 0.083 mmol) was dissolved in deuterated acetonitrile (3.5 ml) and N-fluoropentachloropyridinium triflate (35 mg, 0.083 mmol) was added. After stirring at room temperature for 1 hour, all fluorinating reagent was consumed ($^{19}$F-NMR) but starting material was left ($^1$H-NMR). More N-fluoropentachloropyridinium triflate (10 mg, 0.024 mmol, 0.3 eq) was added and stirring continued for 30 min. The solvent was evaporated and the crude product was stirred in diethyl ether/DCM (9/1) at room temperature for 3 h. The suspension was filtered and the residue washed with diethyl ether/DCM (9/1) and dried under reduced pressure to give (S)-2-((R)-1-(benzyloxy)ethyl)-4-(chloromethyl)-4-fluoro-1,4-diaza-bicyclo[2.2.2]octane trifluoromethanesulfonate (34 mg, 88%) as a white solid. $^{19}$F-NMR spectra showed the product to have 42% purity the next day ($^{19}$F-NMR) slowly decomposing over days as a solid in the fridge.

$^{19}$F NMR (470 MHz, acetonitrile-d$_3$) δ−79.34, 33.19

Example 58

(S)-Methyl 2-(bis(tert-butoxycarbonyl)amino)-3-phenylpropanoate 62

To a suspension of L-phenylalanine methyl ester (20 g, 93.02 mmol) in THF:water (2:1, 333:166 mL), Na$_2$CO$_3$ (59 g, 558.14 mmol) was added portion wise. At 0° C. (Boc)$_2$O (40 g, 186.04 mmol) was added in one portion and the reaction mixture was stirred at room temperature for 2 h. The organic layer was extracted with ethyl acetate and washed with saturated NH$_4$Cl solution, water and brine. Then the organic layer was dried and concentrated. A solution of the concentrate and DMAP (5.6 g, 46.51 mmol) in acetonitrile was treated with (Boc)$_2$O (40 g, 186.04 mmol) and stirred at room temperature overnight. Then the reaction was concentrated. The concentrate was diluted with ethyl acetate and washed with saturated NH$_4$Cl solution, water and brine. The organic layer was dried and concentrated. The crude product was purified by flash column chromatography (Hexane:ethyl acetate, 90:10) to afford (S)-methyl 2-(bis(tert-butoxycarbonyl)amino)-3-phenylpropanoate (32.5 g, 92% yield).

Example 59

Methyl (4S,5R)-3-N-tert-butoxycarbonyl-5-phenyl-1,3-oxazolidin-2-oxo-4-carboxylate 63

A mixture (S)-methyl 2-(bis(tert-butoxycarbonyl)amino)-3-phenylpropanoate (3.24 g, 8.55 mmol) and N-bromosuccinimide (1.5 g, 8.55 mmol) in carbon tetrachloride (170 mL) was heated at reflux for 1 h under nitrogen while being irradiated with two 150 w bulbs. The mixture then was cooled to room temperature, filtered and concentrated. To a solution of the concentrate in dry acetone (80 mL), silver nitrate (2.18 g, 12.82 mmol) was added. The reaction mixture was stirred at room temperature in the dark for 2 h. Then it was filtered through a Celite pad, and concentrated. The residue was diluted with ethyl acetate and washed with saturated NH$_4$Cl solution, water and brine. The organic layer was dried and concentrated and the crude product was purified by flash column chromatography (Hexane: ethyl acetate, 90:10) to afford methyl (4S,5R)-3-N-tert-butoxycarbonyl-5-phenyl-1,3-oxazolidin-2-oxo-4-carboxylate (1.32 g, 48% yield).

Example 60

N-tert-Butoxycarbonyl-(2S,3R)-β-hydroxyphenylalanine methyl ester 64

A solution of methyl (4S,5R)-3-N-tert-butoxycarbonyl-5-phenyl-1,3-oxazolidin-2-oxo-4-carboxylate (327 mg, 1.02 mmol) in methanol (10 mL) was treated with Cs$_2$CO$_3$ (66 mg, 0.204 mmol) and stirred at room temperature for 2 h. Then the reaction mixture was concentrated, and the residue was diluted with ethyl acetate and washed with saturated NH$_4$Cl solution, water and brine. The organic layer was dried and concentrated. The crude product was purified by flash column chromatography (Hexane: ethyl acetate, 80:20) to afford N-tert-butoxycarbonyl-(2S,3R)-β-hydroxphenylalanine methyl ester (196 mg, 65% yield) and methyl 2-(ted-butoxycarbonylamino)-3-phenylacrylate (42.7 mg, 15% yield).

Example 61

(2S,3S)-Methyl-2-(tert-butoxycarbonylamino)-3-(4-methoxybenzyloxy)-3-phenylpropanoate 64

A solution of N-tert-butoxycarbonyl-(2S,3R)-β-hydroxyphenylalanine methyl ester (563 mg, 1.91 mmol) and 4-methoxybenzyl 2,2,2-trichloroacetimidate (801 mg, 2.86 mmol) in toluene (40 mL) was treated with lanthanum triflate (56 mg, 0.095 mmol) and the mixture was stirred for at room temperature for 30 minutes. Saturated aqueous NaHCO$_3$ solution was added and the mixture was extracted with diethyl ether. The organic layer was dried, filtered and concentrated to give a residue which was purified by column silica gel column chromatography (hexane:diethyl ether, 85:15) affording (2S,3S)-methyl 2-(tert-butoxycarbonylamino)-3-(4-methoxybenzyloxy)-3-phenylpropanoate (719 mg, 91% yield).

$^1$H NMR (400 MHz, CDCl$_3$) δ 1.32 (s, 9H), 3.65 (s, 3H), 3.77 (s, 3H), 4.17 (d, J=11.4 Hz, 1H), 4.50 (d, J=11.6 Hz, 2H), 4.94 (d, J=2.8 Hz, 1H), 5.42 (d, J=9.6 Hz, 1H), 6.87 (d, J=8.6 Hz, 2H), 7.14 (d, J=8.6 Hz, 2H), 7.37 (d, J=4.0 Hz, 5H); $^{13}$C NMR (101 MHz, CDCl$_3$) δ 27.9, 51.9, 54.9, 59.1, 70.2, 79.2, 79.3, 113.5, 126.7, 126.7, 127.8, 128.2, 128.2, 129.2, 129.3, 129.3, 137.1, 155.1, 159.1, 170.6; HRMS (ESI)$^+$: m/z calcd for C$_{23}$H$_{29}$NNaO$_6$ [M+Na]$^+$: 438.1887, found 438.1879; IR (v, cm$^{-1}$): 3448, 1753, 1716, 1513, 1211; [α]$^{22}_D$=−44.5 (c=1.41, MeOH).

Example 62 tert-butyl (2S,3S)-1-(aminooxy)-3-(4-methoxybenzyloxy)-1-oxo-3-phenylpropan-2-ylcarbamate 65

A solution of (2S,3S)-methyl 2-(tert-butoxycarbonylamino)-3-(4-methoxybenzyloxy)-3-phenylpropanoate (800 mg, 1.86 mmol) in methanol (saturated with NH$_3$ gas for 1 h at −5° C.) was stirred in a sealed tube at room temperature for 4 days. Then the solvent was evaporated under reduced pressure affording tert-butyl (2S,3S)-1-(aminooxy)-3-(4-methoxybenzyloxy)-1-oxo-3-phenylpropan-2-ylcarbamate (756 mg, 98% conversion).

$^1$H NMR (400 MHz, CDCl$_3$) δ 1.34 (s, 9H), 3.76 (s, 3H), 4.33 (d, J=10.9 Hz, 1H), 4.45 (d, J=10.6 Hz, 2H), 5.08 (d, J=2.6 Hz, 1H), 5.51 (d, J=8.6 Hz, 1H), 6.59 (d, J=13.1 Hz, 2H), 6.85 (d, J=8.3 Hz, 3H), 7.21 (d, J=8.1 Hz, 3H), 7.29-7.35 (m, 3H); $^{13}$C NMR (101 MHz, CDCl$_3$) δ 27.9, 54.9, 59.3, 71.1, 79.4, 79.8, 113.6, 126.7, 126.7, 127.8, 128.2, 128.2, 129.3, 129.3, 129.4, 137.4, 155.3, 159.1, 163.9, 172.4; HRMS (ESI)$^+$: m/z calcd for C$_{22}$H$_{28}$N$_2$NaO$_5$ [M+Na]$^+$: 423.1890, found 423.1881; IR (v, cm$^{-1}$): 3352, 1661, 1613; [α]$^{22}_D$=−16.7 (c=0.77, MeOH).

Example 63

N,N'-((2R,3S)-3-((4-methoxybenzyl)oxy)-3-phenylpropane-1,2-diyl)bis(2-chloroacetamide) 66

To a solution of tert-butyl (2S,3S)-1-(aminooxy)-3-(4-methoxybenzyloxy)-1-oxo-3-phenylpropan-2-ylcarbamate (500 mg, 1.20 mmol) in dry methanol (30 mL) was added HCl in methanol (3M, 1 mL) and stirred at room temperature for 33 hours. The solvent was evaporated, saturated NaHCO$_3$ solution was added and the aqueous layer was extracted with ethyl acetate. The combined organic extracts were dried, filtered and evaporated affording 402 mg of the unprotected amine that was used in the next step without further purification.

The previous residue (402 mg, 1.33 mmol) was dissolved in THF (10 mL) and cooled to 0° C. Then a BH$_3$.THF (1 M in THF, 4 mL, 4 mmol) was added dropwise and the solution was stirred at reflux for 23 hours. The solution was cooled to 0° C., methanol was added dropwise and the reaction was stirred overnight. The solvent was evaporated; a mixture of chloroform, water and a bit of HCl 1M solution was added and the suspension was shaken well for 1 minute. Then it was neutralized by the addition of saturated NaHCO$_3$ solution and extracted with chloroform. The combined organic extracts were dried, filtered and evaporated to afford a crude (255 mg) that was used for the next step without further purification.

The crude mixture (255 mg) was dissolved in dichloromethane (8 mL) and 4-dimethylaminopyridine (3.7 mg, 0.03 mmol), triethylamine (0.62 mL, 4.45 mmol) and chloroacetyl chloride (0.21 mL, 2.67 mmol) were added sequentially at 0° C. and the solution was stirred at room temperature overnight. Water and HCl 1M were added, stirred for 5 minutes and then extracted with dichloromethane. The combined organic extracts were dried, filtered and evaporated and the residue was purified by silica gel flash column chromatography (Hexane:ethyl acetate, from 1:1 to 3:7) affording 79 mg (16% yield after 3 steps) N,N'-((2R,3S)-3-((4-methoxybenzyl)o*-3-phenylpropane-1,2-diyl)bis(2-chloroacetamide).

$^1$H NMR (400 MHz, CDCl$_3$) δ 1.34 (s, 9H), 3.76 (s, 3H), 4.33 (d, J=10.9 Hz, 1H), 4.45 (d, J=10.6 Hz, 2H), 5.08 (d, J=2.6 Hz, 1H), 5.51 (d, J=8.6 Hz, 1H), 6.59 (d, J=13.1 Hz, 2H), 6.85 (d, J=8.3 Hz, 3H), 7.21 (d, J=8.1 Hz, 3H), 7.29-7.35 (m, 3H); $^{13}$C NMR (101 MHz, CDCl$_3$) δ 27.9, 54.9, 59.3, 71.1, 79.4, 79.8, 113.6, 126.7, 126.7, 127.8, 128.2, 128.2, 129.3, 129.3, 129.4, 137.4, 155.3, 159.1, 163.9, 172.4; HRMS (ESI)$^+$: m/z calcd for C$_{22}$H$_{28}$N$_2$NaO$_5$ [M+Na]$^+$: 423.1890, found 423.1881; IR (v, cm$^{-1}$): 3352, 1661, 1613; [α]$^{22}_D$=−16.7 (c=0.77, MeOH).

Example 64

(1R,3R,4R)-1-(Chloromethyl)-3-((S)-hydroxy(phenyl)methyl)-1,4-diazabicyclo[2.2.2]octan-1-ium chloride 67

To a solution of N,N'-((2R,3S)-3-((4-methoxybenzyl)oxy)-3-phenylpropane-1,2-diyl)bis(2-chloroacetamide) (347 mg, 0.79 mmol) in THF (10 mL) at 0° C. was added dropwise BH$_3$.THF (1M in THF, 3.2 mL, 3.17 mmol) and the reaction was heated at reflux overnight. The reaction mixture was cooled to room temperature and MeOH was added dropwise to consume the remaining BH$_3$.THF and stirred for 12 hours at room temperature. Then the solvent was evaporated, water, chloroform and some 1M HCl was added and the mixture was stirred for one minute. A saturated aqueous NaHCO$_3$ solution was used to neutralize the excess of acid and then extracted with chloroform. The combined organic extracts were dried, filtered and evaporated to give 223 mg of a crude which was used in the next step with no further purification.

The crude product (246 mg) was dissolved in dimethylformamide (7 mL) and heated at 110° C. overnight. Then, 3 mL of a saturated aqueous NaHCO$_3$ solution was added and the solvent was evaporated. Water was added and the suspension was extracted several times with dichloromethane. The combined organic extracts were dried, filtered and evaporated affording 125 mg of a crude that was used directly in the next step.

The crude product from the previous step was dissolved in dichloromethane (2 mL) and dry acetone (1 mL) and was stirred at room temperature for 6 days while monitoring by mass spectrometry. The liquid part was separated from the remaining solid stuck at the bottom of the flask and rinsed with dichloromethane twice. The solid was dried under vacuo affording 32 mg (13% yield in 3 steps) of (1R,3R,4R)-1-(chloromethyl)-3-((S)-hydroxy(phenyl)methyl)-1,4-diazabicyclo[2.2.2]octan-1-iu chloride.

$^1$H NMR (400 MHz, CD$_3$OD) δ 3.08-3.19 (m, 3H), 3.27 (ddd, J=4.8, 4.8, 3.3 Hz, 2H), 3.37-3.50 (m, 5H), 3.55-3.63 (m, 1H), 4.71 (d, J=9.1 Hz, 1H, CH), 5.09 (d, J=9.8 Hz, 1H, CH$_2$Cl), 5.13 (d, J=9.8 Hz, 1H, CH$_2$Cl), 7.31-7.38 (m, 3H), 7.46 (d, J=6.8 Hz, 2H); $^{13}$C NMR (100.6 MHz, CD$_3$OD) δ 41.0, 48.0, 52.2, 53.0, 54.9, 60.9, 69.2, 73.3, 128.7, 128.7, 129.8, 129.9, 129.9, 141.1; IR (v, cm$^{-1}$) 3361, 2934, 1514, 1455, 1249; HRMS required for C$_{14}$H$_{20}$ClN$_2$O ([M]$^+$): 267.1259, found 267.1259; [α]$^{22}_D$=−17.2 (c=1.01, MeOH).

The structure of compound 67 is depicted in paragraph [0060] above.

Example 65

(S)-2-((R)-1-(Benzyloxy)ethyl)-1-(chloromethyl)-1,4-diaza-bicyclo[2.2.2]octane tetrafluoroborate 59

A crystal structure was determined using the general procedure described in example 43:

| | |
|---|---|
| Empirical formula | C$_{16}$ H$_{24}$ B$_1$ Cl$_1$ F$_4$ N$_2$ O$_1$ |
| Moiety formula | C$_{16}$ H$_{24}$ Cl N$_2$ O, B F$_4$ |
| Formula weight | 382.63 |
| Temperature | 150 K |
| Wavelength | 0.71073 Å |
| Crystal system | Monoclinic |
| Space group | P1 21 1 |
| Unit cell dimensions | a = 9.4079(2) Å |
| | b = 9.2725(2) Å |
| | c = 10.5160(2) Å |
| | α = 90° |
| | β = 101.557(2)° |
| | γ = 90° |
| Volume | 898.76(3) Å$^3$ |

Example 66

(2S,3S)-2,3-Bis(4-(trifluoromethyl)phenyl)-1-methyl-4-aza-azoniabicyclo[2.2.2]octane trifluoromethanesulfonate 68

To a solution of (2S,3S)-2,3-bis(4-(trifluoromethyl)phenyl)-1,4-diazabicyclo[2.2.2]octane 5 (1.0 eq) in Et$_2$O (0.02 M) at 0° C. was added dropwise methyl trifluoromethanesulfonate (1.0 eq). The reaction was stirred for 3 hours, after which the precipitate was collected under vacuum filtration. The resulting solid was washed with ether and acetone to afford (2S,3S)-2,3-bis(4-(trifluoromethyl)phenyl)-1-methyl-4-aza-azoniabicyclo[2.2.2]octane trifluoromethanesulfonate as a white solid (143 mg, 92 yield). $^1$H NMR (400 MHz, CD3CN): δ=2.71 (s, 3H), 3.04-3.13 (m, 1H), 3.15-3.24 (m, 1H), 3.25-3.32 (m, 1H), 3.45-3.63 (m, 3H), 3.68 (ddt, J=12.4 Hz, J=9.5 Hz, J=3.2 Hz, 1H), 3.85 (ddt, J=12.4 Hz, J=10.5 Hz, J=2.9 Hz, 1H), 4.93 (d, J=9.6 Hz, 1H), 5.00 (d, J=9.6 Hz, 1H), 7.55 (d, J=8.4 Hz, 2H), 7.65 (d, J=8.4 Hz, 2H), 7.92 (d, J=8.3 Hz, 2H), 8.10 (d, J=8.3 Hz, 2H); $^{13}$C NMR (100.6 MHz, CD3CN): δ=40.8, 46.9, 50.0, 50.7, 58.4, 62.9, 71.2, 121.6 (q, J=320.5 Hz, OTf), 124.7 (q, J=270.2 Hz, CF3), 125.0 (q, J=271.1 Hz, CF3), 126.4 (q, J=3.9 Hz), 127.7 (q, J=3.7 Hz), 128.8, 128.8, 130.5 (q, J=32.1 Hz), 133.4 (q, J=33.3 Hz), 135.4, 142.1; $^{19}$F {1H} NMR (376 MHz, CD3CN): δ=−62.5 (CF3), −79.3 (TfO); IR (v, cm$^{-1}$): 3095, 2955; Elemental analysis: Calc. for C22H21F9N2O3S: C, 46.81; H, 3.75; N, 4.96. Found: C, 46.74; H, 3.70; N, 4.61; [α]$^{22}_D$+43.0 (c 0.30, MeOH); mp: 182-83° C.

Example 67

(2S,3S)-2,3-Bis(4-(trifluoromethyl)-phenyl)-1-fluoro-4-methyl-1,4-diazoniabicyclo[2.2.2]octane bis (trifluoromethanesulfonate) 69

A solution of (2S,3S)-2,3-bis(4-(trifluoromethyl)phenyl)-1-methyl-4-aza-azoniabicyclo[2.2.2]octane trifluoromethanesulfonate 68 (1.0 eq) and sodium trifluoromethanesulfonate (1.0 eq) in acetonitrile (0.02 M) was prepared in a small PTFE reactor. The mixture was purged with $N_2$ and cooled to −35° C. Elemental $F_2$ as a homogeneous 1:9 (v/v) mixture with N2 was introduced at a flow rate of 15 mL/min into the rapidly stirred mixture via PTFE tubing at −35° C. The reaction was monitored by $^{19}$F NMR. Once fluorination was complete, the mixture was allowed to warm to room temperature, before filtration to remove sodium fluoride, and the solution was evaporated under reduced pressure. Purification by recrystallization (Et20/MeOH 4:1) afforded (2S,3S)-2,3-bis(4-(trifluoromethyl)-phenyl)-1-fluoro-4-methyl-1,4-diazoniabicyclo[2.2.2]octane bis (trifluoromethanesulfonate) as a pale yellow solid (115 mg, 97% yield). $^1$H NMR (400 MHz, CD$_3$CN): δ=3.03 (s, 3H), 4.30-4.36 (m, 1H), 4.51 (d, J=21.8 Hz, 1H), 4.61 (dd, J=19.8 Hz, J=10.3 Hz, 1H), 4.76-4.86 (m, 3H), 5.09 (q, J=10.0 Hz, 1H), 5.41 (q, J=11.4 Hz, 1H), 6.22 (d, J=10.5 Hz, 1H), 6.71 (d, J=10.7 Hz, 1H) 7.90 (m, 4H), 8.09-8.20 (m, 4H); $^{13}$C NMR (100.6 MHz, CD$_3$CN): δ=51.2, 53.9, 53.9 (d, J=6.6 Hz), 59.2 (d, J=5.2 Hz), 60.2 (d, J=15.3 Hz), 73.2, 76.3 (d, J=14.2 Hz), 121.8 (q, J=320.3 Hz, OTD, 124.2 (q, J=272.4 Hz), 124.3 (q, J=272.1 Hz), 126.3, 128.1 (q, J=3.6 Hz), 128.4 (q, J=3.5 Hz), 129.0, 133.9, 133.9, 135.2 (q, J=28.7 Hz), 135.4 (q, J=29.0 Hz); $^{19}$F {1H} NMR (376 MHz, CD3CN): δ=+36.6 ([N+F]+), −63.9 (CF3), −64.0 (CF3), −79.3 (TfO); IR (v, cm$^{-1}$): 3095, 2955; Elemental analysis: Calc. for C$_{23}$H$_{21}$F$_{13}$N$_2$O$_6$S$_2$: C, 37.71; H, 2.89; N, 3.82. Found: C, 37.43; H, 2.76; N, 3.90; [q]$^{22}$D+74.5 (C, 0.53; MeOH); mp: 147-150° C.

The structure of compound 67 is depicted in paragraph [0060] above.

Example 68

(1S,2S)-1,2-Di-O-tolylethane-1,2-diamine dihydrochloride 70

To a solution of (1R,2R)-1,2-bis(2-hydroxylphenyl)-1,2-diaminoethane (1.00 g, 4.09 mmol) in DMSO (80 mL) was added o-tolualdehyde (1.14 mL, 9.81 mmol). The resulting mixture was stirred overnight at room temperature before being poured onto water (150 mL). The aqueous layer was extracted with ether and the combined organic phases were washed with water, dried over MgSO$_4$ and evaporated under reduced pressure. To the resultant diimine intermediate in THF (100 mL) was added 37% HCl (3.0 mL) and the reaction was stirred for 3 hours before concentrating in vacuo. The resultant solid was dissolved in water (25 mL) and washed with ether. The aqueous layer was then made basic with 3M NaOH and extracted with EtOAc. The organic layer was further washed with 1M NaOH and then extracted with 1M HCl. The aqueous layer was evaporated under reduced pressure to afford (1S,2S)-1,2-di-O-tolylethane-1,2-diamine dihydrochloride as a pale yellow solid (609 mg, 48% yield). $^1$H NMR (400 MHz, DMSO-d$_6$): δ=2.17 (s, 6H), 5.33 (s, 2H), 7.01 (d, J=7.3 Hz, 2H), 7.12 (td, J=7.5 Hz, 2H), 7.18 (t, J=7.2 Hz, 2H), 7.75 (d, J=7.5 Hz, 2H), 9.22 (s, 6H); $^{13}$C NMR (100.6 MHz, DMSO-d$_6$): δ=19.6, 53.2, 126.7, 127.6, 129.4, 130.9, 133.3, 136.8; IR (v, cm$^{-1}$): 3430; HRMS (ESI$^+$, m/z): [C$_{16}$H$_{21}$N$_2$]+(M+H)+calc. 241.1699, found 241.1709.

Example 69

N,N'-((1S,2S)-1,2-di-O-tolylethane-1,2-diyl)bis(2-chloroacetamide) 71

To a suspension of (1S,2S)-1,2-di-O-tolylethane-1,2-diamine dihydrochloride 70 (600 mg, 1.92 mmol) in DCM (50 mL) at 0° C. was added Et$_3$N (2.14 mL, 15.4 mmol) followed by DMAP (10 mg) and chloroacetyl chloride (617 μL, 7.68 mmol). The reaction was stirred overnight before quenching with water (50 mL) and extracting into DCM (3×100 mL). The combined organic layers were washed with brine, dried over MgSO$_4$ and evaporated under reduced pressure. Purification by column chromatography (SiO2, EtOAc/PE 2:3) afforded N,N'-((1S,2S)-1,2-di-O-tolyle-thane-1,2-diyl)bis(2-chloroacetamide) as a white solid (509 mg, 67% yield). $^1$H NMR (500 MHz, CDCl$_3$): δ=1.98 (s, 6H), 4.03 (d, J=15.1 Hz, 2H), 4.09 (d, J=15.1 Hz, 2H), 5.64-5.71 (m, 2H), 6.97 (d, J=7.5 Hz, 2H), 7.13 (td, J=7.5 Hz, J=1.1 Hz, 2H), 7.23 (t, J=7.4 Hz, 2H), 7.39 (brs, 2H, NH), 7.50 (d, J=7.7 Hz, 2H); $^{13}$C NMR (125.8 MHz, CDCl$_3$): δ=19.2, 42.5, 54.9, 126.5, 126.6, 128.1, 130.7, 136.3, 136.4, 166.7; IR (v, cm$^{-1}$): 3261, 1651, 1537, 1243; HRMS (ESI$^+$): m/z calc. for C$_{20}$H$_{22}$Cl$_2$N$_2$NaO$_2$ ([M+Na]+): 415.0951, found 415.0958; [α]$^{22}$D+90 (c 0.20, MeOH); mp: 174-176° C.

Example 70

(2S,3S)-2,3-Di-O-tolyl-1,4-diazabicyclo[2.2.2]octane 72

To a solution of N,N'-((1S,2S)-1,2-di-O-tolylethane-1,2-diyl)bis(2-chloroacetamide) 71 (500 mg, 1.28 mmol) in THF (15 mL) at 0° C. was added dropwise BH3.THF (1M in THF, 5.1 mL, 5.10 mmol) and the reaction was heated at reflux for 12 hours. The reaction mixture was cooled to room temperature and MeOH was added dropwise and stirred for 5 hours at room temperature. Then the solvent was concentrated, HCl (1M) was added and the mixture was stirred at the same temperature for 12 hours. NaOH (3M) was added to bring the reaction mixture to pH 14 and was extracted with dichloromethane. The combined organic extracts were dried over MgSO$_4$ and evaporated under reduced pressure to furnish the crude diamine, which was used in the next step with no further purification. The crude product (343 mg) was dissolved in DMF (12 mL) and heated at 150° C. for 12 hours. The solvent was concentrated under reduced pressure and the residue was dissolved in water. The aqueous phase was treated with 3M NaOH to reach pH 14 and extracted with DCM. The combined organic extracts were dried over MgSO$_4$ and evaporated under reduced pressure. Purification by column chromatography (SiO$_2$, CHCl$_3$/MeOH 99:1) afforded (2S,3S)-2,3-di-O-tolyl-1,4-diazabicyclo[2.2.2]octane as an oil (147 mg, 40% yield over 2 steps). $^1$H NMR (400 MHz, CDCl$_3$): δ=2.55-2.65 (m, 2H), 2.64 (s, 6H), 2.85-3.01 (m, 4H), 3.21-3.31 (m, 2H), 4.65 (s, 2H), 7.17-7.25 (m, 4H), 7.26-7.31 (m, 2H), 7.38-7.43 (m, 2H); $^{13}$C NMR (100.6 MHz, CDCl$_3$): δ=19.9, 40.5, 49.6, 55.9, 124.9, 125.3, 127.2, 131.3, 136.9, 139.0; IR (v, cm$^{-1}$): 2937, 1458, 1075; HRMS (ESI$^+$): m/z calc. for C$_{20}$H$_{25}$N$_2$ ([M+H]$^+$): 293.2012, found 293.2004; [α]$^{22}$D u+111 (c 0.15, MeOH).

Example 71

(2S,3S)-2,3-Di-O-tolyl-1-methyl-4-aza-azoniabicyclo[2.2.2]octane trifluoromethanesulfonate 73

To a solution of (2S,3S)-2,3-di-O-tolyl-1,4-diazabicyclo[2.2.2]octane 72 (147 mg, 0.50 mmol) in DCM (20 mL) at −78° C., methyl trifluoromethanesulfonate (40 μL, 0.45 mmol) in DCM (5 mL) was added dropwise (10 min addition time) at the same temperature and the reaction mixture was stirred for 4 hours at −78° C. The solvent was evaporated under reduced pressure before ether was added and the resulting solid was recovered by filtration and dried under high vacuum to afford (2S,3S)-2,3-di-O-tolyl-1-methyl-4-aza-azoniabicyclo[2.2.2]octane trifluoromethanesulfonate as a white solid (197 mg, 86% yield). $^1$H NMR (400 MHz, CD$_3$CN): δ=2.39 (s, 3H), 2.57 (s, 3H), 2.64 (s, 3H), 3.01 (ddd, J=9.5 Hz, 6.6 Hz, 2.2 Hz, 1H), 3.15-3.25 (m, 2H), 3.36 (ddd, J=10.3 Hz, 7.1 Hz, 6.8 Hz, 1H), 3.49-3.59 (m, 1H), 3.68-3.76 (m, 1H), 3.78-3.85 (m, 1H), 3.92 (ddt, J=9.5 Hz, 3.2 Hz, 3.0 Hz, 1H), 4.78 (d, J=10.1 Hz, 1H), 5.16 (d, J=10.1 Hz, 1H), 7.19-7.30 (m, 4H), 7.35-7.41 (m, 2H), 7.57 (d, J=7.4 Hz, 1H), 7.92-7.95 (m, 1H); $^{13}$C NMR (100.6 MHz, CD$_3$CN): δ=19.8, 21.0, 40.5, 47.6, 48.8, 50.9, 59.5, 62.8, 65.9, 121.7 (q, J=321.1 Hz, CF$_3$), 126.3, 126.9, 128.6, 129.1, 129.5, 129.8, 132.0, 132.6, 133.3, 134.1, 140.4, 141.2; $^{19}$F {1H} NMR (376.5 MHz, CD$_3$CN): δ=−79.3 (TfO); IR (v, cm$^{-1}$): 1465, 1257, 1029; HRMS (ESI+): m/z calc. for C$_{21}$H$_{27}$N$_2$ ([M]$^+$): 307.2169, found 307.2154; [α]$^{22}_D$+38 (c 0.175, MeOH); mp: 89-91° C.

Example 72

N-Fluoropentachloropyridinium Triflate 74

N-fluoropentachloropyridinium triflate can be purchased from commercial sources or prepared according to the following procedure.

Pentachloropyridine (10.0 g, 39.8 mmol) and triflic acid (5.00 mL, 56.9 mmol) were mixed in trifluoroacetic acid (160 mL). The mixture was purge with nitrogen for 20 min and cooled using an ice bath before 10% F2/N2 (3.0 eq) was passed through the mixture at a rate of 30 mL/min at 5° C. for 15 hours. After the reaction, the mixture was purged with nitrogen for 30 min, and the solvent was evaporated under reduced pressure. Ether (50 mL) was slowly added to the oily residue and the resulting white precipitate formed was collected by filtration and washed with EtOAc (15 mL) to afford the title compound as a white solid. $^{13}$C NMR (125.8 MHz, CD$_3$CN): δ=135.4, 142.0, 156.0; $^{19}$F {1H} NMR (376 MHz, CD$_3$CN): δ=+46.5 ([N−F]$^+$), −79.3 (OTf); mp: 123-124° C.; Elemental analysis: C$_6$Cl$_5$F$_4$NO$_3$S: C, 17.18; N, 3.34. Found: C, 17.07; N, 3.41. Data consistent with literature values. (Urnernoto T., Harasawa K., Tornizawa G., Kawada K., Tomita K, *Bull. Chem. Soc. Japan,* 1991, 64, 1081-1092; Umemoto T., Harasawa K., Tomizawa G., Kawada K., Tomita K. *J. Fluorine Chem.,* 1991, 53, 369-378)

General Procedure for the Formation of N–F Reagents Using N–F Pentachloropyridinium Triflate To a solution of N–F pentachloropyridinium triflate (1 eq) in acetonitrile (0.02 M) was added chiral substituted-4-aza-1-azoniabicylo[2.2.2]octane salt (1 eq) at room temperature. The reaction was monitored by $^{19}$F NMR. After completion, the solution was concentrated under reduced pressure. Purification by trituration with dichloromethane followed by recrystallisation (Et$_2$O/MeOH 4:1) afforded the desired product.

Example 73

(2S,3S)-2,3-Di-O-tolyl-1-fluoro-4-methyl-1,4-diazoniabicyclo[2.2.2]octane bis (trifluoromethanesulfonate) 75

An in situ sample of the fluorinated reagent was prepared by mixing (2S,3S)-2,3-di-O-tolyl-1-methyl-4-aza-azoniabicyclo[2.2.2]octane trifluoromethanesulfonate 73 (1.0 eq.) with N-fluoropentachloropyridinium triflate 74 (1.0 eq) and NaHCO$_3$ (2.0 eq) in CD$_3$CN. Filtration through a cotton wool pipette afforded the in situ prepared (2S,3S)-2,3-di-O-tolyl-1-fluoro-4-methyl-1,4-diazoniabicyclo[2.2.2]octane bis(triflate) which displayed the following characteristic data. $^{19}$F {1H} NMR (376 MHz, CD$_3$CN): δ=+33.6 ([N−F]$^+$), −79.3 (OTf).

The structure of compound 75 is depicted in paragraph [0060] above.

Example 74

(1S,2S)-1,2-Di([1,1'-biphenyl]-2-yl)ethane-1,2-diamine dihydrochloride 76

To a solution of (1R,2R)-1,2-bis(2-hydroxylphenyl)-1,2-diaminoethane (1.00 g, 4.09 mmol) in DMSO (80 mL) was added 2-phenyl-benzaldehyde (1.79 g, 9.81 mmol). The resulting mixture was stirred overnight at room temperature before being poured onto water (150 mL). The aqueous layer was extracted with ether and the combined organic phases were washed with water, dried over MgSO$_4$ and evaporated under reduced pressure. To the resultant diimine intermediate in THF (100 mL) was added 37% HCl (3.0 mL) and the reaction was stirred for 3 hours before concentrating in vacuo. The resultant solid was dissolved in water (25 mL) and washed with ether. The aqueous layer was then made basic with 3M NaOH and extracted with EtOAc. The organic layer was further washed with 1M NaOH and then extracted with 1M HCl. The aqueous layer was evaporated under reduced pressure to afford (1S,2S)-1,2-di([1,1'-biphenyl]-2-yl)ethane-1,2-diamine dihydrochloride as a pale yellow solid (590 mg, 33% yield). $^1$H NMR (500 MHz, DMSO-d$_6$): δ=4.92 (s, 2H), 6.95-7.18 (m, 10H), 7.29 (t, J=7.4 Hz, 2H), 7.39-7.49 (m, 6H), 9.31 (brs, 6H); $^{13}$C NMR (125.8 MHz, DMSO-d$_6$): δ=53.5, 127.4, 127.5, 128.0, 128.3, 128.8, 129.4, 129.9, 131.0, 139.0, 141.8; IR (v, cm$^{-1}$): 3374; HRMS (ESI-F, m/z): [C$_{26}$H$_{25}$N$_2$]+(M+H)$^+$calc. 365.2012, found 365.2007; mp: 216-218° C.

Example 75

N,N'-((1S,2S)-1,2-di([1,1'-biphenyl]-2-yl)ethane-1,2-diyl)bis(2-chloroacetamide) 77

To a suspension of (1S,2S)-1,2-di([1,1'-biphenyl]-2-yl) ethane-1,2-diamine dihydrochloride 76 (450 mg, 1.03 mmol) in DCM (20 mL) at 0° C. was added Et$_3$N (1.15 mL, 8.14 mmol) followed by DMAP (10 mg) and chloroacetyl chloride (328 μL, 4.12 mmol). The reaction was stirred overnight before quenching with water (50 mL) and extracting into DCM (3×100 mL). The combined organic layers were washed with brine, dried over MgSO4 and evaporated under reduced pressure. Purification by column chromatography (SiO2, EtOAc/PE 2:3) afforded N,N'-((1S,2S)-1,2-di([1,1'-biphenyl]-2-yl)ethane-1,2-diyl)bis(2-chloroacetamide) as a white solid (330 mg, 62% yield). $^1$H NMR (400 MHz, DMSO-d$_6$): δ=4.01 (d, J=12.8 Hz, 2H), 4.04 (d, J=12.8 Hz, 2H), 5.34-5.42 (m, 2H), 6.76-7.10 (m, 10H), 7.12-7.16 (m, 2H), 7.23-7.35 (m, 6H), 8.74-8.81 (m, 2H, W); $^{13}$C NMR (125.8 MHz, DMSO-d$_6$): δ=42.7, 54.1, 126.4, 126.9, 127.4, 127.5, 127.7, 129.3, 129.3, 136.1, 140.1, 141.1, 165.2; IR (v, cm$^{-1}$): 3295, 1678, 1644, 1530, 1262; HRMS (ESI$^+$): m/z calc. for C$_{30}$H$_{26}$Cl$_2$N$_2$NaO$_2$ ([M+Na]$^+$): 539.1264, found 539.1250; [α]$^{22}_D$ −7.6 (c 0.20, MeOH); mp: 210-212° C.

Example 76

(2S,3S)-2,3-Di([1,1'-biphenyl]-2-yl)-1,4-diazabicyclo[2.2.2]octane 78

To a solution of N,N'-(1S,2S)-1,2-bis([1,1'-biphenyl]-2-yl)ethane-1,2-diyl)bis(2-chloroacetamide) 77 (630 mg, 1.22 mmol) in THF (20 mL) at 0° C. was added dropwise BH3.THF (1 M in THF, 5.0 mL, 4.88 mmol) and the reaction was heated at reflux for 12 hours. The reaction mixture was cooled to room temperature and MeOH was added dropwise and stirred for 5 hours at room temperature. Then the solvent was concentrated, HCl (1 M) was added and the mixture was stirred at the same temperature for 12 hours. NaOH (3M) was added to bring the reaction mixture to pH 14 and the aqueous layer was extracted with DCM. The combined organic extracts were dried over MgSO4 and evaporated under reduced pressure to furnish the crude diamine, which was used in the next step without purification. The crude product (478 mg) was dissolved in dimethylformamide (15 mL) and heated at 150° C. for 12 hours. The solvent was concentrated under reduced pressure and the residue was dissolved in water. The aqueous phase was treated with 3M NaOH to reach pH 14 and extracted with DCM. The combined organic extracts were dried over MgSO$_4$ and evaporated under reduced pressure. Purification by column chromatography (SiO$_2$, CHC13/MeOH 99:1) afforded (2S,3S)-2,3-di([1,1'-biphenyl]-2-yl)-1,4-diazabicyclo[2.2.2]octane as a colourless oil (128 mg, 25% yield over 2 steps). $^1$H NMR (400 MHz, CDCl$_3$): δ=2.36 (ddd, J=9.6 Hz, 7.1 Hz, 3.4 Hz, 2H), 2.55-2.63 (m, 2H), 2.70-2.85 (m, 4H), 4.23 (s, 2H), 6.92 (d, J=7.5 Hz, 2H), 7.03-7.13 (m, 7H), 7.31-7.36 (m, 9H); $^{13}$C NMR (100.6 MHz, CDCl$_3$): δ=40.2, 49.1, 57.3, 125.9, 126.7, 126.9, 126.9, 127.6, 129.7, 130.7, 136.7, 141.8, 144.7; IR (v, cm$^{-1}$): 2938, 1477, 1074; HRMS (ESI$^+$): m/z calc. for C$_{30}$H$_{29}$N$_2$ ([M+H]$^+$): 417.2325, found 417.2321; [α]$^{22}_D$ +98 (c 0.25, MeOH).

Example 77

(2S,3S)-2,3-Di([1,1'-biphenyl]-2-yl)-1-methyl-1,4-diazabicyclo[2.2.2]octan-1-ium trifluoromethanesulfonate 79

To a solution of (2S,3S)-2,3-di([1,1'-biphenyl]-2-yl)-1,4-diazabicyclo[2.2.2]octane 78 (1.0 eq) in DCM (0.02 M) at −78° C., methyl trifluoromethanesulfonate (1.0 eq) in DCM (0.2M) was added dropwise (10 min addition time) at the same temperature and the reaction mixture was stirred for 4 h at −78° C. the solvent was evaporated under reduced pressure before diethyl ether was added and the resulting solid was recovered by filtration and dried under high vacuum to afford (2S,3S)-2,3-di([1,1'-biphenyl]-2-yl)-1-methyl-1,4-diazabicyclo[2.2.2]octan-1-ium trifluoromethanesulfonate as a white solid (139 mg, 78% yield). $^1$H NMR (400 MHz, CD$_3$CN): δ=2.35 (s, 3H), 2.93-3.07 (m, 2H), 3.15-3.47 (m, 6H), 4.68 (d, J=9.5 Hz, 1H), 4.80 (d, J=9.5 Hz, 1H), 7.06-7.66 (m, 18H); $^{13}$C NMR (100.6 MHz, CD$_3$CN): δ=40.2, 47.8, 49.7, 50.1, 59.5, 62.6, 67.8, 121.7 (q, J=321.1 Hz, CF$_3$), 128.0, 128.5, 128.7, 128.8, 128.9, 129.4, 129.4, 129.8, 130.1, 130.3, 130.5, 130.6, 131.8, 132.0, 132.9, 133.2, 140.3, 141.4, 145.7, 147.3; $^{19}$F {1H} NMR (376.5 MHz, CD$_3$CN): δ=−79.3 (TfO); IR (v, cm$^{-1}$): 1257, 1029, 702; HRMS (ESI$^+$): m/z calc. for C$_{31}$H$_{31}$N$_2$ ([M]$^+$): 431.2482, found 431.2475; [α]$^{22}_D$+47 (c 0.26, MeOH); mp: 208-210° C.

Example 78

(2S,3S)-2,3-Di([1,1'-biphenyl]-2-yl)-1-fluoro-4-methyl-1,4-diazabicyclo[2.2.2]octane-1,4-diium bis(trifluoromethanesulfonate) 80

An in situ sample of the fluorinated reagent was prepared by mixing (2S,3S)-2,3-di([1,1'-biphenyl]-2-yl)-1-methyl-1,4-diazabicyclo[2.2.2]octan-1-ium trifluoromethanesulfonate 78 (1.0 eq) with N-fluoropentachloropyridinium trifluoromethanesulfonate 74 (1.0 eq) and NaHCO$_3$ (2.0 eq) in CD$_3$CN. Filtration through a cotton wool pipette afforded the in situ prepared (2S,3S)-2,3-di([1,1'-biphenyl]-2-yl)-1-fluoro-4-methyl-1,4-diazabicyclo[2.2.2]octane-1,4-diium bis(trifluoromethanesulfonate) which displayed the following characteristic data. $^{19}$F {1H} NMR (376 MHz, CD$_3$CN): δ=+36.5 ([N−F]$^+$), −79.3 (OTf).

The structure of compound 80 is depicted in paragraph [0060] above.

Example 79

(1S,2S)-1,2-Di(naphthalen-1-yl)ethane-1,2-diamine 81

To a solution of (1R,2R)-1,2-bis(2-hydroxylphenyl)-1,2-diaminoethane (2.20 g, 10.0 mmol) in DMSO (50 mL) was added aryl aldehyde (24.0 mmol). The resulting mixture was stirred overnight at room temperature before being poured onto water (150 mL). The aqueous layer was extracted with ether and the combined organic phases were washed with water, dried over MgSO$_4$ and evaporated under reduced pressure. To the resultant diimine intermediate in THF (100 mL) was added 37% HCl (3.0 mL) and the reaction was stirred for 3 hours to obtain a precipitate. The solid was filtered and washed with THF to afford analytically pure dihydrochloride salt. To the salt was added ethyl acetate, saturated aqueous NaHCO3 solution and some NaOH (3M) and the two layers were separated. The aqueous layer was extracted with ethyl acetate and the combined organic extracts were dried and evaporated under reduced pressure to afford (1S,2S)-1,2-di(naphthalen-1-yl)ethane-1,2-diamine as a white solid (2.34 g, 87% yield). $^1$H NMR (400 MHz, CDCl$_3$): δ=1.77 (brs, 4H, NH$_2$), 5.14 (s, 2H), 7.48-7.55 (m, 4H), 7.60 (td, J=7.0 Hz, J=1.2 Hz, 2H), 7.80 (dd, J=8.0 Hz, J=7.1 Hz, 4H), 7.89 (d, J=7.8 Hz, 2H), 8.33 (d, J=8.3 Hz, 2H); $^{13}$C NMR (100.6 MHz, CDCl$_3$): δ=54.3, 22.8, 124.1, 125.4, 125.4, 125.9, 127.6, 129.1, 130.8, 133.9, 139.6; IR (v, cm$^{-1}$): 2869, 1454, 1067; Elemental analysis: Calc. for dihydrochloride salt C$_{22}$H$_{22}$Cl$_2$N$_2$: C, 68.57; H, 5.75; N, 7.27; found: C, 68.58; H, 5.77; N, 7.34; [α]$^{22}_D$ value of dihydrochloride salt is +266.0 (c 0.56, H$_2$O).

Example 80

N,N'-((1S,2S)-1,2-di(naphthalen-1-yl)ethane-1,2-diyl)bis(2-chloroacetamide) 82

To a solution of (1S,2S)-1,2-di(naphthalen-1-yl)ethane-1,2-diamine 81 (1.0 eq) in DCM (40 mL) at 0° C. was added Et$_3$N (5.0 eq.), DMAP (3 mol %) and chloroacetyl chloride (5.0 eq.) The reaction was stirred at room temperature for 3 hours before quenching with water (15 mL) and acidifying with 1M HCl. The aqueous phase was extracted with DCM (3×20 mL) and the combined organic phases dried over MgSO$_4$ and evaporated under reduced pressure. Purification by column chromatography (SiO$_2$, EtOAc/PE 1:1) afforded N,N'-((1S,2S)-1,2-di(naphthalen-1-yl)ethane-1,2-diyl)bis(2-chloroacetamide) as a white solid (3.15 g, 90% yield). $^1$H NMR (400 MHz, CDCl$_3$): δ=4.04 (d, J=16.1 Hz, 2H), 4.11 (d, J=16.1 Hz, 2H), 6.73 (brs, 2H), 7.22 (t, J=6.0 Hz, 2H), 7.25-7.37 (m, 2H), 7.45-7.54 (m, 6H), 7.65 (d, J=6.5 Hz, 2H), 7.76 (d, J=6.5 Hz, 2H), 8.23 (brs, 2H); $^{13}$C NMR (100.6 MHz, CDCl$_3$): δ=42.4, 51.6, 121.7, 123.8, 124.1, 124.9, 126.0, 128.0, 128.1, 130.0, 132.4, 132.9, 165.9; IR (v, cm$^{-1}$): 3268, 1654, 1541, 776; HRMS (ESI$^+$): m/z calc. for C$_{26}$H$_{22}$Cl$_2$N$_2$O$_2$ [M+Na]$^+$ 487.0951, found 487.0959; [α]$^{22}_D$+367 (c 0.28, MeOH); mp: 164-166° C.

Example 81

(2S,3S)-2,3-Di(naphthalen-1-yl)-1,4-diazabicyclo[2.2.2]octane 83

To a solution of N,N'-((1S,2S)-1,2-di(naphthalen-1-yl)ethane-1,2-diyl)bis(2-chloroacetamide) 82 (1.0 eq) in THF (0.1 M) at 0° C. was added BH$_3$.THF (1M solution in THF, 4.0 eq) and the reaction was heated at reflux for 12 hours before cooling to 0° C. and quenching with methanol. The mixture was concentrated in vacuo and acidified with 1 M HCl. The aqueous phase was washed with ether and the organic layer discarded. Following the addition of 3 M NaOH to achieve pH14, the reduced product was extracted into EtOAc and the combined organic layers were dried over MgSO$_4$ and evaporated under reduced pressure. The intermediate was used directly in the next step without further purification.

A solution of diamine in DMF (0.2 M) was heated at reflux for 5 hours before cooling to room temperature and concentrating in vacuo. The crude mixture was dissolved in water, and basified with 3 M NaOH. The aqueous phase was extracted with CHCl$_3$ and the combined organic extracts were washed with brine, dried over MgSO$_4$ and evaporated under reduced pressure. Purification by column chromatography (SiO$_2$, CHCl$_3$/MeOH 97:3) afforded (2S,3S)-2,3-di(naphthalen-1-yl)-1,4-diazabicyclo[2.2.2]octane as a pale yellow solid (683 mg, 51% yield over 2 steps). $^1$H NMR (400 MHz, CDCl$_3$): δ=2.69-2.75 (m, 2H), 2.88-3.00 (m, 2H), 3.00-3.10 (m, 2H), 3.49-3.59 (m, 2H), 5.37 (s, 2H), 7.29 (t, J=7.8 Hz, 2H), 7.47 (d, J=7.3 Hz, 2H), 7.54 (ddd, J=8.0 Hz, J=6.9 Hz, J=1.0 Hz, 2H), 7.68 (ddd, J=8.5 Hz, J=6.8 Hz, J=1.2 Hz, 2H), 7.76 (d, J=8.3 Hz, 2H), 7.88 (d, J=8.1 Hz, 2H), 8.53 (d, J=8.6 Hz, 2H); $^{13}$C NMR (100.6 MHz, CDCl$_3$): δ=41.4, 49.3, 55.6, 123.1, 124.6, 124.6, 125.6, 126.5, 128.6, 128.9, 133.3, 134.4, 134.5; IR (v, cm$^{-1}$): 2932, 2868, 2360, 2341, 771; HRMS (ESI$^+$): m/z calc. for C$_{26}$H$_{24}$N$_2$ [M+H]$^+$: 365.2012, found 365.2008; [α]$^{22}_D$+64 (c 0.5, MeOH); mp: 105-107° C.

Example 82

(2S,3S)-1-Methyl-2,3-di(naphthalen-1-yl)-1,4-diazabicyclo[2.2.2]octan-1-ium trifluoromethanesulfonate 84

To a solution of (2S,3S)-2,3-di(naphthalen-1-yl)-1,4-diazabicyclo[2.2.2]octane 83 (1.0 eq) in Et$_2$O (0.02 M) at 0° C. was added dropwise methyl trifluoromethanesulfonate (1.0 eq). The reaction was stirred for 3 hours, after which the precipitate was collected under vacuum. The resulting solid was washed with ether and acetone to afford (2S,3S)-1-methyl-2,3-di(naphthalen-1-yl)-1,4-diazabicyclo[2.2.2]octan-1-ium trifluoromethanesulfonate as a white solid (150 mg, 95% yield). $^1$H NMR (400 MHz, CD$_3$CN): δ=2.55 (s, 3H), 3.02 (ddd, J=13.7 Hz, J=9.5 Hz, J=2.3 Hz, 1H), 3.16-3.29 (m, 2H), 3.42 (ddd, J=13.6 Hz, J=9.3 Hz, J=7.8 Hz, 1H), 3.54 (dt, J=11.7 Hz, J=9.0 Hz, 1H), 3.80-3.91 (m, 1H), 4.07-4.19 (m, 2H), 5.59 (d, J=10.1 Hz, 1H), 6.06 (d, J=10.1 Hz, 1H), 7.28 (t, J=7.7 Hz, 1H), 7.44-7.54 (m, 2H), 7.58-7.64 (m, 2H), 7.70 (d, J=6.7 Hz, 1H), 7.71 (d, J=6.5 Hz, 1H), 7.77 (d, J=8.0 Hz, 1H), 7.85 (ddd, J=8.6 Hz, J=7.0 Hz, J=1.0 Hz, 1H), 7.90 (d, J=8.5 Hz, 1H), 7.92 (d, J=8.5 Hz, 1H), 8.28 (d, J=7.4 Hz, 1H), 8.35 (d, J=8.6 Hz, 1H), 8.85 (d, J=8.7 Hz, 1H); $^{13}$C NMR (100.6 MHz, CD$_3$CN): δ=40.5, 46.6, 48.9, 50.2, 58.8, 61.7, 63.4, 121.7 (q, J=321.1 Hz, CF$_3$), 122.9, 124.0, 125.0, 125.0, 125.9, 126.0, 126.7, 127.2, 127.3, 128.5, 129.0, 129.2, 130.1, 130.2, 131.0, 132.6, 132.9, 133.7, 134.7, 134.8; $^{19}$F {1H} NMR (376 MHz, CD$_3$CN): δ=−79.3 (TfO); IR (v, cm$^{-1}$): 2932, 2868, 2360; HRMS (ESI$^+$): m/z calc. for C$_{27}$H$_{27}$N$_2$ [M]$^+$: 379.2169, found 379.2165; [α]$^{22}_D$=+303.6 (c 0.52, MeOH); mp: 210-212° C.

Example 83

(2S,3S)-1-Fluoro-4-methyl-2,3-di(naphthalen-1-yl)-1,4-diazabicyclo[2.2.2]octane-1,4-diium bis(trifluoromethanesulfonate) 85

An in situ sample of the fluorinated reagent was prepared by mixing (2S,3S)-1-methyl-2,3-di(naphthalen-1-yl)-1,4-diazabicyclo[2.2.2]octan-1-ium trifluoromethanesulfonate 84 (1.0 eq.) with N-fluoropentachloropyridinium trifluoromethanesulfonate 74 (1.0 eq) and NaHCO$_3$ (2.0 eq) in CD$_3$CN. Filtration through a cotton wool pipette afforded the in situ prepared 2S,3S)-1-Fluoro-4-methyl-2,3-di(naphthalen-1-yl)-1,4-diazabicyclo[2.2.2]octane-1,4-diium bis(trifluoromethanesulfonate) which displayed the following characteristic data. $^{19}$F {1H} NMR (376 MHz, CD$_3$CN): δ=+35.1 ([N–F]$^+$), −79.3 (OTf).

The structure of compound 85 is depicted in paragraph [0060] above.

Example 84

(1S,2S)-1,2-Bis(2-(trifluoromethyl)phenyl)ethane-1,2-diamine dihydrochloride 86

To a solution of (1R,2R)-1,2-bis(2-hydroxylphenyl)-1,2-diaminoethane (1.00 g, 4.09 mmol) in DMSO (80 mL) was added 2-(trifluoromethyl)benzaldehyde (1.30 mL, 9.82 mmol). The resulting mixture was stirred overnight at room temperature before being poured onto water (150 mL). The aqueous layer was extracted with ether and the combined organic phases were washed with water, dried over MgSO$_4$ and evaporated under reduced pressure. To the resultant diimine intermediate in THF (100 mL) was added 37% HCl (3.0 mL) and the reaction was stirred for 3 hours before concentrating in vacuo. The resultant solid was dissolved in water (25 mL) and washed with ether. The aqueous layer was then made basic with 3M NaOH and extracted with EtOAc. The organic layer was further washed with 1M NaOH and then extracted with 1M HCl. The aqueous layer was evaporated under reduced pressure to afford (1S,2S)-1,2-bis(2-(trifluoromethyl)phenyl)ethane-1,2-diamine dihydrochloride as a pale yellow solid (920 mg, 53% yield). $^1$H NMR (400 MHz, DMSO-$d_6$): δ=5.52 (s, 2H), 7.53 (t, J=7.6 Hz, 2H), 7.67 (d, J=8.0 Hz, 2H), 7.71 (t, J=7.7 Hz, 2H), 8.07 (d, J=7.9 Hz, 2H), 9.46 (brs, 6H); $^{13}$C NMR (125.8 MHz, DMSO-$d_6$): δ=52.1, 123.6 (q, J=274.7 Hz), 126.5 (q, J=5.5 Hz), 127.5 (q, J=29.7 Hz), 130.2, 130.3, 131.5, 133.1; $^{19}$F {1H} NMR (376.5 MHz, CD$_3$CN): δ=−55.9; IR (v, cm$^{-1}$): 3546; HRMS (ESI$^+$, m/z): [$C_{16}H_{15}F_6N_2$]$^+$(M+H)$^+$calc. 349.1134, found 349.1134; mp: 198-199° C.

Example 85

N,N'-((1S,2S)-1,2-bis(2-(trifluoromethyl)phenyl)ethane-1,2-diyl)bis(2-chloroacetamide) 87

To a suspension of (1S,2S)-1,2-bis(2-(trifluoromethyl)phenyl)ethane-1,2-diamine dihydrochloride 86 (700 mg, 1.65 mmol) in DCM (20 mL) at 0° C. was added Et$_3$N (1.84 mL, 13.2 mmol) followed by DMAP (10 mg) and chloroacetyl chloride (527 µL, 6.62 mmol). The reaction was stirred overnight before quenching with water (50 mL) and extracting into DCM (3×100 mL). The combined organic layers were washed with brine, dried over MgSO$_4$ and evaporated under reduced pressure. Purification by column chromatography (SiO$_2$, EtOAc/PE 2:3) afforded N,N'-((1S,2S)-1,2-bis(2-(trifluoromethyl)phenyl)ethane-1,2-diyl)bis(2-chloroacetamide) as a white solid (743 mg, 90% yield).

$^1$H NMR (400 MHz, CDCl$_3$): δ=4.07 (d, J=15.1 Hz, 2H), 4.12 (d, J=15.1 Hz, 2H), 5.97-6.05 (m, 2H), 6.93 (d, J=5.6 Hz, 2H), 7.42 (t, J=7.8 Hz, 2H), 7.56 (d, J=7.9 Hz, 2H), 7.68 (t, J=7.8 Hz, 2H), 8.08 (d, J=7.9 Hz, 2H); $^{13}$C NMR (100.6 MHz, CDCl$_3$): δ=42.3, 55.0, 123.5 (q, J=272.2 Hz), 126.2 (q, J=6.0 H), 128.7, 128.8, 129.7, 133.0, 136.1, 166.5; $^{19}$F {11-1} NMR (376.5 MHz, CDCl$_3$): δ=−58.5; IR (v, cm$^{-1}$): 3296, 1662, 1311, 1112; HRMS (ESI$^+$): m/z calc. for $C_{20}H_{16}Cl_2F_6N_2NaO_2$ ([M+Na]$^+$): 523.0385, found 523.0383; [α]$^{22}_D$+257 (c 0.165, MeOH) mp: 70-72° C.

Example 86

(2S,3S)-2,3-Bis(2-(trifluoromethyl)phenyl)-1,4-diazabicyclo[2.2.2]octane 88

To a solution of N,N'-(1S,2S)-1,2-bis(4-(trifluoromethyl)phenyl)ethane-1,2-diyl)bis(2-chloroacetamide) 87 (740 mg, 1.48 mmol) in THF (22 mL) at 0° C. was added dropwise BH$_3$.THF (1M in THF, 6.0 mL, 5.92 mmol) and the reaction was heated at reflux for 12 hours. The reaction mixture was cooled to room temperature and MeOH was added dropwise and stirred for 5 hours at room temperature. Then the solvent was evaporated under reduced pressure, HCl (1M) was added and the mixture was stirred at the same temperature for 12 hours. NaOH (3M) was added to bring the reaction mixture to pH 14, which was then extracted with DCM. The combined organic extracts were dried over MgSO$_4$ and evaporated to furnish the crude diamine, which was used in the next step with no further purification. The crude product (759 mg) was dissolved in dimethylformamide (23 mL) and heated at 150° C. for 12 hours. The solvent was concentrated under reduced pressure and the residue was dissolved in water. The aqueous phase was treated with 3M NaOH to reach pH 14 and extracted with DCM. The combined organic extracts were dried over MgSO$_4$ and evaporated under reduced pressure. Purification by column chromatography (SiO$_2$, CHCl$_3$/MeOH 99.5:0.5) afforded (2S,3S)-2,3-bis(2-(trifluoromethyl)phenyl)-1,4-diazabicyclo[2.2.2]octane as a colourless oil (295 mg, 50% yield over 2 steps). $^1$H NMR (400 MHz, CDCl$_3$): δ=2.64 (ddd, J=9.3 Hz, 8.3 Hz, 3.7 Hz, 2H), 2.91-3.01 (m, 2H), 3.04-3.15 (m, 2H), 3.37 (ddt, J=8.8 Hz, 3.2 Hz, 2.4 Hz, 2H), 4.92 (s, 2H), 7.34 (t, J=7.6 Hz, 2H), 7.54 (t, J=7.6 Hz, 2H), 7.69 (d, J=7.6 Hz, 2H), 7.79 (d, J=7.8 Hz, 2H); $^{13}$C NMR (100.6 MHz, CDCl$_3$): δ=39.9, 49.9, 56.2, 124.5 (q, J=274.9 Hz, CF$_3$), 127.4 (q, J=6.4 Hz), 127.8, 127.9, 130.6 (q, J=29.2 Hz), 131.4, 136.6; $^{19}$F {11-1} NMR (376.5 MHz, CDCl$_3$): δ=−58.1; IR (v, cm$^{-1}$): 1690, 1380, 1210; HRMS (ESI$^+$): m/z calc. for $C_{20}H_{19}F_6N_2$ ([M+H]$^+$): 401.1447, found 401.1444; [α]$^{22}_D$+21 (c 0.15, MeOH).

Example 87

(2S,3S)-1-Methyl-2,3-bis(2-(trifluoromethyl)phenyl)-1,4-diazabicyclo[2.2.2]octan-1-ium trifluoromethanesulfonate 89

To a solution of (2S,3S)-2,3-bis(2-(trifluoromethyl)phenyl)-1,4-diazabicyclo[2.2.2]octane 88 (1.0 eq) in DCM (0.02 M) at −78° C., methyl trifluoromethanesulfonate (1.0 eq) in DCM (0.2M) was added dropwise (10 min addition time) at the same temperature and the reaction mixture was stirred for 4 h at −78° C. the solvent was evaporated under reduced pressure before diethyl ether was added and the resulting solid was recovered by filtration and dried under high vacuum to afford (2S,3S)-1-methyl-2,3-bis(2-(trifluoromethyl)phenyl)-1,4-diazabicyclo[2.2.2]octan-1-ium trifluoromethane sulfonate as a white solid (139 mg, 98% yield). $^1$H NMR (400 MHz, CD$_3$CN): δ=2.70 (s, 3H), 3.14 (ddd, J=10.0 Hz, 8.3 Hz, 3.9 Hz, 1H), 3.37-3.56 (m, 3H), 3.64-3.71 (m, 1H), 3.77-3.94 (m, 3H), 5.03 (d, J=9.8 Hz, 1H), 5.14 (d, J=9.8 Hz, 1H), 7.54 (t, J=7.8 Hz, 1H), 7.72 (dd, J=8.5, 8.3 Hz, 3H), 7.82 (d, J=7.8 Hz, 1H), 7.88 (t, J=7.6 Hz, 1H), 8.00 (d, J=7.8 Hz, 1H), 8.24 (d, J=7.8 Hz, 1H); $^{13}$C NMR (100.6 MHz, CD$_3$CN): δ=40.2, 48.7, 50.0, 51.2, 60.7, 62.9, 66.9, 124.5 (q, J=274.0 Hz, CF$_3$), 125.0 (q, J=274.8 Hz, CF$_3$), 128.3 (q, J=5.6 Hz), 129.1 (q, J=6.4 Hz), 130.2, 130.3 (q, J=29.8 Hz), 130.8, 131.5, 131.6 (q, J=29.6 Hz), 133.0, 133.1, 133.4, 134.9; $^{19}$F {1H} NMR (376.5 MHz, CD$_3$CN): δ=−55.3, −58.7, −79.2; IR (v, cm$^{-1}$): 1225, 1054, 985; HRMS (ESI$^+$): m/z calc. for $C_{21}H_{21}F_6N_2$ ([M]$^+$): 415.1603, found 415.1601; [α]$^{22}_D$−3.7 (c 0.25, MeOH); mp: 99-101° C.

Example 88

(2S,3S)-1-Fluoro-4-methyl-2,3-bis(2-(trifluoromethyl)phenyl)-1,4-diazabicyclo[2.2.2]octane-1,4-diium bis(trifluoromethanesulfonate) 90

An in situ sample of the fluorinated reagent was prepared by mixing (2S,3S)-1-methyl-2,3-bis(2-(trifluoromethyl)phenyl)-1,4-diazabicyclo[2.2.2]octan-1-ium trifluoromethanesulfonate 89 (1.0 eq) with N-fluoropentachloropyridinium trifluoromethanesulfonate 74 (1.0 eq) and NaHCO$_3$ (2.0 eq) in CD$_3$CN. Filtration through a cotton wool pipette afforded the in situ prepared (2S,3S)-1-Fluoro-4-methyl-2,3-bis(2-

(trifluoromethyl)phenyl)-1,4-diazabicyclo[2.2.2]octane-1,4-diium bis(trifluoromethane sulfonate) which displayed the following characteristic data. $^{19}$F {1H} NMR (376 MHz, CD$_3$CN): δ=+37.3 (q, J=13.2 Hz, 1F, [N—F]$^+$), −55.1 (s, 3F, CF$_3$), −56.5 (d, J=13.2 Hz, 3F), −79.3 (OTf). The structure of compound 90 is depicted in paragraph [0060] above.

Example 89

(1S,2S)-1,2-Di(naphthalen-2-yl)ethane-1,2-diamine dihydrochloride 91

To a suspension of (1R,2R)-1,2-bis(2-hydroxylphenyl)-1,2-diaminoethane (1.57 g, 6.43 mmol) in ethanol (24 mL) was added 2-naphthaldehyde (2.40 g, 15.4 mmol). After a few minutes the solution became clear and after 2-3 hours a white solid precipitated. The solid was collected by vacuum filtration, washed with ethanol and dried. The solid was dissolved in THF (75 mL) and 36% HCl (2.5 mL) was added dropwise. The solution was stirred for 3 hours to (1S,2S)-1,2-di(naphthalen-2-yl)ethane-1,2-diamine dihydrochloride as a white precipitate, which was used without purification (1.86 g, 75% yield). $^1$H NMR (400 MHz, DMSO-d$_6$): δ=5.40 (s, 2H), 7.46-7.51 (m, 4H), 7.54 (dd, J=8.7 Hz, J=1.5 Hz, 2H), 7.74-7.84 (m, 6H), 7.99 (s, 2H), 9.46 (brs, 6H); $^{13}$C NMR (100.6 MHz, DMSO-d$_6$): δ=57.3, 126.0, 127.1, 127.4, 128.0, 128.4, 128.6, 129.3, 131.2, 132.6, 133.1; IR (v, cm$^{-1}$): 3595; HRMS (ESI$^+$, m/z): [C$_{22}$H$_{21}$N$_2$]$^+$ (M+H)$^+$calc. 313.1699, found 313.1699; mp: 215-216° C.

Example 90

N,N'-(1S,2S)-1,2-di(naphthalen-2-yl)ethane-1,2-diyl)bis(2-chloroacetamide) 92

To a suspension of (1S,2S)-1,2-di(naphthalen-2-yl)ethane-1,2-diamine dihydrochloride 91 (1.20 g, 3.11 mmol) in DCM (50 mL) at 0° C. was added Et$_3$N (3.47 mL, 24.9 mmol) followed by DMAP (10 mg) and chloroacetyl chloride (992 µL, 12.5 mmol). The reaction was stirred overnight before quenching with water (100 mL) and extracting into DCM (3×300 mL)—Note: product is very insoluble. The combined organic layers were washed with brine, dried over MgSO$_4$ and evaporated under reduced pressure. Purification by trituation (MeCN) afforded N,N'-((1S,2S)-1,2-di(naphthalen-2-yl)ethane-1,2-diyl)bis(2-chloroacetamide) as a white solid (1.44 g, 3.11 mmol, 99% yield). $^1$H NMR (400 MHz, DMSO-d$_6$): δ=4.08 (d, J=13.0 Hz, 2H), 4.13 (d, J=13.0 Hz, 2H), 5.51-5.60 (m, 2H), 7.39-7.50 (m, 6H), 7.71-7.83 (m, 8H), 9.02-9.10 (m, 2H); $^{13}$C NMR (100.6 MHz, DMSO-d$_6$): δ=43.2, 57.7, 126.0, 126.4, 126.6, 126.9, 127.9, 128.1, 128.1, 132.6, 133.0, 137.5, 166.2; IR (v, cm$^{-1}$): 3398, 1645; HRMS (ESI$^+$, m/z): [C$_{26}$H$_{22}$Cl$_2$N$_2$NaO$_2$]$^+$ (M+Na)$^+$calc. 487.0951, found 487.0949; mp: 249-251° C.

Example 91

(2S,3S)-2,3-Di(naphthalen-2-yl)-1,4-diazabicyclo[2.2.2]octane 93

To a solution of N,N'-((1S,2S)-1,2-di(naphthalen-2-yl)ethane-1,2-diyl)bis(2-chloroacetamide) 92 (1.43 g, 3.07 mmol) in THF (0.1 M) at 0° C. was added BH$_3$.THF (1M solution in THF, 12.3 mL, 12.3 mmol) and the reaction was heated at reflux for 12 hours before cooling to 0° C. and quenching with methanol. The mixture was concentrated in vacuo to dryness and acidified with 1 M HCl. The aqueous phase was washed with ether and the organic layer discarded. Following the addition of 3 M NaOH to achieve pH14, the reduced product was extracted into EtOAc and the combined organic layers were dried over MgSO$_4$ and evaporated under reduced pressure. The intermediate was used directly in the next step without further purification. A solution of diamine in DMF (0.2 M) was heated at reflux for 5 hours before cooling to room temperature and concentrating in vacuo. The crude mixture was dissolved in water, and basified with 3 M NaOH. The aqueous phase was extracted with CHCl$_3$ and the combined organic extracts were washed with brine, dried over MgSO$_4$ and evaporated under reduced pressure. Purification by column chromatography (SiO$_2$, CHCl$_3$/MeOH 97:3) afforded (2S,3S)-2,3-di(naphthalen-2-yl)-1,4-diazabicyclo[2.2.2]octane as a white solid (470 mg, 1.29 mmol, 42 yield over 2 steps). $^1$H NMR (400 MHz, CDCl$_3$): δ=2.65-2.75 (m, 2H), 2.81-2.93 (m, 2H), 3.02-3.19 (m, 4H), 4.47 (s, 2H), 7.44-7.53 (m, 4H), 7.70 (dd, J=8.6 Hz, J=1.7 Hz, 2H), 7.78-7.84 (m, 2H), 7.84-7.90 (m, 4H), 7.93 (s, 2H); $^{13}$C NMR (100.6 MHz, CDCl$_3$): δ=41.3, 49.6, 62.5, 125.8, 125.9, 126.1, 126.7, 127.6, 128.1, 128.1, 132.7, 133.3, 138.8; IR (v, cm$^{-1}$): 3052 (m, C—H), 2935 (m, C—H), 2866 (m, C—H), 858 (m, C—N), 809 (m, C—C); HRMS (ESI$^+$, m/z): [C$_{26}$H$_{25}$N$_2$]$^+$(M+H)$^+$calc. 365.2012, found 365.2000.

Example 92

(2S,3S)-1-Methyl-2,3-di(naphthalen-2-yl)-1,4-diazabicyclo[2.2.2]octan-1-ium trifluoromethanesulfonate 94

To a solution of (2S,3S)-2,3-di(naphthalen-2-yl)-1,4-diazabicyclo[2.2.2]octane 93 (1.0 eq) in DCM (0.02 M) at −78° C., methyl trifluoromethanesulfonate (1.0 eq) in DCM (0.2M) was added dropwise (10 min addition time) at the same temperature and the reaction mixture was stirred for 4 h at −78° C. the solvent was evaporated under reduced pressure before diethyl ether was added and the resulting solid was recovered by filtration and dried under high vacuum to afford (2S,3S)-1-methyl-2,3-di(naphthalen-2-yl)-1,4-diazabicyclo[2.2.2]octan-1-ium trifluoromethanesulfonate as a white solid (430 mg, 96% yield). $^1$H NMR (400 MHz, CD$_3$CN): δ=2.71 (s, 3H), 3.16-3.28 (m, 3H), 3.47-3.59 (m, 2H), 3.60-3.69 (m, 1H), 3.69-3.78 (m, 1H), 3.88-3.99 (m, 1H), 5.11 (d, J=9.6 Hz, 1H), 5.15 (d, J=9.6 Hz, 1H), 7.49-7.55 (m, 3H), 7.65-7.70 (m, 2H), 7.83-7.95 (m, 5H), 7.99-8.05 (m, 1H), 8.06-8.11 (m, 1H), 8.14 (d, J=8.6 Hz, 1H), 8.50 (s, 1H); $^{13}$C NMR (100.6 MHz, CD$_3$CN): δ=40.5, 46.8, 49.7, 50.3, 58.1, 63.3, 72.2, 121.7 (q, J=321.1 Hz, CF$_3$), 126.1, 126.4, 127.1, 127.2, 127.9, 128.0, 128.3, 128.3, 128.3, 128.6, 128.7, 129.0, 129.0, 129.2, 130.3, 133.4, 133.5, 133.8, 134.8, 134.9; $^{19}$F {11-1} NMR (376 MHz, CD$_3$CN): δ=−79.3; IR (v, cm$^{-1}$): 1255, 1029, 819; HRMS (ESI$^+$, m/z): [C$_{27}$H$_{27}$N$_2$]$^+$(M)$^+$calc. 379.2169, found 379.2165; mp: 213-214° C.

Example 93

(2S,3S)-1-Fluoro-4-methyl-2,3-di(naphthalen-2-yl)-1,4-diazabicyclo[2.2.2]octane-1,4-diium bis(trifluoromethanesulfonate) 95

An in situ sample of the fluorinated reagent was prepared by mixing afford (2S,3S)-1-methyl-2,3-di(naphthalen-2-yl)-1,4-diazabicyclo[2.2.2]octan-1-ium trifluoromethanesulfonate 94 (1.0 eq.) with N-fluoropentachloropyridinium trifluoromethanesulfonate 74 (1.0 eq) and NaHCO$_3$ (2.0 eq) in CD$_3$CN. Filtration through a cotton wool pipette afforded the in situ prepared (2S,3S)-1-fluoro-4-methyl-2,3-di(naphthalen-2-yl)-1,4-diazabicyclo[2.2.2]octane-1,4-diium bis(trifluoromethanesulfonate) which displayed the following characteristic data. $^{19}$F {1H} NMR (376 MHz, CD$_3$CN): δ=+35.9 ([N–F]$^+$), –79.3 (OTf).

The structure of compound 95 is depicted in paragraph [0060] above.

Example 94

(R)-Methyl 2-((R)-2-(tert-butoxycarbonylamino)-2-phenylacetamido)-2-phenylacetate 96

Dipeptide (R)-methyl 2-((R)-2-(tert-butoxycarbonylamino)-2-phenylacetamido)-2-phenylacetate was prepared from (R)—N-boc-1-phenylglycine (8.00 g, 31.8 mmol) and (R)-1-phenylglycine methyl ester hydrochloride (7.70 g, 38.2 mmol) according to a similar procedure used in Examples 9, 13 and 14 above. Purification of the crude product by silica gel column chromatography the entitled dipeptide as a white solid (11.5 g, 91%). $^1$H NMR (400 MHz, CDCl$_3$) δ 1.40 (s, 9H, C(CH$_3$)$_3$), 3.67 (s, 3H, OCH$_3$), 5.21 (br s, 1H, NIA 5.50 (d, 1H, J=6.8 Hz, NHCH), 5.72 (br s, 1H, NH), 6.83 (d, 1H, J=6.6 Hz, NHCH), 7.34-7.39 (m, 10H, ArH); $^{13}$C NMR (100.6 MHz, CDCl$_3$) δ 28.2 (C(CH$_3$)$_3$), 52.38 (OCH$_3$), 56.7 (NHCH), 58.5 (NHCH), 80.1 (C(CH$_3$)$_3$), 127.3 (2×PhC), 128.4 (2×PhC), 128.6 (2×PhC), 128.9 (2×PhC), 130.0 (2×PhC), 136.0 (C), 137.8 (C), 154.3 (NHCOCH), 169.5 (CO), 170.7 (CO); IR (ν), KBr/cm$^{-1}$): 1736 (C=O), 1638 (NC=O); HRMS (ESI): m/z calcd for C$_{22}$H$_{26}$N$_2$O$_5$ [M+Na]$^+$421.1731, found 421.1734; [α]$^{22}_D$+144.5 (c 1, MeOH); mp 89-91° C.

Example 95

(3R,6R)-3,6-Bis(phenyl)piperazine-2,5-dione 97

Diketopiperazine (3R,6R)-3,6-bis(phenyl)piperazine-2,5-dione 97 was prepared from (R)-methyl 2-((R)-2-(tert-butoxycarbonylamino)-2-phenylacetamido)-2-phenylacetate 96 (6.50 g, 16.3 mmol) according to a similar procedure used for Examples 10, 15 and 16 above. After completion, work-up and purification afforded the final diketopiperazine as a white solid (3.49 g, 80%). $^1$H NMR (400 MHz, DMSO-d6) δ 5.08 (s, 2H, NHCH), 7.23-7.30 (m, 10H, ArH), 8.68 (d, 2H, J=2.7 Hz, NH); $^{13}$C NMR (100.6 MHz, DMSO-d6) δ 58.3 (2×NHCH), 126.8 (2×PhC), 127.8 (4×PhC), 128.1 (4×PhC), 138.4 (2×C), 165.9 (2×NHCO); IR (ν), KBr/cm$^{-1}$): 3080 (C—H), 1678 (C=O), 1665 (C=O), 1448 (C=C); HRMS (ESI): m/z calcd for C$_{16}$H$_{14}$N$_2$O$_2$ [M+Na]$^+$ 289.0944; [α]$^{22}_D$+68.6 (c 1, DMSO); found 289.0947; mp 280-282° C.

Example 96

(2R,5R)-2,5-Bis(phenylpiperazine) 98

Piperazine (2R,5R)-2,5-bis(phenylpiperazine) 98 was prepared from (3R,6R)-3,6-bis(phenyl)piperazine-2,5-dione 97 (1.00 g, 3.76 mmol) according to a similar procedure used for Examples 17, 18 and 19 above. After completion, work-up and purification gave the above piperazine as a colourless oil (0.68 g, 76%). $^1$H NMR (400 MHz, CDCl$_3$) δ 1.93 (br s, 2H, NH), 3.14 (dd, 2H, J=12.1 Hz, J=3.6 Hz, NHCH$_2$), 3.27 (dd, 2H, J=12.1 Hz, J=6.0 Hz, NHCH$_2$), 4.00 (dd, 2H, J=5.9, J=3.7 Hz, NHCH), 7.27 (t, 2H, J=7.3 Hz, ArH), 7.36 (t, 2H, J=7.7 Hz, ArCH), 7.57-7.59 (m, 4H, ArH); $^{13}$C NMR (100.6 MHz, CDCl$_3$) δ 49.0 (2×NHCH2), 57.7 (2×NHCH), 126.9 (2×PhC) 127.6 (4×PhC), 128.2 (4×PhC), 142.8 (2×C); IR (ν), neat/cm$^{-1}$): 3320 (NH), 3020 (C—H), 2700 (C—H), 1455 (C=C); HRMS (ESI): m/z calcd for C$_{16}$H$_{18}$N$_2$ [M]$^+$238.1470, found 238.1474.

Example 97

(1R,2R,4R,5R)-2,5-diphenyl-1,4-diazabicyclo[2.2.2]octane 99 and (1S,2R,4S,5R)-2,5-diphenyl-1,4-diazabicyclo[2.2.2]octane 100

Diazabicyclo-octanes were prepared from (2R,5R)-2,5-diphenylpiperazine 98 (300 mg, 1.25 mmol) according to a similar procedure used for its parent compounds. After 12 hours, work-up and purification gave the entitled compounds as solids. (1S,2R,4S,5R)-2,5-diphenyl-1,4-diazabicyclo[2.2.2]octane 99 (55.2 mg, 17%). $^1$H NMR (400 MHz, CDCl$_3$) δ 2.57-2.60 (m, 2H, CH$_2$), 2.81-2.83 (m, 2H, CH$_2$), 3.15 (dd, 2H, J=13.0, J=8.5 Hz, CH$_2$), 3.71 (dd, 2H, J=13.0, J=8.8 Hz, CH$_2$), 4.09 (t, 2H, J=8.8 Hz, NCH), 7.25-7.36 (m, 2H, ArH), 7.38-7.45 (m, 8H, ArH); $^{13}$C NMR (100.6 MHz, CDCl$_3$) δ: 41.3 (CH$_2$), 55.1 (CH$_2$), 56.9 (CH), 126.5 (2×ArC), 126.7 (4×ArC), 128.2 (4×ArC), 141.3 (2×C); IR (ν), cm$^{-1}$): 2930, 1495, 1445, 1060, 800, 745, 735, 700; HRMS (ESI): m/z calcd for C$_{18}$H$_{20}$N$_2$ ([M+H]$^+$): 265.1705, found 265.1708; [α]$^{22}_D$=–76.8 (c 0.49, CHCl$_3$); mp 153-154° C.

(1R,2R,4R,5R)-2,5-diphenyl-1,4-diazabicyclo[2.2.2]octane 100 (189 mg, 17%): $^1$H NMR (400 MHz, CDCl$_3$) δ 2.97 (dd, 2H, J=13.4, J=9.0 Hz, CH$_2$), 3.11 (s, 4H, NCH$_2$), 3.25 (ddd, 2H, J=13.4, J=9.0, J=1.5 Hz, CH$_2$), 3.92 (t, 2H, H=9.0 Hz, NCH), 7.12-7.31 (m, 10H); $^{13}$C NMR (100.6 MHz, CDCl$_3$) δ 47.5 (CH$_2$), 48.8 (CH$_2$), 56.4 (CH), 126.7 (2×ArC), 126.9 (4×ArC), 128.4 (4×ArC), 141.3 (2×C); IR (ν), cm$^{-1}$): 2880, 1600, 1490, 1175, 810, 725, 700; HRMS (ESI): m/z calcd for C$_{18}$H$_{20}$N$_2$ ([M+H]$^+$): 265.1705, found 265.1710; [α]$^{22}_D$=–140.2 (c 0.52, CHCl$_3$); mp 208-209° C.

Example 98

(1S,2R,4S,5R)-1-Methyl-2,5-diphenyl-4-aza-1-azoniabicyclo[2.2.2]octane trifluoromethanesulfonate 101

(1S,2R,4S,5R)-1-Methyl-2,5-diphenyl-4-aza-1-azoniabicyclo[2.2.2]octane trifluoromethanesulfonate 101 was obtained by dropwise addition of methyl trifluoromethanesulfonate to a solution of (1S,2R,4S,5R)-2,5-diphenyl-1,4-diazabicyclo[2.2.2]octane 99 in Et$_2$O at 0° C. for 1 h, then for 2 h at r.t. The resulting precipitate was filtered and washed with acetone (2×10 mL) to afford (1S,2R,4S,5R)-1-methyl-2,5-diphenyl-4-aza-1-azoniabicyclo[2.2.2]octane trifluoromethanesulfonate (139 mg, 98%); 1H NMR (400 MHz, CDCl$_3$) δ 2.63 (s, 3H, CH$_3$), 3.29 (dd, 1H, J=14.6, J=9.3 Hz, CH$_2$), 3.40-3.46 (m, 2H, CH$_2$), 3.52-3.54 (m, 3H, CH$_2$), 3.58-3.67 (m, 1H, CH$_2$), 3.74-3.79 (m, 1H). 4.55-4.59 (m, 2H, NCH), 7.23-7.31 (m, 2H, ArH), 7.40-7.42 (m, 2H, ArH), 7.45-7.49 (m, 2H), 7.50-7.58 (m, 4H); $^{13}$C NMR (100.6 MHz, CDCl$_3$) δ: 46.8 (CH$_2$), 47.6 (CH$_2$), 49.8 (CH$_3$), 56.0 (CH), 57.9 (CH$_2$), 68.7 (CH$_2$), 123.0 (q, J=320.1 Hz, CF$_3$), 127.1 (2×ArC), 129.0 (4×ArC), 130.3 (4×ArC), 132.1 (2×C); $^{19}$F {1H} NMR (376 MHz, CDCl$_3$) δ–79.3 (TfO); IR (ν), cm$^{-1}$: 2930, 1495, 1445, 1060, 800, 745; HRMS (ESI):

m/z calcd for $C_{19}H_{23}N_2$ [M]$^+$: 279.1856, found 279.1853; $[\alpha]^{22}{}_D$=−55.2 (c 0.55, MeOH); mp 105-107° C.

Example 99

(1R,2R,4R,5R)-1-Methyl-2,5-diphenyl-4-aza-1-azoniabicyclo[2.2.2]octane trifluoromethanesulfonate 102

(1R,2R,4R,5R)-1-Methyl-2,5-diphenyl-4-aza-1-azoniabicyclo[2.2.2]octane trifluoromethanesulfonate 102 was obtained by dropwise addition of methyl trifluoromethanesulfonate to a solution of (1R,2R,4R,5R)-2,5-diphenyl-1,4-diazabicyclo[2.2.2]octane 100 in Et$_2$O at 0° C. for 1 h, then for 2 h at r.t. The resulting precipitate was filtered and washed with acetone (2×10 mL) to afford the entitled product (98 mg, 89%): $^1$H NMR (400 MHz, CDCl$_3$) δ 2.86 (s, 3H, CH$_3$), 4.04 (s, 4H, CH$_2$), 4.47 (d, 4H, J=9.9 Hz, CH$_2$), 5.44 (t, 2H, J=9.6 Hz, CH$_2$), 7.65-7.69 (m, 4H, ArH), 7.71-7.75 (m, 2H), 7.82 (d, 4H, J=9.9 Hz); $^{13}$C NMR (100.6 MHz, CDCl$_3$) δ 49.9 (CH$_2$), 50.6 (CH$_3$), 60.4 (CH$_2$), 67.5 (CH), 123.0 (q, 1 JC−F=320.1 Hz, CF$_3$), 126.8 (2×ArC), 131.1 (4×ArC), 132.5 (4×ArC), 133.7 (2×C); $^{19}$F {1H} NMR (376 MHz, CDCl$_3$) δ−79.3 (TfO); IR (v), cm$^{-1}$): 2880, 1600, 1490, 1175, 810; HRMS (ESI): m/z calcd for $C_{19}H_{23}N_2$ [M]$^+$: 279.1856, found 279.1858; $[\alpha]^{22}{}_D$=−39.7 (c 0.50, MeOH); mp 109-110° C.

Example 100

(1R,2S,4R,5S)-2,5-Dibenzyl-1-methyl-4-aza-1-azoniabicyclo[2.2.2]octane trifluoromethanesulfonate 103

(1R,2S,4R,5S)-2,5-dibenzyl-1-methyl-4-aza-1-azoniabicyclo[2.2.2]octane trifluoromethanesulfonate salt 103 was obtained by dropwise addition of methyl trifluoromethanesulfonate to a solution of the neutral disubstituted dabco 23a in Et$_2$O at 0° C. for 1 h, then for 2 h at r.t. The resulting precipitate was filtered and washed with acetone (2×10 mL) to afford the entitled product (57 mg, 97%). $^1$H NMR (500 MHz, CDCl$_3$) δ 3.01-3.04 (m, 2H, CH$_2$), 3.16 (s, 3H, CH$_3$), 3.43-3.47 (m, 2H), 3.51-3.56 (m, 2H), 3.72-3.84 (m, 4H, CH$_2$), 4.07-4.11 (m, 2H), 4.36 (d, 2H, J=9.3 Hz), 7.34-7.39 (m, 10H, ArH); $^{13}$C NMR (125.8 MHz, CDCl$_3$) δ 32.5 (2 s CH2), 50.1 (2 s CH2), 50.6 (CH$_3$), 61.1 (2×CH2), 63.0 (CH), 122.0 (q, 1 JC-F=320.1 Hz, CF$_3$), 129.1 (2×ArC), 130.2 (4×ArC) 130.5 (4×ArC), 132.5 (2×C); $^{19}$F {1H} NMR (376 MHz, CDCl$_3$) δ−79.3 (TfO); IR (v), neat/cm$^{-1}$): 3060 (C—H), 2965 (C—H), 2809, 1460 (C=C); HRMS (ESI): m/z calcd for $C_{21}H_{27}N_2$ [M]+307.2169, found 307.2165; $[\alpha]^{22}{}_D$=+57.2 (c 0.55 MeOH).

Example 101

(1S,2S,4S,5S)-2,5-Dibenzyl-1-methyl-4-aza-1-azoniabicyclo[2.2.2]octane trifluoromethanesulfonate 104

(1S,2S,4S,5S)-2,5-dibenzyl-1-methyl-4-aza-1-azoniabicyclo[2.2.2]octane trifluoromethanesulfonate 104 was obtained by dropwise addition of methyl trifluoromethanesulfonate to a solution of the neutral disubstituted dabco 23b in Et$_2$O at 0° C. for 1 h, then for 2 h at r.t. The resulting precipitate was filtered and washed with acetone (2×10 mL) to afford the entitled product (52 mg, 98%); IR (v), neat/cm$^{-1}$): 3055 (C—H), 2960 (C—H), 2812 (C—H), 1465 (C=C); $^1$H NMR (500 MHz, CDCl$_3$) δ 3.15 (s, CH$_3$), 3.45-2.49 (m, 5H), 3.63-3.68 (m, 3H), 3.96 (s, 4H), 4.39-4.43 (m, 2H), 7.38-7.48 (m, 10H, ArH); $^{13}$C NMR (100.6 MHz, CDCl$_3$) δ 31.7 (2×CH2), 49.8 (CH$_3$), 54.8 (2×CH$_2$), 55.3 (2×CH$_2$), 63.8 (2×NCH), 123.0 (q, 1 JC−F=320.1 Hz, CF$_3$), 128.6 (2×ArC) 129.6 (4×ArC), 130.0 (4×ArC), 132.1 (2×C); $^{19}$F {1H} NMR (376 MHz, CDCl$_3$) δ−79.3 (TfO); mp 69-65° C.; $[\alpha]^{22}{}_D$=+91.2 (c 0.56, MeOH); HRMS (ESI): m/z calcd for $C_{21}H_{27}N_2$ [M]$^+$307.2169, found 307.2165.

Example 102

General Procedure for the Formation of N—F Reagents using F$_2$ Gas

A solution of substituted-4-aza-1-azoniabicylo[2.2.2]octane salt (1 eq) and sodium trifluoromethanesulfonate (1 eq) or lithium tetrafluoroborate (1 eq) in acetonitrile (0.02 M) was placed in a small PTFE reactor. The mixture was purged with N$_2$ and cooled to −35° C. Elemental F$_2$ as a homogeneous 1:9 (v/v) mixture with N$_2$ was introduced at a flow rate of 15 mL/min into the rapidly stirred mixture via PTFE tubing at −35° C. The reaction was monitored by $^{19}$F NMR. The mixture was allowed to warm to room temperature, before filtration to remove sodium fluoride or lithium fluoride, and the solution was concentrated under reduced pressure. Purification by recrsytallisation (Et$_2$O/MeOH 4:1) afforded the desired product.

| Entry | Compounds | Equivalents of F$_2$ | Products | Chemical Shift (ppm) NF$^+$ | Chemical Shift (ppm) TfO$^-$ | Conversion[a] (%) |
|---|---|---|---|---|---|---|
| 1 | 101 | 2 | 105 | +49.0 | −79.3 | 69 |
| 2 | 101 | 3 | 105 | +49.0 | −79.3 | 72 |
| 3 | 101 | 4 | 105 | +49.0 | −79.3 | 76 |
| 4 | 102 | 3 | 106 | +33.0 | −79.3 | 65 |
| 5 | 102 | 4 | 106 | +33.0 | −79.3 | 70 |

[a]Conversion by $^{19}$F NMR (ratio between NF$^+$ and TfO$^-$ signals)

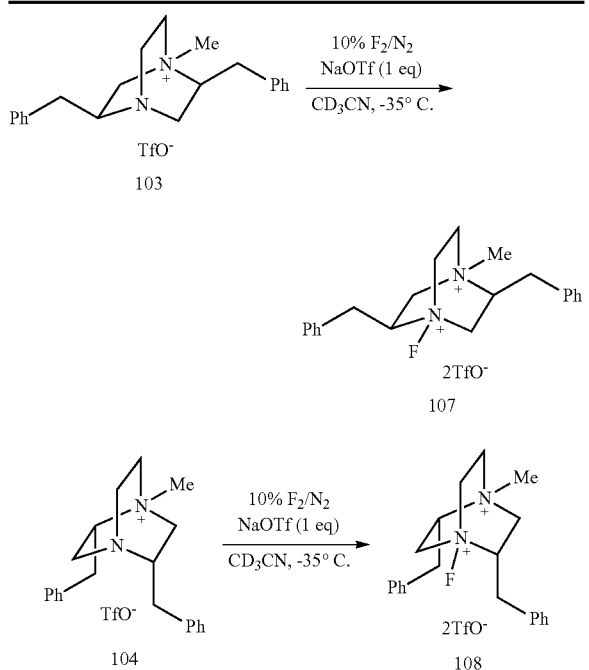

| Entry | Compounds | Equivalents of F₂ | Products | Chemical Shift (ppm) NF⁺ | Chemical Shift (ppm) TfO⁻ | Conversion[a] (%) |
|---|---|---|---|---|---|---|
| 1 | 103 | 3 | 107 | +49.1 | −79.3 | 45 |
| 2 | 103 | 4 | 107 | +49.1 | −79.3 | 50 |
| 3 | 104 | 3 | 108 | +49.0 | −79.3 | 30 |
| 4 | 104 | 4 | 108 | +49.0 | −79.3 | 38 |

[a]Conversion by ¹⁹F NMR (ratio between NF⁺ and TfO⁻ signals)

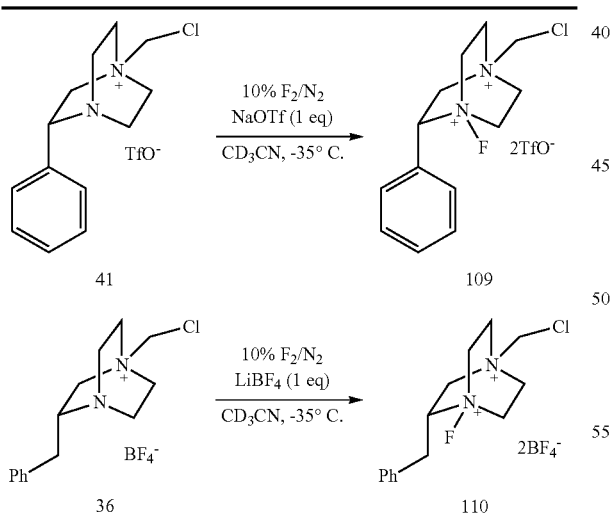

| Entry | Compounds | Equivalents of F₂ | Products | Chemical Shift (ppm) NF⁺ | Chemical Shift (ppm) TfO⁻ | Chemical Shift (ppm) BF₄⁻ | Conversion[a] (%) |
|---|---|---|---|---|---|---|---|
| 1 | 41 | 2 | 109 | +31.0 | −79.3 | — | 98 |
| 2 | 36 | 2 | 110 | +29.5 | — | −151.3 | 88 |

[a]Conversion by ¹⁹F NMR (ratio between NF⁺ and TfO⁻ or BF₄⁻ signals)

(3R)-4-(Chloromethyl)-1-fluoro-2-phenyl-4-aza-1-azoniabicyclo[2.2.2]octane bis(trifluoromethanesulfonate) 109

¹H NMR (400 MHz, CD₃CN) δ 4.42-4.64 (m, 6H, CH₂), 4.66-4.76 (m, 2H, NCH₂CH(Ph)), 4.89-4.97 (m, 1H, CH₂), 5.07 (dd, 1H, J=10.9, J=10.6 Hz, CH₂), 5.46 (d, 1H, J=10.4 Hz, CH₂Cl), 5.51 (d, 1H, J=10.0 Hz, CH₂Cl), 6.22 (t, 1H, J=9.1 Hz, NCH₂CH(Ph)), 7.68 (t, 2H, J=7.6 Hz, ArH), 7.76 (t, 1H, J=7.6 Hz, ArH), 7.86 (d, 2H, J=7.6 Hz, ArH); ¹³C NMR (125.8 MHz, CD₃CN) δ 53.0 (d, ²$J_{C-F}$=15.3 Hz, CH₂), 54.5 (CH₂), 55.3 (CH₂), 58.1 (NCH₂CH(Ph)), 59.1 (d, J=16.2 Hz, CH₂), 70.3, 73.9 (d, ²$J_{C-F}$=16.1 Hz, NCH₂CH(Ph)), 121.50 (q, ¹$J_{C-F}$=320 Hz, CF₃), 123.4 (ArC), 131.2 (ArC), 131.2 (ArC), 133.1 (ArC), 133.1 (ArC), 134.6 (C); ¹⁹F {1H} NMR (376.6 MHz, CD₃CN) δ+30.9 (N–F), −79.3 (SO₃CF₃); IR (neat) (ν, cm⁻¹) 1636, 1247, 1165, 1028; HRMS (ESI): m/z calcd for for C₁₃H₁₇ClFN₂ [M−H]⁺ 255.1059, found 255.1050; MS-Er m/z 148.94 (OTf); [α]²²_D −12 (c 0.785, MeOH); mp 116-118° C.

(2R)-2-Benzyl-1-fluoro-4-methyl-1,4-diazabicyclo[2.2.2]octane-1,4-diium bis(trifluoromethanesulfonate) 111

¹⁹F {1H} NMR (376 MHz, CD₃CN): δ=+29.7 ([N–F]⁺), −79.3 (OTf).

Example 103

Screening Chiral Fluorinating Reagents A and B

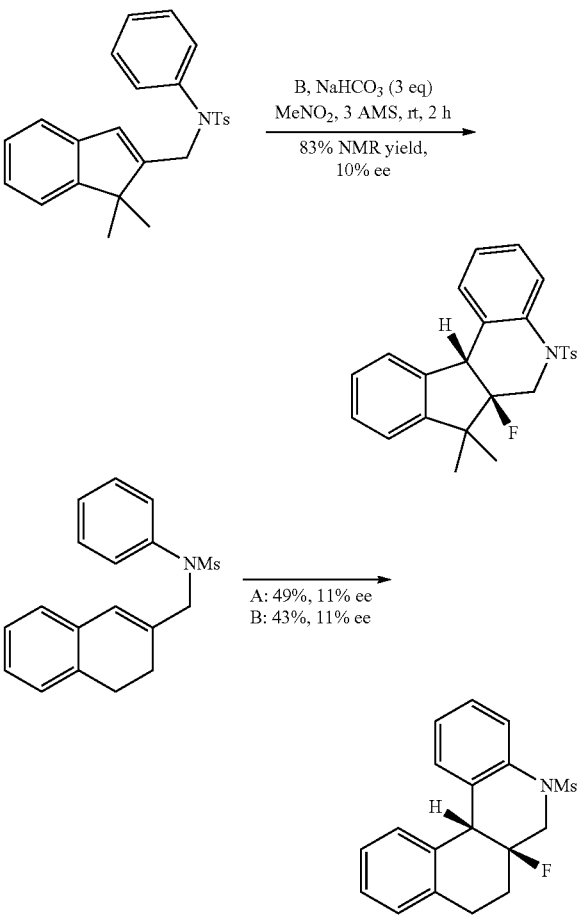

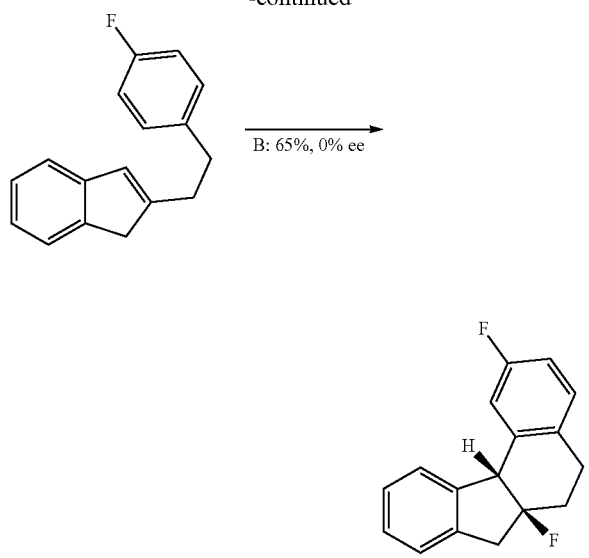
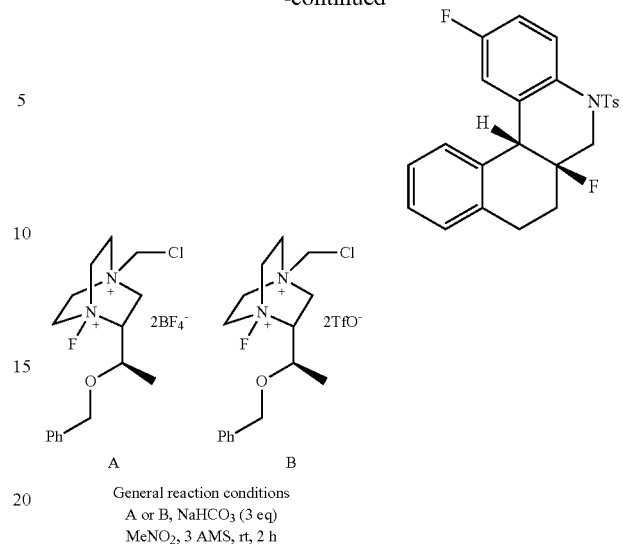
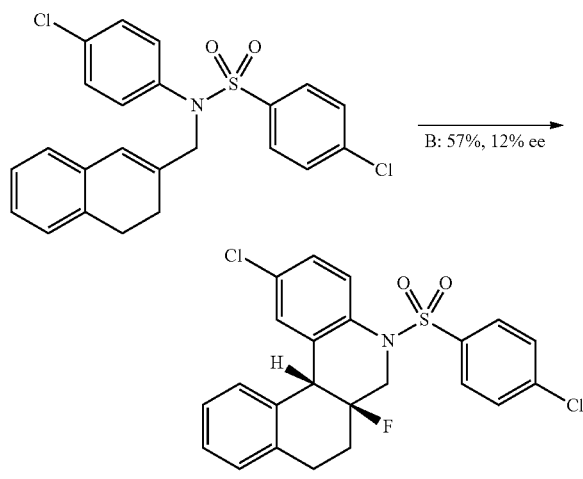
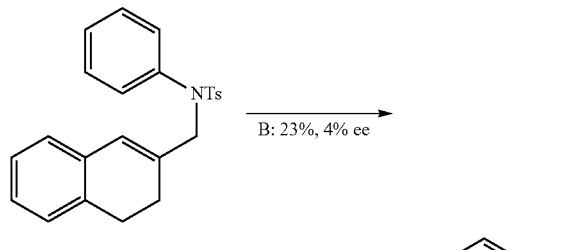
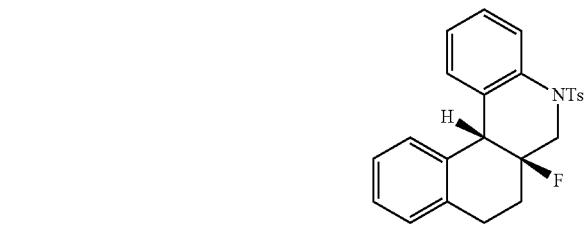
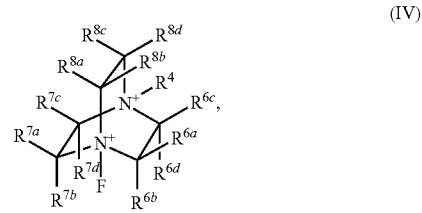

General reaction conditions
A or B, NaHCO₃ (3 eq)
MeNO₂, 3 ÅMS, rt, 2 h

In general, the reactions shown above do not work with less active chiral fluorinating reagents such as those derived from cinchona alkaloids. The compounds of the invention are believed to be the only ones currently available which can achieve the transformations described above in an enantioselective manner.

Work relating to this invention has received funding from the European Community's Seventh Framework Programme FP7/2007-2013 under grant agreement No. PIEF-GA-2008-220034.

The invention claimed is:

1. A product comprising a non-racemic chiral species, wherein the chiral species has the structure:

(IV)

wherein each of $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ is independently selected from the group consisting of: H, aryl and —(CH$_2$)$_n$-aryl, wherein n is from 1 to 4, and wherein aryl is optionally substituted by at least one substituent selected from fluorine, alkyl and alkyl substituted by at least one fluorine; and $R^4$ is an independently selected substituent other than fluorine;

provided that for at least one pair selected from: $R^{6a}$ and $R^{6b}$; $R^{6c}$ and $R^{6d}$; $R^{7a}$ and $R^{7b}$; $R^{7c}$ and $R^{7d}$; $R^{8a}$ and $R^{8b}$; and $R^{8c}$ and $R^{8d}$, one member of that pair is different from the other member of that pair.

2. A product comprising a non-racemic chiral species, wherein the chiral species has the structure:

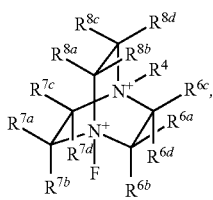

(IV)

wherein each of $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ is independently selected from the group consisting of: H and the following moieties:

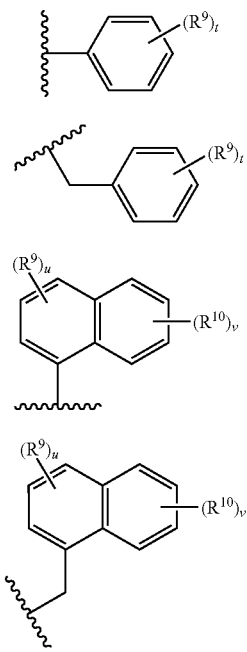

(i)

(ii)

(iii)

(iv)

wherein:
which t is 0, 1, 2, 3, 4 or 5,
u is 0, 1, 2 or 3,
v is 0, 1, 2, 3 or 4, and
$R^9$ and $R^{10}$ are independently selected from halo, cyano, carboxy, sulphoxy, nitro, alkyl and alkyl substituted one or more times by halo; and
$R^4$ is an independently selected substituent other than fluorine;
provided that for at least one pair selected from: $R^{6a}$ and $R^{6b}$; $R^{6c}$ and $R^{6d}$; $R^{7a}$ and $R^{7b}$; $R^{7c}$ and $R^{7d}$; $R^{8a}$ and $R^{8b}$; and $R^{8c}$ and $R^{8d}$, one member of that pair is different from the other member of that pair.

3. The product of claim 2 wherein the chiral species has the structure:

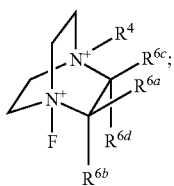

wherein both members of the pair $R^{6a}$ and $R^{6d}$ are the same and both members of the pair $R^{6b}$ and $R^{6c}$ are the same as each other but different from $R^{6a}$ and $R^{6d}$.

4. The product of claim 2 wherein the chiral species has the structure:

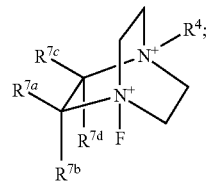

wherein both members of the pair $R^{7a}$ and $R^{7d}$ are the same and both members of the pair $R^{7b}$ and $R^{7c}$ are the same as each other but different from $R^{7a}$ and $R^{7d}$.

5. The product of claim 2 wherein the chiral species has the structure:

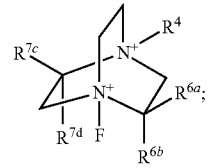

wherein both members of the pair $R^{6a}$ and $R^{7c}$ are the same and both members of the pair $R^{6b}$ and $R^{7d}$ are the same as each other but different from $R^{6a}$ and $R^{7c}$.

6. The product of claim 2 wherein the chiral species has the structure:

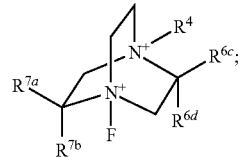

wherein both members of the pair $R^{6c}$ and $R^{7a}$ are the same and both members of the pair $R^{6d}$ and $R^{7b}$ are the same as each other but different from $R^{6c}$ and $R^{7a}$.

7. A product comprising a non-racemic chiral species, wherein the chiral species has the structure:

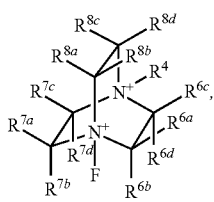

(IV)

wherein each of $R^{6a}$, $R^{6b}$, $R^{6c}$, $R^{6d}$, $R^{7a}$, $R^{7b}$, $R^{7c}$, $R^{7d}$, $R^{8a}$, $R^{8b}$, $R^{8c}$ and $R^{8d}$ is an independently selected substituent; and
$R^4$ is an independently selected substituent other than fluorine;

provided that for at least one pair selected from: $R^{6a}$ and $R^{6b}$; $R^{6c}$ and $R^{6d}$; $R^{7a}$ and $R^{7b}$; $R^{7c}$ and $R^{7d}$; $R^{8a}$ and $R^{8b}$; and $R^{8c}$ and $R^{8d}$, one member of that pair is different from the other member of that pair;

wherein at least one member of $R^{6a}, R^{6b}, R^{6c}, R^{6d}, R^{7a}, R^{7b}, R^{7c}, R^{7d}, R^{8a}, R^{8b}, R^{8c}$ and $R^{8d}$ is a proximally asymmetric substituent, and wherein the or each proximally asymmetric substituent, selected independently of any other proximally asymmetric substituent, has the formula (XVIII):

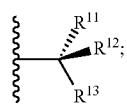

(XVIII)

wherein $R^{11}$, $R^{12}$ and $R^{13}$ are each different and are selected from: H and M-$R^{14}$, M is a bond or an inert linker containing 1, 2, 3, 4 or 5 in-chain atoms; and $R^{14}$ is H or a moiety having from 1 to 20 plural valent atoms, selected from heteroaryl, heteroaryl substituted with one or more substituents, hydrocarbyl, hydrocarbyl substituted with one or more substituents selected from alkoxy, halogen, cyano, carboxy, sulphoxy and nitro.

8. The product of claim 2 wherein $R^4$ is $C_1$-$C_{10}$ alkyl.

9. The product of claim 2 wherein the chiral species has a structure selected from:

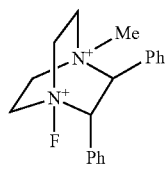

(XII)

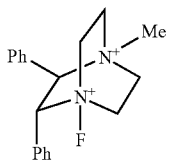

(XIII)

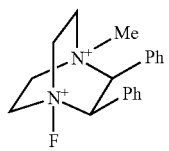

(XVI)

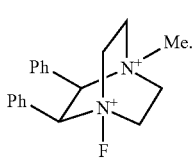

(XVII)

10. A method of fluorinating a nucleophilic substrate to form a fluorinated compound, the method comprising: contacting the substrate with a product as defined in claim 2.

11. The product of 2 wherein $R^4$ is —$CH_3$ or $CH_2Cl$.

12. The product of claim 2, wherein the product is

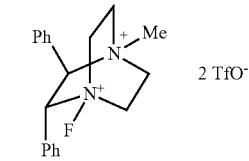

2 TfO⁻ or its enantiomer.

13. The product of claim 2, wherein the product is

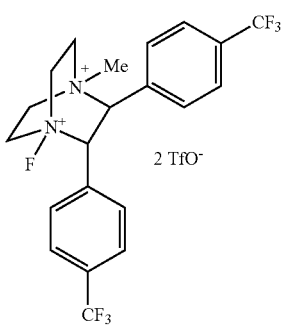

2 TfO⁻ or its enantiomer.

14. The product of claim 2, wherein the product is

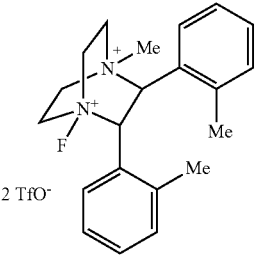

2 TfO⁻ or its enantiomer.

15. The product of claim 1 wherein $R^4$ is $C_1$-$C_{10}$ alkyl.

16. The product of claim 1 wherein $R^4$ is —$CH_3$ or $CH_2Cl$.

17. A method of fluorinating a nucleophilic substrate to form a fluorinated compound, the method comprising: contacting the substrate with a product as defined in claim 1.

* * * * *